United States Patent
Caroff et al.

(10) Patent No.: US 8,093,250 B2
(45) Date of Patent: Jan. 10, 2012

(54) 2-AMINOCARBONYL-PYRIDINE DERIVATIVES

(75) Inventors: Eva Caroff, Ranspach-le-Haut (FR); Kurt Hilpert, Hofstetten (CH); Emmanuel Meyers, Aarau (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 220 days.

(21) Appl. No.: 12/445,352

(22) PCT Filed: Oct. 12, 2007

(86) PCT No.: PCT/IB2007/054155
§ 371 (c)(1),
(2), (4) Date: Apr. 13, 2009

(87) PCT Pub. No.: WO2008/044217
PCT Pub. Date: Apr. 17, 2008

(65) Prior Publication Data
US 2010/0035895 A1 Feb. 11, 2010

(30) Foreign Application Priority Data

Oct. 13, 2006 (WO) .............................. 2006/053773
Oct. 17, 2006 (WO) .............................. 2006/053817

(51) Int. Cl.
*A61K 31/496* (2006.01)
*C07D 213/74* (2006.01)
*C07D 401/04* (2006.01)
*C07D 405/04* (2006.01)
*C07D 409/04* (2006.01)

(52) U.S. Cl. .............. 514/253.09; 514/253.13; 544/364; 544/365

(58) Field of Classification Search .......................... None
See application file for complete search history.

(56) References Cited

U.S. PATENT DOCUMENTS

| | | |
|---|---|---|
| 6,855,715 B1 | 2/2005 | Liebeschuetz et al. |
| 2008/0194576 A1 | 8/2008 | Caroff et al. |
| 2008/0234272 A1 | 9/2008 | Binkert et al. |

FOREIGN PATENT DOCUMENTS

| | | |
|---|---|---|
| EP | 0 407 200 A1 | 1/1991 |
| JP | 53 073586 | 6/1978 |
| WO | WO 02/098856 | 12/2002 |
| WO | WO 2004/052366 | 6/2004 |
| WO | WO 2006/114774 | 11/2006 |
| WO | WO 2008/044217 | 4/2008 |
| WO | WO 2008/050301 | 5/2008 |
| WO | WO 2009/069100 | 6/2009 |
| WO | WO 2009/125365 | 10/2009 |
| WO | WO 2009/125366 | 10/2009 |
| WO | WO 2010/116328 | 10/2010 |
| WO | WO 2010/122504 | 10/2010 |

OTHER PUBLICATIONS

Norgard, Expert Opin. Invest.Drugs vol. 18(8), pp. 1219-1230 (2009).*
Parlow J.J. et al. Bioorg Med Chem Lett. Aug. 15, 2009; 19, 6148-6156. Epub Sep. 10, 2009.
Bartoli, G. et al., "Reaction of dianions of acyclic β-enamino ketones with electrophiles. 3. Nitriles: synthesis of pyridine and pyrimidine derivatives." J. Org. Chem., 1992. 57 (22), 6020-6035.
Bishop et al., 3-(αR)-α((2S,5R)-4 Allyl-2,5-dimethyl-1-piperazinyl)-3-hydroxybenzyl)-N-alkyl-N-arylbenzamides. J. Med. Chem. (2003) 46, 623-633.
Gibson, Mark, Editor. "Pharmaceutical Preformulation and Formulation, A Practical Guide from Candidate Drug Selection to Commercial Dosage Form"; HIS Health Group, Englewood, CO, USA 2001.
Gould, P. et al., "Salt Selection for Basic Drugs", Int. J. Pharm. (1986) 33, 201-217.
Parlow J.J. et al. "Piperazinyl-Glutamate-Pyridines as Potent Orally Bioavailable P2Y12 Antagonists for inhibition of Platelet Aggregation." Bioorg Med Chem Lett. Aug 15, 2009; 19(16): 4657-63. Epub Jun. 25, 2009.
Remington, The Science and Practice of Pharmacy, 21st Edition, Part 5, "Pharmaceutical Manufacturing", Lippincott Williams & Wilkins (2005).
Shao, B. et al., "Phenoxyphenyl Pyridines as Novel State-Dependent, High Potency Sodium Channel Inhibitors." J. Med. Chem., 2004, 47(17), 4277-4285.
Sheth et al., "The Influence of Azone, Propylene Glycol and Polyethylene Glycol on in vitro Skin Penetration of Trifluorothymidine", Int. J. Pharm. (1986) 28, 201-209.

(Continued)

*Primary Examiner* — Emily Bernhardt
(74) *Attorney, Agent, or Firm* — Hoxie & Associates LLC

(57) ABSTRACT

The present invention relates to 2-aminocarbonyl-pyridine derivatives of Formula (I) and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis.

17 Claims, No Drawings

OTHER PUBLICATIONS

Amir, J., et al., "Treatment of Thrombotic Thrombocytopenic Pupura with Antiplatelet Drugs", Blood, vol. 42, No. 1, pp. 27-33 Jul. 1973.
Antithrombotic Trialists' Collaboration, "Collaborative Meta-Analysis of Randomised Trials of Antiplatelet Therapy for Prevention of Death, Myocardial Infarction, and Stroke in High Risk Patients", British Medical Journal, vol. 324, pp. 71-86, 2002.
Balduini, C.L., et al., "Platelet Aggregation in Platelet-Rich Plasma and Whole Blood in 120 Patients with Myeloproliferative Disorders", Coagulation and Transfusion Medicine, vol. 95, No. 1, pp. 82-86, Jan. 1991.
Bertrand, Michel. E., "Randomized Multicenter Comparison of Conventional Anticoagulation Versus Antiplatelet Therapy in Unplanned and Elective Coronary Stenting: . . . " Circulation, vol. 98, pp. 1597-1603, 1998.
Brighton, T.A., et al., "Antiphospholipid Antibodies and Thrombosis", Bailliere's Clinical Haematology, vol. 7, No. 3, pp. 541-557, Sep. 1994.
Caprie Steering Committee, "A randomized, blinded, trial of clopidogrel versus aspirin in patients at risk of ischaemic events (CAPRIE)", The Lancet, vol. 348, pp. 1329-1339, Nov. 16, 1996.
Collins, C.E. et al., "Review Article:Platelets in Inflammatory Bowel Diease-Pathogenic Role and Therapeutic Implications", Aliment Pharmacol. Ther., vol. 11, pp. 237-247, 1997.
Davies, M.J., et al., "Intramyocardial Platelet Aggregation in Patients with Unstable Angina Suffering Sudden Ischemic Cardiac Death", Pathophysiology and Natural History—Platelets, Circulation, vol. 73, No. 3, pp. 418-427, 1986.
Felfernig-Boehm, D., et al., "Early Detection of Preeclampsia by Determination of Platelet Aggregability", Thrombosis Research, vol. 98, pp. 139-146, 2000.
Feokistov et al., "Adenosine A2B receptors, Pharmacological Reviews", vol. 49, No. 4, pp. 381-402, 1997.
Fox, K.A.A., et al. Benefits and Risks of the Combination of Clopidogrel and Aspirin in Patients Undergoing Surgical Revascularization for Non-ST-Elevation Acute Coronary Syndrome: The Clidogrel in Unstable Angina to Prevent Recurrent Ischemic Events (CURE) Trial, Circulation, vol. 110, pp. 1202-1208, 2004.
Halushka, P.V., et al., "Protective Effects of Aspirin in Endotoxic Shock", The Journal of Pharmacology and Experimental Therapeutics, vol. 218, No. 2, pp. 464-469, 1981.
Hovens, M.M.C., et al., "Aspirin in the Prevention and Treatment of Venous Thromboembolism", Journal of Thrombosis and Haemostasis, vol. 4, pp. 1470-1475, 2006.
Kharbanda, R.K., et al., "Prevention of Inflammation-Induced Endothelial Dysfunction: A Novel Vasculo-Protective Action of Aspirin", Circulation, vol. 105, pp. 2600-2604, 2002.
Megalopoulos, A., et al., "Recurrent Arterial Thromboses In a Woman with Heparin Induced Thrombocytopenia, Successfully Managed with Iloprost Followed by Clopidogrel. An Alternative Therapeutic Option for Heparin Induced Thrombocytopenia Type II Syndrome", International Angiology, vol. 25, No. 1, pp. 84-89, Mar. 2006.
Mehta, S.R., et al., "Effects of Pretreatment with Clopidogrel and Aspirin Followed by Long-Term Therapy in Patients Undergoing Percutaneous Coronary Intervention: The PCI-CURE Study", The Lancet, vol. 358, pp. 527-533, Aug. 18, 2001.
Office Action, dated Oct. 28, 2010, U.S. Appl. No. 11/912,545.
Parlow, John J. et al., "Piperazinyl-glutamate-pyrimidines as potent $P2Y_{12}$ antagonists for inhibition of platelet aggregation", 2009, Bioorganic & Medicinal Chemistry Letters, pp. 6148-6156.
Payne, D.A., et al., "Beneficial Effects of Clopidogrel Combined with Aspirin in Reducing Cerebral Emboli in Patients Undergoing Carotid Endarterectomy", Circulation, vol. 109, pp. 1476-1481, 2004.
Stathakis, N.E., et al., Platelet Dysfunction in Essential Thrombocythaemia, Annals of Clinical Research, vol. 6, pp. 198-202, 1974.
Thorsen, C. A., et al., "The Treatment of the Hemolytic-Uremic Syndrome with Inhibitors, of Platelet Function", The American Journal of Medicine, vol. 66, pp. 711-716, Apr. 1979.
Triadou, P., et al., "Platelet Function in Sickle Cell Disease During Steady State", Nouvelle Revue Francaise Hematologie, vol. 32, pp. 137-142, 1990.
University of Perugia, "Aspirin for the Prevention of Recurrent Venous Thromboembolism and Cardiovascular Events", pp. 1-3, ClinicalTrials.gov/ct/show/NCT00222677, Sep. 13, 2005.
Yao, S., et al., "Clopidogrel is More Effective Than Aspirin as Adjuvant Treatment to Prevent Reocclusion After Thrombolysis", Am. J. Physiol., vol. 267, pp. H488-H493, 1994.

* cited by examiner

2-AMINOCARBONYL-PYRIDINE DERIVATIVES

CROSS REFERENCE TO RELATED APPLICATIONS

This application is a United States National Stage Application under 35 U.S.C. 371 of PCT/IB2007/054155 filed on Oct. 12, 2007, which claims the benefit of PCT/IB2006/053773 filed on Oct. 13, 2006 and PCT/IB2006/053817 filed on Oct. 17, 2006, the contents of each of which are incorporated herein by reference.

FIELD OF THE INVENTION

The present invention relates to 2-aminocarbonyl-pyridine derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Haemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors $P2Y_1$ and $P2Y_{12}$.

Antagonists of the platelet ADP receptor have been identified and display inhibition of platelet aggregation and antithrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype $P2Y_{12}$.

Some $P2Y_{12}$ antagonists like AR-C69931MX (Cangrelor) or AZD6140 have reached phase II clinical studies. These inhibitors are selective platelet ADP receptor antagonists, which inhibit ADP-dependent platelet aggregation, and are effective in vivo.

Piperazino-carbonylmethylaminocarbonyl-naphtyl or -quinolyl derivatives have been described as ADP receptor antagonists in WO 02/098856 and WO 2004/052366.

DESCRIPTION OF THE INVENTION

The present invention firstly relates to the compounds of formula I

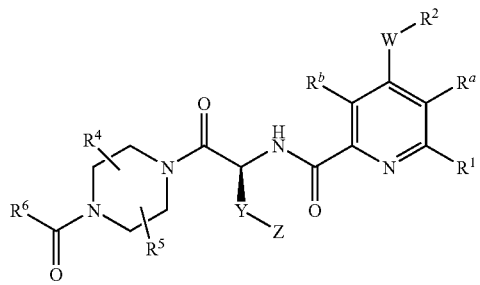

wherein
$R^1$ represents halogen or an imidazolyl, pyrazolyl, 1,2,3-triazolyl or 1,2,4-triazolyl ring, which ring may be substituted by a methyl group, or also $R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;

W represents a bond and $R^2$ represents hydrogen, halogen, alkyl, hydroxyalkyl, alkoxyalkyl, cycloalkyl, aryl or heteroaryl; or W represents —O— or —S— and $R^2$ represents alkyl, cycloalkyl, aryl or heterocyclyl; or W represents —$NR^3$—, $R^2$ represents alkyl, hydroxyalkyl or alkoxyalkyl and $R^3$ represents hydrogen or alkyl; or W represents —C≡C— and $R^2$ represents hydroxyalkyl or alkoxyalkyl; or W represents —$NR^3$— and $R^2$ and $R^3$ form, together with the nitrogen that carries them, a heterocyclic ring of 4 to 7 members wherein the members needed to complete said heterocyclic ring are each independently selected from —$CH_2$— and —$CHR^x$—, it being understood however that said heterocyclic ring does not contain more than one —$CHR^x$— member, $R^x$ representing hydroxy, hydroxymethyl, alkoxymethyl or alkoxy; or also W represents —$NR^3$— and $R^2$ and $R^3$ form, together with the nitrogen that carries them, an imidazolyl, pyrazolyl, 1,2,3-triazolyl or 1,2,4-triazolyl ring, which ring is optionally substituted by a methyl group;

$R^a$ represents hydrogen or fluorine and $R^b$ represents hydrogen, or $R^a$ represents hydrogen and
$R^b$ represents alkoxy;
each of $R^4$ and $R^5$ represents independently hydrogen or methyl;
$R^6$ represents alkoxy; and
Y represents alkylene or phenylalkylene, and Z represents hydrogen, —OH, —COOH, cyano, tetrazolyl or —$COOR^7$, $R^7$ representing alkyl; it being understood that:
when $R^1$ represents halogen then W and $R^2$ are not such that W represents a bond and $R^2$ represents hydrogen or halogen, and when R$^a$ represents fluorine then: i) R$^1$ represents phenyl optionally substituted once by fluorine, methyl, methoxy, trifluoromethyl or trifluoromethoxy, ii) W does not represent —O— or —S—, and iii) if W is a bond, then R$^2$ does not represent hydrogen;

and to the salts of such compounds.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The compounds of formula I are P2Y$_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

The following paragraphs provide definitions of the various chemical moieties for the compounds according to the invention. Said definitions are intended to apply uniformly throughout the specification and claims unless an otherwise expressly set out definition provides a broader or narrower definition.

The term "halogen" refers to fluorine, chlorine, bromine or iodine, preferably to fluorine, chlorine or bromine and more preferably to fluorine or chlorine.

The term "alkyl" (whether used alone or in combination) refers to a saturated straight or branched chain alkyl group containing 1 to 7 carbon atoms (e.g. methyl, ethyl, propyl, iso-propyl, butyl, iso-butyl, sec-butyl, tert-butyl, n-pentyl, neopentyl, iso-pentyl, n-hexyl, iso-hexyl, n-heptyl or iso-heptyl), and more preferably 1 to 4 carbon atoms.

The term "hydroxyalkyl", as used herein, refers to an alkyl group as previously defined wherein one hydrogen atom has been replaced by a hydroxy (i.e. —OH) group. Examples of hydroxyalkyl include, but are not limited to, hydroxymethyl, 2-hydroxy-ethyl, 2-hydroxy-propyl, 2-hydroxy-1-methyl-ethyl, 2-hydroxy-1,1-dimethyl-ethyl, 1-hydroxy-propyl, 3-hydroxy-propyl, 1-hydroxy-butyl, 3-hydroxy-butyl, 4-hydroxy-butyl, 3-hydroxy-pentyl and 3-hydroxy-3-methyl-butyl.

The term "alkoxyalkyl", as used herein, refers to an alkyl group as previously defined wherein one hydrogen atom has been replaced by an alkoxy group as defined hereafter. Examples of alkoxyalkyl include, but are not limited to, methoxymethyl and 2-methoxy-1-methyl-ethyl.

The term "cycloalkyl", as used herein, alone or in any combination, refers to a saturated cyclic hydrocarbon moiety containing 3 to 7 carbon atoms which may be substituted once by hydroxy, hydroxymethyl, alkoxymethyl (preferably methoxymethyl or ethoxymethyl and more preferably methoxymethyl) or alkoxy (preferably methoxy or ethoxy and more preferably methoxy). Representative examples of cycloalkyl include, but are not limited to, cyclopropyl, cyclobutyl, cyclopentyl, cyclohexyl, 4-hydroxy-cyclohexyl, 2-hydroxy-cyclohexyl, 2-hydroxymethyl-cyclopropyl and 2-methoxymethyl-cyclopropyl.

The term "aryl" refers to an aromatic cyclic group with one, two or three rings, having from 6 to 14 carbon ring-atoms and preferably from 6 to 10 carbon ring-atoms, for example to phenyl or naphthyl groups (and notably to phenyl groups). Any aryl group (and in particular any phenyl group) as defined herein may be substituted with one, two or more substituents (preferably with one to three substituents, more preferably with one or two substituents and notably with one substituent), each independently selected from the group consisting of halogen, alkyl and alkoxy. Specific examples of aryl groups are phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2,4-difluorophenyl, 3,4-difluorophenyl, 2,4-dimethoxyphenyl and 2,4-dimethylphenyl.

The term "heteroaryl", as used herein, alone or in combination, refers to a mono-, bi- or tricyclic aromatic ring system containing up to 14 ring atoms wherein at least one of the rings contains at least one heteroatom independently selected from the group consisting of nitrogen, oxygen and sulfur; in addition, the term "heteroaryl" may also refer to 1-oxy-pyridinyl groups. The heteroaryl group can be unsubstituted or substituted with 1 to 3 substituents (preferably 1 to 2 substituents and more preferably 1 substituent) selected independently from the group consisting of halogen, alkyl, alkoxy, trifluoromethyl and trifluoromethoxy. Representative examples of heteroaryl include, but are not limited to, thienyl, furanyl, pyrrolyl, pyrazolyl, thiazolyl, imidazolyl, oxazolyl, pyridinyl, 1-oxy-4-pyridinyl, 1-oxy-3-pyridinyl, 1-oxy-2-pyridinyl, pyrimidinyl, quinolinyl, benzimidazolyl, benzothiazolyl, benzothienyl, benzoxazolyl, benzofuranyl, indolyl, carbazolyl, phenothiazinyl and phenoxazinyl.

The term "monocyclic heteroaryl", as used herein, refers to a monocyclic aromatic ring system containing 5 or 6 ring atoms among which 1 or 2 may be heteroatoms selected from O, N and S. The monocyclic heteroaryl group can be unsubstituted or substituted with 1 to 2 substituents (preferably 1 substituent) selected independently from the group consisting of halogen, alkyl, alkoxy, trifluoromethyl and trifluoromethoxy. Representative examples of monocyclic heteroaryl include, but are not limited to, thienyl, furanyl, pyrrolyl, pyrazolyl, thiazolyl, imidazolyl, oxazolyl, pyridinyl and pyrimidinyl.

The term "heterocyclyl", as used herein, alone or in any combination, refers to an unsubstituted saturated monocyclic moiety of 3 to 7 ring members containing 1 to 2 heteroatoms selected from nitrogen, oxygen and sulfur, it being however understood that (i) a heterocyclyl group is not attached to the rest of the molecule by a nitrogen atom, (ii) a heterocyclyl group of 3 or 4 ring members contains only one heteroatom which is a nitrogen atom and (iii) a heterocyclyl group does not contain 2 sulfur atoms. The sulfur atom of a heterocyclyl group may be in an oxidised form, i.e. as a sulfoxide or sulfonyl. Representative examples of heterocyclyl include, but are not limited to, azetidinyl, pyrrolidinyl, tetrahydrofuranyl, piperidinyl, piperazinyl, morpholinyl and thiomorpholinyl.

The term "alkoxy" (whether used alone or in combination) refers to a saturated straight or branched chain alkoxy group containing 1 to 6 carbon atoms (e.g. methoxy, ethoxy, propoxy, iso-propoxy, butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms.

The term "alkoxyalkyl", as used herein, refers to an alkyl group as previously defined wherein one hydrogen atom has been replaced by an alkoxy group as defined hereafter. Examples of alkoxyalkyl include, but are not limited to, methoxymethyl and 2-methoxy-1-methyl-ethyl.

The term "alkylene", used alone or in combination, refers to a straight or branched divalent saturated hydrocarbon chain group with one to six carbon atoms and preferably one to four carbon atoms. Representative examples of alkylene include, but are not limited to, methylene (—CH$_2$—), ethylene (—CH$_2$—CH$_2$—), n-propylene (—CH$_2$—CH$_2$—CH$_2$—) and iso-propylene (—CH$_2$—CH(CH$_3$)—).

The term "phenylalkylene", as used herein, refers to an unsubstituted divalent phenylalkyl group wherein the alkyl is as previously defined, said divalent group being attached to the rest of the molecule by, on the one side, one of the carbon atoms of the phenyl group and by, one the other side, one of the carbon atoms of the alkyl group.

Moreover, the sign "*" placed near an atom will be used to designate the point of attachment of a radical to the rest of a molecule. For example:

designates the tetrahydrofuran-3-yl radical.

Besides, the following paragraphs provide definitions of various other terms. Said definitions are intended to apply uniformly throughout the specification and claims unless an otherwise expressly set out definition provides a broader or narrower definition.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

The compounds of formula I will in particular be compounds of formula $I_{CE}$

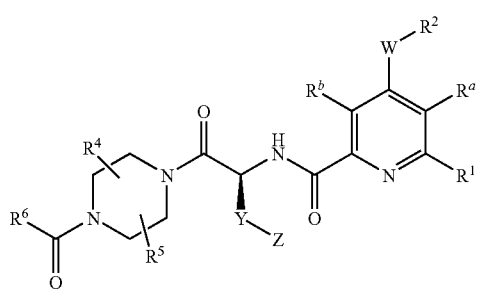

wherein $R^1$ represents halogen, pyrazolyl or phenyl optionally substituted once by halogen or methyl;

W represents a bond and $R^2$ represents hydrogen, halogen, alkyl, hydroxyalkyl, cycloalkyl, aryl or heteroaryl;

W represents —O— or —S— and $R^2$ represents alkyl, heterocyclyl, cycloalkyl of 3 to 7 carbon atoms optionally substituted once by a substituent selected from the group consisting of hydroxy, hydroxymethyl and alkoxymethyl, phenyl optionally substituted once by an alkoxy group; or W represents —NR$^3$—, $R^2$ represents alkyl or hydroxyalkyl and $R^3$ represents hydrogen; or W represents —C≡C— and $R^2$ represents hydroxyalkyl; or W represents —NR$^3$— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy or alkoxy; or also W represents —NR$^3$— and $R^2$ and $R^3$ form, together with the nitrogen that carries them, a pyrazolyl ring;

$R^a$ represents hydrogen or fluorine and $R^b$ represents hydrogen, or $R^a$ represents hydrogen and $R^b$ represents alkoxy;

one of $R^4$ and $R^5$ represents hydrogen or methyl and the other represents hydrogen; $R^6$ represents alkoxy; and Y represents alkylene and Z represents hydrogen, —OH, —COOH, cyano, tetrazolyl or —COOR$^7$, $R^7$ representing alkyl;

it being understood that:

when $R^1$ represents halogen, then W and $R^2$ are not such that W represents a bond and $R^2$ represents hydrogen or halogen, and when $R^a$ represents fluorine then: i) $R^1$ represents phenyl optionally substituted once by fluorine or methyl, ii) W does not represent —O— or —S—, and iii) if W is a bond, then $R^2$ does not represent hydrogen.

A particular embodiment of this invention relates to compounds of formula I that are also compounds of formula $I_p$

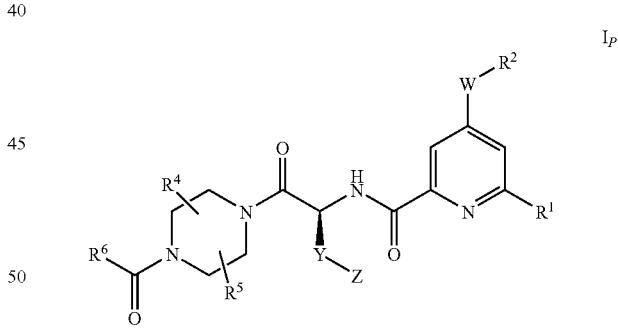

wherein $R^1$ represents halogen or an imidazolyl, pyrazolyl, 1,2,3-triazolyl or 1,2,4-triazolyl ring, which ring may be substituted by a methyl group, or also $R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;

W represents a bond and $R^2$ represents hydrogen, halogen, alkyl, hydroxyalkyl, alkoxyalkyl, cycloalkyl, aryl or heteroaryl; or W represents —O— or —S— and $R^2$ represents alkyl, cycloalkyl, aryl or heterocyclyl; or W represents —NR³—, R² represents alkyl, hydroxyalkyl or alkoxyalkyl and R³ represents hydrogen or alkyl; or W represents —C≡C— and R² represents hydroxyalkyl or alkoxyalkyl; or W represents —NR³— and R² and R³ form, together with the nitrogen that carries them, a heterocyclic ring of 4 to 7 members wherein the members needed to complete said heterocyclic ring are each independently selected from —CH₂— and —CHR$^x$—, it being understood however that said heterocyclic ring does not contain more than one —CHR$^x$— member, R$^x$ representing hydroxy, hydroxymethyl, alkoxymethyl or alkoxy; or also W represents —NR³— and R² and R³ form, together with the nitrogen that carries them, an imidazolyl, pyrazolyl, 1,2,3-triazolyl or 1,2,4-triazolyl ring, which ring is optionally substituted by a methyl group;

each of R⁴ and R⁵ represents independently hydrogen or methyl;

R⁶ represents alkoxy; and

Y represents alkylene or phenylalkylene, and Z represents —OH, —COOH, cyano, tetrazolyl or —COOR⁷, R⁷ representing alkyl;

it being understood that:
when R¹ represents halogen then W and R² are not such that W represents a bond and R² represents hydrogen or halogen, and
when W represents a bond and R² represents hydrogen or halogen then R¹ does not represent halogen;

and to the salts of such compounds.

The compounds of formula $I_p$ will in particular be compounds of formula $I_{CEP}$

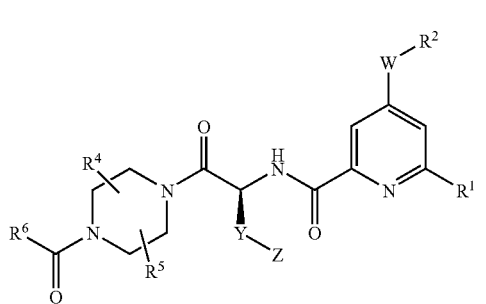

$I_{CEP}$ wherein
R¹ represents halogen, pyrazolyl or phenyl optionally substituted once by halogen or methyl;

W represents a bond and R² represents hydrogen, halogen, alkyl, hydroxyalkyl, cycloalkyl, aryl or heteroaryl;

W represents —O— or —S— and R² represents alkyl, heterocyclyl, cycloalkyl of 3 to 7 carbon atoms optionally substituted once by a substituent selected from the group consisting of hydroxy, hydroxymethyl and alkoxymethyl, phenyl optionally substituted once by an alkoxy group; or W represents —NR³—, R² represents alkyl or hydroxyalkyl and R³ represents hydrogen; or W represents —C≡C— and R² represents hydroxyalkyl; or W represents —NR³— and R² and R³ form, together with the nitrogen that carries them, a heterocyclic ring of 4 to 7 members wherein the members needed to complete said heterocyclic ring are each independently selected from —CH₂— and —CHR$^x$—, it being understood however that said heterocyclic ring does not contain more than one —CHR$^x$— member, R$^x$ representing hydroxy or alkoxy; or also W represents —NR³— and R² and R³ form, together with the nitrogen that carries them, a pyrazolyl ring; one of R⁴ and R⁵ represents hydrogen or methyl and the other represents hydrogen;

R⁶ represents alkoxy; and

Y represents alkylene and Z represents —OH, —COOH, tetrazolyl or cyano; it being understood that:
when R¹ represents halogen, then W and R² are not such that W represents a bond and R² represents hydrogen or halogen, and
when W represents a bond and R² represents hydrogen or halogen, then R¹ does not represent halogen.

Preferred compounds of formula I will be those wherein at least one of the following characteristics is present:
R¹ represents halogen or an imidazolyl, pyrazolyl, 1,2,3-triazolyl or 1,2,4-triazolyl ring, which ring may be substituted by a methyl group, or also R¹ represents phenyl optionally substituted once or twice (and preferably once) by substituents each independently selected from the group consisting of halogen, methyl, methoxy, trifluoromethyl and trifluoromethoxy;

W represents a bond and R² represents hydrogen, halogen, alkyl, hydroxyalkyl, alkoxyalkyl, cycloalkyl, monocyclic heteroaryl or phenyl optionally substituted by up to two substituents each independently selected from the group consisting of halogen, alkyl and alkoxy; or W represents —O— or —S— and R² represents alkyl, cycloalkyl, aryl or heterocyclyl; or W represents —NR³—, R² represents alkyl, hydroxyalkyl or alkoxyalkyl and R³ represents hydrogen or alkyl; or W represents —C≡C— and R² represents hydroxyalkyl or alkoxyalkyl; or W represents —NR³— and R² and R³ form, together with the nitrogen that carries them, a heterocyclic ring of 4 to 7 members wherein the members needed to complete said heterocyclic ring are each independently selected from —CH₂— and —CHR$^x$—, it being understood however that said heterocyclic ring does not contain more than one —CHR$^x$— member, R$^x$ representing hydroxy, hydroxymethyl, alkoxymethyl or alkoxy; or also W represents —NR³— and R² and R³ form, together with the nitrogen that carries them, an imidazolyl, pyrazolyl, 1,2,3-triazolyl or 1,2,4-triazolyl ring;

R$^a$ represents hydrogen or fluorine and R$^b$ represents hydrogen;

R⁶ represents alkoxy of 1 to 4 carbon atoms;

Y represents alkylene or phenylalkylene, and Z represents hydrogen, —OH, —COOH, cyano or tetrazolyl.

Preferred compounds of formula $I_p$ will be those wherein at least one of the following characteristics is present:
R¹ represents halogen or an imidazolyl, pyrazolyl, 1,2,3-triazolyl or 1,2,4-triazolyl ring, which ring may be substituted by a methyl group, or also R¹ represents phenyl optionally substituted once or twice (and preferably once) by substituents each independently selected from the group consisting of halogen, methyl, methoxy, trifluoromethyl and trifluoromethoxy;

W represents a bond and R² represents hydrogen, halogen, alkyl, hydroxyalkyl, alkoxyalkyl, cycloalkyl, monocyclic heteroaryl or phenyl optionally substituted by up to two substituents each independently selected from the group consisting of halogen, alkyl and alkoxy; or W represents —O— or —S— and R² represents alkyl, cycloalkyl, aryl or heterocyclyl; or W represents —NR³—, R² represents alkyl, hydroxyalkyl or alkoxyalkyl and R³ represents hydrogen or alkyl; or W represents —C≡C— and $R^2$ represents hydroxyalkyl or alkoxyalkyl; or W represents —NR³— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, $R^x$ representing hydroxy, hydroxymethyl, alkoxymethyl or alkoxy; or also W represents —NR³— and $R^2$ and $R^3$ form, together with the nitrogen that carries them, an imidazolyl, pyrazolyl, 1,2,3-triazolyl or 1,2,4-triazolyl ring;

$R^6$ represents alkoxy of 1 to 4 carbon atoms;

Y represents alkylene or phenylalkylene, and Z represents —OH, —COOH, cyano or tetrazolyl.

More preferred compounds of formula I will be those wherein at least one of the following characteristics is present:

$R^1$ represents phenyl optionally substituted once by a substituent selected from the group consisting of halogen, methyl, methoxy, trifluoromethyl and trifluoromethoxy;

W represents a bond and $R^2$ represents alkyl, hydroxyalkyl, alkoxyalkyl, cycloalkyl, monocyclic heteroaryl or phenyl optionally substituted once by a member of the group consisting of halogen, alkyl and alkoxy; or W represents —O— or —S— and $R^2$ represents alkyl, cycloalkyl, phenyl or heterocyclyl; or W represents —NR³—, $R^2$ represents alkyl, hydroxyalkyl or alkoxyalkyl and $R^3$ represents hydrogen or alkyl; or W represents —C≡C— and $R^2$ represents hydroxyalkyl or alkoxyalkyl; or W represents —NR³— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, $R^x$ representing hydroxy, hydroxymethyl, alkoxymethyl or alkoxy; or also or also W represents —NR³— and $R^2$ and $R^3$ form, together with the nitrogen that carries them, an imidazolyl, pyrazolyl, 1,2,3-triazolyl or 1,2,4-triazolyl ring;

$R^a$ represents hydrogen or fluorine and $R^b$ represents hydrogen;

$R^6$ represents alkoxy of 2 to 4 carbon atoms;

Y represents alkylene or phenylalkylene, and Z represents —OH, —COOH or tetrazolyl.

More preferred compounds of formula $I_p$ will be those wherein at least one of the following characteristics is present:

$R^1$ represents phenyl optionally substituted once by a substituent selected from the group consisting of halogen, methyl, methoxy, trifluoromethyl and trifluoromethoxy;

W represents a bond and $R^2$ represents alkyl, hydroxyalkyl, alkoxyalkyl, cycloalkyl, monocyclic heteroaryl or phenyl optionally substituted once by a member of the group consisting of halogen, alkyl and alkoxy; or W represents —O— or —S— and $R^2$ represents alkyl, cycloalkyl, phenyl or heterocyclyl; or W represents —NR³—, $R^2$ represents alkyl, hydroxyalkyl or alkoxyalkyl and $R^3$ represents hydrogen or alkyl; or W represents —C≡C— and $R^2$ represents hydroxyalkyl or alkoxyalkyl; or W represents —NR³— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, $R^x$ representing hydroxy, hydroxymethyl, alkoxymethyl or alkoxy; or also or also W represents —NR³— and $R^2$ and $R^3$ form, together with the nitrogen that carries them, an imidazolyl, pyrazolyl, 1,2,3-triazolyl or 1,2,4-triazolyl ring;

$R^6$ represents alkoxy of 1 to 3 carbon atoms;

Y represents alkylene or phenylalkylene, and Z represents —OH, —COOH or tetrazolyl.

Even more preferred compounds of formula $I_p$ will be those wherein at least one of the following characteristics is present:

$R^1$ represents phenyl optionally substituted once by halogen or methyl;

W represents a bond and $R^2$ represents hydroxyalkyl, alkoxyalkyl or cycloalkyl optionally substituted once by a member of the group consisting of hydroxy, hydroxymethyl, methoxymethyl, methoxy and ethoxy; or W represents —O— or —S— and $R^2$ represents heterocyclyl; or W represents —NR³—, $R^2$ represents hydroxyalkyl or alkoxyalkyl and $R^3$ represents hydrogen; or W represents —C≡C— and $R^2$ represents hydroxyalkyl or alkoxyalkyl; or W represents —NR³— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$-member, $R^x$ representing hydroxy, hydroxymethyl, alkoxymethyl, methoxy or ethoxy; or also or also W represents —NR³— and $R^2$ and $R^3$ form, together with the nitrogen that carries them, an imidazolyl, pyrazolyl, 1,2,3-triazolyl or 1,2,4-triazolyl ring;

$R^a$ represents hydrogen or fluorine and $R^b$ represents hydrogen; one of $R^4$ and $R^5$ represents hydrogen or methyl and the other represents hydrogen;

$R^6$ represents alkoxy of 3 or 4 carbon atoms (especially n-propoxy or n-butoxy);

Y represents alkylene or phenylalkylene and Z represents —COOH.

Even more preferred compounds of formula $I_p$ will be those wherein at least one of the following characteristics is present:

$R^1$ represents phenyl optionally substituted once by halogen or methyl;

W represents a bond and $R^2$ represents hydroxyalkyl, alkoxyalkyl or cycloalkyl optionally substituted once by a member of the group consisting of hydroxy, hydroxymethyl, methoxymethyl, methoxy and ethoxy; or W represents —O— or —S— and $R^2$ represents heterocyclyl; or W represents —NR³—, $R^2$ represents hydroxyalkyl or alkoxyalkyl and $R^3$ represents hydrogen; or W represents —C≡C— and $R^2$ represents hydroxyalkyl or alkoxyalkyl; or W represents —NR³— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl, methoxy or ethoxy; or also or also W represents —NR$^3$— and R$^2$ and R$^3$ form, together with the nitrogen that carries them, an imidazolyl, pyrazolyl, 1,2,3-triazolyl or 1,2,4-triazolyl ring;

one of R$^4$ and R$^5$ represents hydrogen or methyl and the other represents hydrogen;

Y represents alkylene or phenylalkylene and Z represents —COOH.

Particularly preferred compounds of formula I will be those wherein at least one of the following characteristics is present:

R$^1$ represents phenyl;

W represents a bond and R$^2$ represents hydroxyalkyl or cycloalkyl optionally substituted once (and preferably substituted once) by hydroxy, hydroxymethyl or methoxymethyl; or W represents —O— or —S— and R$^2$ represents heterocyclyl (and notably tetrahydrofuran-3-yl); or W represents —NR$^3$—, R$^2$ represents hydroxyalkyl and R$^3$ represents hydrogen; or W represents —C≡C— and R$^2$ represents hydroxyalkyl; or W represents —NR$^3$— and R$^2$ and R$^3$ form, together with the nitrogen that carries them, a heterocyclic ring of 4 to 7 members, wherein one of these members needed to complete said heterocyclic ring is —CHR$^x$— and the other members are each —CH$_2$—, R$^x$ representing hydroxy, hydroxymethyl, methoxymethyl or methoxy; or also or also W represents —NR$^3$— and R$^2$ and R$^3$ form, together with the nitrogen that carries them, an imidazolyl, pyrazolyl, 1,2,3-triazolyl or 1,2,4-triazolyl ring (and notably a pyrazolyl ring);

R$^a$ represents hydrogen or fluorine and R$^b$ represents hydrogen;

each of R$^4$ and R$^5$ represents hydrogen;

R$^6$ represents butoxy (especially n-butoxy);

Y represents alkylene and Z represents —COOH.

Particularly preferred compounds of formula I$_p$ will be those wherein at least one of the following characteristics is present:

R$^1$ represents phenyl;

W represents a bond and R$^2$ represents hydroxyalkyl or cycloalkyl optionally substituted once (and preferably substituted once) by hydroxy, hydroxymethyl or methoxymethyl; or W represents —O— or —S— and R$^2$ represents heterocyclyl (and notably tetrahydrofuran-3-yl); or W represents —NR$^3$—, R$^2$ represents hydroxyalkyl and R$^3$ represents hydrogen; or W represents —C≡C— and R$^2$ represents hydroxyalkyl; or W represents —NR$^3$— and R$^2$ and R$^3$ form, together with the nitrogen that carries them, a heterocyclic ring of 4 to 7 members, wherein one of these members needed to complete said heterocyclic ring is —CHR$^x$— and the other members are each —CH$_2$—, R$^x$ representing hydroxy, hydroxymethyl, methoxymethyl or methoxy; or also or also W represents —NR$^3$— and R$^2$ and R$^3$ form, together with the nitrogen that carries them, an imidazolyl, pyrazolyl, 1,2,3-triazolyl or 1,2,4-triazolyl ring (and notably a pyrazolyl ring);

each of R$^4$ and R$^5$ represents hydrogen;

R$^6$ represents ethoxy;

Y represents alkylene and Z represents —COOH.

Furthermore, compounds of formula I or I$_p$ wherein Y represents alkylene will generally be preferred over other compounds of formula I or I$_p$. Besides, compounds of formula I or I$_p$ wherein Z represents —OH, —COOH or tetrazolyl will generally be preferred over other compounds of formula I or I$_p$.

When W represents —O— or —S— and R$^2$ represents heterocyclyl, R$^2$ will preferably represent a group of the formula

wherein X represents O, S, NH, SO or SO$_2$ (and in particular O) and either m is 1 and n is 2 or 3 or m is 2 and n is 2.

In particular, when W represents —O— or —S— and R$^2$ represents heterocyclyl, R$^2$ will represent a group of one of the following formulae:

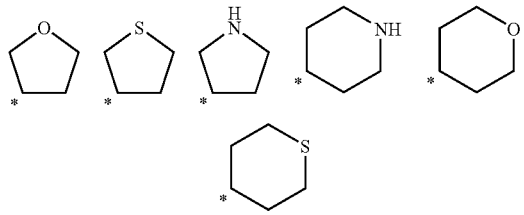

and notably the group of the following formula

The following main embodiments of compounds of formula I or I$_P$ (or of salts thereof, in particular of pharmaceutically acceptable salts thereof) are particularly preferred.

According to a first main embodiment of this invention, the compounds of formula I will be such that W represents a bond; such compounds will be collectively designated by "compounds of formula I$_B$" throughout the specification and claims. In such case, the compounds of formula I$_B$ will preferably be such that:

R$^1$ represents phenyl optionally substituted once or twice by substituents each independently selected from the group consisting of halogen, methyl, methoxy, trifluoromethyl and trifluoromethoxy;

R$^2$ represents hydrogen, halogen, alkyl, hydroxyalkyl, alkoxyalkyl, cycloalkyl, monocyclic heteroaryl or phenyl optionally substituted by up to two substituents each independently selected from the group consisting of halogen, alkyl and alkoxy;

R$^6$ represents alkoxy of 1 to 4 carbon atoms;

Y represents alkylene or phenylalkylene and Z represents hydrogen, —OH, —COOH, tetrazolyl or —COOR$^7$, R$^7$ representing alkyl.

According to a variant of said first main embodiment of this invention, the compounds of formula I will be compounds of formula $I_P$ that are such that W represents a bond; such compounds will be collectively designated by "compounds of formula $I_{BP}$" throughout the specification and claims. In such case, the compounds of formula $I_{BP}$ will preferably be such that:
- $R^1$ represents phenyl optionally substituted once or twice by substituents each independently selected from the group consisting of halogen, methyl, methoxy, trifluoromethyl and trifluoromethoxy;
- $R^2$ represents hydrogen, halogen, alkyl, hydroxyalkyl, alkoxyalkyl, cycloalkyl, monocyclic heteroaryl or phenyl optionally substituted by up to two substituents each independently selected from the group consisting of halogen, alkyl and alkoxy;
- $R^6$ represents alkoxy of 1 to 4 carbon atoms;
- Y represents alkylene or phenylalkylene and Z represents —OH, —COOH, tetrazolyl or —COOR$^7$, $R^7$ representing alkyl.

Preferably, the compounds of formula $I_B$ will at least have one of the following characteristics:
- $R^1$ represents phenyl optionally substituted once by a substituent selected from the group consisting of halogen, methyl, methoxy, trifluoromethyl and trifluoromethoxy;
- $R^2$ represents alkyl, hydroxyalkyl, alkoxyalkyl, cycloalkyl, monocyclic heteroaryl or phenyl optionally substituted once by a member of the group consisting of halogen, alkyl and alkoxy;
- $R^a$ represents hydrogen or fluorine and $R^b$ represents hydrogen;
- one of $R^4$ and $R^5$ represents hydrogen or methyl and the other represents hydrogen;
- $R^6$ represents alkoxy of 2 to 4 carbon atoms (especially n-propoxy or n-butoxy);
- Y represents alkylene or phenylalkylene and Z represents —COOH.

Preferably, the compounds of formula $I_{BP}$ will at least have one of the following characteristics:
- $R^1$ represents phenyl optionally substituted once by a substituent selected from the group consisting of halogen, methyl, methoxy, trifluoromethyl and trifluoromethoxy;
- $R^2$ represents alkyl, hydroxyalkyl, alkoxyalkyl, cycloalkyl, monocyclic heteroaryl or phenyl optionally substituted once by a member of the group consisting of halogen, alkyl and alkoxy;
- one of $R^4$ and $R^5$ represents hydrogen or methyl and the other represents hydrogen;
- $R^6$ represents alkoxy of 1 to 3 carbon atoms;
- Y represents alkylene or phenylalkylene and Z represents —COOH.

More preferably, the compounds of formula $I_B$ will at least have one of the following characteristics:
- $R^1$ represents phenyl optionally substituted once by a substituent selected from the group consisting of halogen and methyl (and notably unsubstituted phenyl);
- $R^2$ represents hydroxyalkyl, alkoxyalkyl or cycloalkyl optionally substituted once (and preferably substituted once) by a member of the group consisting of hydroxy, hydroxymethyl, methoxymethyl, methoxy and ethoxy;
- $R^a$ represents hydrogen or fluorine and $R^b$ represents hydrogen (and notably $R^a$ represents hydrogen and $R^b$ represents hydrogen);
- each of $R^4$ and $R^5$ represents hydrogen;
- $R^6$ represents alkoxy of 3 to 4 carbon atoms (notably n-propoxy or n-butoxy and especially n-butoxy);
- Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

More preferably, the compounds of formula $I_{BP}$ will at least have one of the following characteristics:
- $R^1$ represents phenyl optionally substituted once by a substituent selected from the group consisting of halogen and methyl (and notably unsubstituted phenyl);
- $R^2$ represents hydroxyalkyl, alkoxyalkyl or cycloalkyl optionally substituted once (and preferably substituted once) by a member of the group consisting of hydroxy, hydroxymethyl, methoxymethyl, methoxy and ethoxy;
- each of $R^4$ and $R^5$ represents hydrogen;
- $R^6$ represents ethoxy;
- Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a second main embodiment of this invention, the compounds of formula I will be such that W represents —O—; such compounds will be collectively designated by "compounds of formula $I_O$" throughout the specification and claims. In such case, the compounds of formula $I_O$ will preferably be such that:
- $R^1$ represents phenyl optionally substituted once or twice by substituents each independently selected from the group consisting of halogen, methyl, methoxy, trifluoromethyl and trifluoromethoxy;
- $R^2$ represents alkyl, cycloalkyl, heterocyclyl or phenyl optionally substituted with one to three substituents each independently selected from the group consisting of halogen, alkyl and alkoxy;
- $R^a$ represents hydrogen or fluorine and $R^1$ represents hydrogen;
- $R^6$ represents alkoxy of 1 to 4 carbon atoms;
- Y represents alkylene or phenylalkylene and Z represents hydrogen, —OH, —COOH, tetrazolyl or —COOR$^7$, $R^7$ representing alkyl.

According to a variant of said second main embodiment of this invention, the compounds of formula I will be compounds of formula $I_P$ that are such that W represents —O—; such compounds will be collectively designated by "compounds of formula $I_{OP}$" throughout the specification and claims. In such case, the compounds of formula $I_{OP}$ will preferably be such that:
- $R^1$ represents phenyl optionally substituted once or twice by substituents each independently selected from the group consisting of halogen, methyl, methoxy, trifluoromethyl and trifluoromethoxy;
- $R^2$ represents alkyl, cycloalkyl, heterocyclyl or phenyl optionally substituted with one to three substituents each independently selected from the group consisting of halogen, alkyl and alkoxy;
- $R^6$ represents alkoxy of 1 to 4 carbon atoms;
- Y represents alkylene or phenylalkylene and Z represents —OH, —COOH, tetrazolyl or —COOR$^7$, $R^7$ representing alkyl.

Preferably, the compounds of formula $I_O$ will at least have one of the following characteristics:
- $R^1$ represents phenyl optionally substituted once by a substituent selected from the group consisting of halogen, methyl, methoxy, trifluoromethyl and trifluoromethoxy;
- $R^2$ represents cycloalkyl, heterocyclyl or phenyl;
- $R^a$ represents hydrogen or fluorine and $R^b$ represents hydrogen;
- one of $R^4$ and $R^5$ represents hydrogen or methyl and the other represents hydrogen;

$R^6$ represents alkoxy of 2 to 4 carbon atoms (especially n-propoxy or n-butoxy);

Y represents alkylene or phenylalkylene and Z represents —COOH.

Preferably, the compounds of formula $I_{OP}$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents cycloalkyl, heterocyclyl or phenyl; one of $R^4$ and $R^5$ represents hydrogen or methyl and the other represents hydrogen;

$R^6$ represents alkoxy of 1 to 3 carbon atoms;

Y represents alkylene or phenylalkylene and Z represents —COOH.

More preferably, the compounds of formula $I_O$ will at least have one of the following characteristics:

$R^1$ represents phenyl optionally substituted once by a substituent selected from the group consisting of halogen, methyl and methoxy (and notably unsubstituted phenyl);

$R^2$ represents cycloalkyl (in particular cyclopentyl) or heterocyclyl (in particular tetrahydrofuran-3-yl);

$R^a$ represents hydrogen or fluorine and $R^b$ represents hydrogen (and notably $R^a$ represents hydrogen and $R^b$ represents hydrogen);

each of $R^4$ and $R^5$ represents hydrogen;

$R^6$ represents alkoxy of 3 to 4 carbon atoms (notably n-propoxy or n-butoxy and especially n-butoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

More preferably, the compounds of formula $I_{OP}$ will at least have one of the following characteristics:

$R^1$ represents phenyl optionally substituted once by a substituent selected from the group consisting of halogen, methyl and methoxy (and notably unsubstituted phenyl);

$R^2$ represents cycloalkyl (in particular cyclopentyl) or heterocyclyl (in particular tetrahydrofuran-3-yl);

each of $R^4$ and $R^5$ represents hydrogen;

$R^6$ represents ethoxy;

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to a third main embodiment of this invention, the compounds of formula I will be such that W represents —S—; such compounds will be collectively designated by "compounds of formula $I_S$" throughout the specification and claims. In such case, the compounds of formula $I_S$ will preferably be such that:

$R^1$ represents phenyl optionally substituted once or twice by substituents each independently selected from the group consisting of halogen, methyl, methoxy, trifluoromethyl and trifluoromethoxy;

$R^2$ represents alkyl, cycloalkyl, heterocyclyl or phenyl optionally substituted with one to three substituents each independently selected from the group consisting of halogen, alkyl and alkoxy;

$R^a$ represents hydrogen or fluorine and $R^b$ represents hydrogen;

$R^6$ represents alkoxy of 1 to 4 carbon atoms;

Y represents alkylene or phenylalkylene and Z represents hydrogen, —OH, —COOH, tetrazolyl or —$COOR^7$, $R^7$ representing alkyl.

According to a variant of said third main embodiment of this invention, the compounds of formula I will be compounds of formula $I_P$ that are such that W represents —S—; such compounds will be collectively designated by "compounds of formula $I_{SP}$" throughout the specification and claims. In such case, the compounds of formula $I_{SP}$ will preferably be such that:

$R^1$ represents phenyl optionally substituted once or twice by substituents each independently selected from the group consisting of halogen, methyl, methoxy, trifluoromethyl and trifluoromethoxy;

$R^2$ represents alkyl, cycloalkyl, heterocyclyl or phenyl optionally substituted with one to three substituents each independently selected from the group consisting of halogen, alkyl and alkoxy;

$R^6$ represents alkoxy of 1 to 4 carbon atoms;

Y represents alkylene or phenylalkylene and Z represents —OH, —COOH, tetrazolyl or —$COOR^7$, $R^7$ representing alkyl.

Preferably, the compounds of formula $I_S$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents alkyl, cycloalkyl, heterocyclyl or phenyl;

$R^a$ represents hydrogen or fluorine and $R^b$ represents hydrogen;

one of $R^4$ and $R^5$ represents hydrogen or methyl and the other represents hydrogen;

$R^6$ represents alkoxy of 2 to 4 carbon atoms (especially n-propoxy or n-butoxy);

Y represents alkylene or phenylalkylene and Z represents —COOH.

Preferably, the compounds of formula $I_{SP}$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents alkyl, cycloalkyl, heterocyclyl or phenyl;

one of $R^4$ and $R^5$ represents hydrogen or methyl and the other represents hydrogen;

$R^6$ represents alkoxy of 1 to 3 carbon atoms;

Y represents alkylene or phenylalkylene and Z represents —COOH.

More preferably, the compounds of formula $I_S$ will at least have one of the following characteristics:

$R^1$ represents phenyl optionally substituted once by a substituent selected from the group consisting of halogen, methyl and methoxy (and notably unsubstituted phenyl);

$R^2$ represents alkyl or phenyl (and notably alkyl);

$R^a$ represents hydrogen or fluorine and $R^b$ represents hydrogen (and notably $R^a$ represents hydrogen and $R^b$ represents hydrogen);

each of $R^4$ and $R^5$ represents hydrogen;

$R^6$ represents alkoxy of 3 to 4 carbon atoms (notably n-propoxy or n-butoxy and especially n-butoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

More preferably, the compounds of formula $I_{SP}$ will at least have one of the following characteristics:

$R^1$ represents phenyl optionally substituted once by a substituent selected from the group consisting of halogen, methyl and methoxy (and notably unsubstituted phenyl);

$R^2$ represents alkyl or phenyl (and notably alkyl);

each of $R^4$ and $R^5$ represents hydrogen;

$R^6$ represents ethoxy;

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a fourth main embodiment of this invention, the compounds of formula I will be such that W represents —NR$^3$—; such compounds will be collectively designated by "compounds of formula I$_N$" throughout the specification and claims. In such case, the compounds of formula I$_N$ will preferably be such that:

- R$^1$ represents phenyl optionally substituted once or twice by substituents each independently selected from the group consisting of halogen, methyl, methoxy, trifluoromethyl and trifluoromethoxy;
- R$^2$ represents alkyl, hydroxyalkyl or alkoxyalkyl and R$^3$ represents hydrogen or alkyl; or
- R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy; or also
- R$^2$ and R$^3$ form, together with the nitrogen that carries them, an imidazolyl, pyrazolyl, 1,2,3-triazolyl or 1,2,4-triazolyl ring;
- R$^a$ represents hydrogen or fluorine and R$^b$ represents hydrogen;
- R$^6$ represents alkoxy of 1 to 4 carbon atoms;
- Y represents alkylene or phenylalkylene and Z represents hydrogen, —OH, —COOH, tetrazolyl or —COOR$^7$, R$^7$ representing alkyl.

According to a variant of said fourth main embodiment of this invention, the compounds of formula I will be compounds of formula I$_p$ that are such that W represents —NR$^3$—; such compounds will be collectively designated by "compounds of formula I$_{NP}$" throughout the specification and claims. In such case, the compounds of formula I$_{NP}$ will preferably be such that:

- R$^1$ represents phenyl optionally substituted once or twice by substituents each independently selected from the group consisting of halogen, methyl, methoxy, trifluoromethyl and trifluoromethoxy;
- R$^2$ represents alkyl, hydroxyalkyl or alkoxyalkyl and R$^3$ represents hydrogen or alkyl; or
- R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy; or also R$^2$ and R$^3$ form, together with the nitrogen that carries them, an imidazolyl, pyrazolyl, 1,2,3-triazolyl or 1,2,4-triazolyl ring;
- R$^6$ represents alkoxy of 1 to 4 carbon atoms;
- Y represents alkylene or phenylalkylene and Z represents —OH, —COOH, tetrazolyl or —COOR$^7$, R$^7$ representing alkyl.

Preferably, the compounds of formula I$_N$ will at least have one of the following characteristics:

- R$^1$ represents phenyl optionally substituted once by a substituent selected from the group consisting of halogen, methyl, methoxy, trifluoromethyl and trifluoromethoxy;
- R$^2$ represents alkyl or hydroxyalkyl and R$^3$ represents hydrogen or alkyl; or
- R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl, methoxy or ethoxy; or also
- R$^2$ and R$^3$ form, together with the nitrogen that carries them, an imidazolyl, pyrazolyl, 1,2,3-triazolyl or 1,2,4-triazolyl ring;
- R$^a$ represents hydrogen or fluorine and R$^b$ represents hydrogen; one of R$^4$ and R$^5$ represents hydrogen or methyl and the other represents hydrogen;
- R$^6$ represents alkoxy of 2 to 4 carbon atoms (especially n-propoxy or n-butoxy);
- Y represents alkylene or phenylalkylene and Z represents —COOH.

Preferably, the compounds of formula I$_{NP}$ will at least have one of the following characteristics:

- R$^1$ represents phenyl optionally substituted once by a substituent selected from the group consisting of halogen, methyl, methoxy, trifluoromethyl and trifluoromethoxy;
- R$^2$ represents alkyl or hydroxyalkyl and R$^3$ represents hydrogen or alkyl; or
- R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl, methoxy or ethoxy; or also
- R$^2$ and R$^3$ form, together with the nitrogen that carries them, an imidazolyl, pyrazolyl, 1,2,3-triazolyl or 1,2,4-triazolyl ring;
- one of R$^4$ and R$^5$ represents hydrogen or methyl and the other represents hydrogen;
- R$^6$ represents alkoxy of 1 to 3 carbon atoms;
- Y represents alkylene or phenylalkylene and Z represents —COOH.

More preferably, the compounds of formula I$_N$ will at least have one of the following characteristics:

- R$^1$ represents phenyl optionally substituted once by a substituent selected from the group consisting of halogen, methyl and methoxy (and notably unsubstituted phenyl);
- R$^2$ represents alkyl or hydroxyalkyl and R$^3$ represents hydrogen; or
- R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy or methoxy; or also
- R$^2$ and R$^3$ form, together with the nitrogen that carries them, a pyrazolyl ring;
- R$^a$ represents hydrogen or fluorine and R$^b$ represents hydrogen (and notably R$^a$ represents hydrogen and R$^b$ represents hydrogen);
- each of R$^4$ and R$^5$ represents hydrogen;
- R$^6$ represents alkoxy of 3 to 4 carbon atoms (notably n-propoxy or n-butoxy and especially n-butoxy);

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

More preferably, the compounds of formula I$_{NP}$ will at least have one of the following characteristics:
- R$^1$ represents phenyl optionally substituted once by a substituent selected from the group consisting of halogen, methyl and methoxy (and notably unsubstituted phenyl);
- R$^2$ represents alkyl or hydroxyalkyl and R$^3$ represents hydrogen; or
- R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy or methoxy; or also
- R$^2$ and R$^3$ form, together with the nitrogen that carries them, a pyrazolyl ring;
- each of R$^4$ and R$^5$ represents hydrogen;
- R$^6$ represents ethoxy;
- Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a variant of said fourth main embodiment, the compounds of formula I$_N$ will be such that the nitrogen atom of the —NR$^3$— radical is not member of a ring, i.e. such that R$^2$ represents alkyl, hydroxyalkyl or alkoxyalkyl; such compounds will be collectively designated by "compounds of formula I$_{NL}$" throughout the specification and claims.

According to a subvariant of said variant of said fourth main embodiment, the compounds of formula I$_N$ will be compounds of formula I$_{NP}$ that are such that the nitrogen atom of the —NR$^3$— radical is not member of a ring, i.e. such that R$^2$ represents alkyl, hydroxyalkyl or alkoxyalkyl; such compounds will be collectively designated by "compounds of formula I$_{NPL}$" throughout the specification and claims.

Preferably, the compounds of formula I$_{NL}$ will at least have one of the following characteristics:
- R$^1$ represents phenyl optionally substituted once by a substituent selected from the group consisting of halogen, methyl, methoxy, trifluoromethyl and trifluoromethoxy;
- R$^2$ represents alkyl or hydroxyalkyl and R$^3$ represents hydrogen or alkyl;
- R$^a$ represents hydrogen or fluorine and R$^b$ represents hydrogen;
- one of R$^4$ and R$^5$ represents hydrogen or methyl and the other represents hydrogen;
- R$^6$ represents alkoxy of 2 to 4 carbon atoms (especially n-propoxy or n-butoxy);
- Y represents alkylene or phenylalkylene and Z represents —COOH.

Preferably, the compounds of formula I$_{NPL}$ will at least have one of the following characteristics:
- R$^1$ represents phenyl optionally substituted once by a substituent selected from the group consisting of halogen, methyl, methoxy, trifluoromethyl and trifluoromethoxy;
- R$^2$ represents alkyl or hydroxyalkyl and R$^3$ represents hydrogen or alkyl;
- one of R$^4$ and R$^5$ represents hydrogen or methyl and the other represents hydrogen;
- R$^6$ represents alkoxy of 1 to 3 carbon atoms;
- Y represents alkylene or phenylalkylene and Z represents —COOH.

More preferably, the compounds of formula I$_{NL}$ will at least have one of the following characteristics:
- R$^1$ represents phenyl optionally substituted once by a substituent selected from the group consisting of halogen, methyl and methoxy (and notably unsubstituted phenyl);
- R$^2$ represents alkyl or hydroxyalkyl (and notably hydroxyalkyl) and R$^3$ represents hydrogen;
- R$^a$ represents hydrogen or fluorine and R$^b$ represents hydrogen (and notably R$^a$ represents hydrogen and R$^b$ represents hydrogen);
- each of R$^4$ and R$^5$ represents hydrogen;
- R$^6$ represents alkoxy of 3 to 4 carbon atoms (notably n-propoxy or n-butoxy and especially n-butoxy);
- Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

More preferably, the compounds of formula I$_{NPL}$ will at least have one of the following characteristics:
- R$^1$ represents phenyl optionally substituted once by a substituent selected from the group consisting of halogen, methyl and methoxy (and notably unsubstituted phenyl);
- R$^2$ represents alkyl or hydroxyalkyl (and notably hydroxyalkyl) and R$^3$ represents hydrogen;
- each of R$^4$ and R$^5$ represents hydrogen;
- R$^6$ represents ethoxy;
- Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to another variant of said fourth main embodiment, the compounds of formula I$_N$ will be such that the nitrogen atom of the —NR$^3$— radical is member of a ring, i.e. either such that R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy, or such that R$^2$ and R$^3$ form, together with the nitrogen that carries them, an imidazolyl, pyrazolyl, 1,2,3-triazolyl or 1,2,4-triazolyl ring, which ring is optionally substituted by a methyl group; such compounds will be collectively designated by "compounds of formula I$_{NR}$" throughout the specification and claims.

According to a subvariant of said other variant of said fourth main embodiment, the compounds of formula I$_N$ will be compounds of formula I$_{NP}$ that are such that the nitrogen atom of the —NR$^3$— radical is member of a ring, i.e. either such that R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy, or such that R$^2$ and R$^3$ form, together with the nitrogen that carries them, an imidazolyl, pyrazolyl, 1,2,3-triazolyl or 1,2,4-triazolyl ring, which ring is optionally substituted by a methyl group; such compounds will be collectively designated by "compounds of formula I$_{NPR}$" throughout the specification and claims.

Preferably, the compounds of formula I$_{NR}$ will at least have one of the following characteristics:

R$^1$ represents phenyl optionally substituted once by a substituent selected from the group consisting of halogen, methyl, methoxy, trifluoromethyl and trifluoromethoxy;

R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy; or R$^2$ and R$^3$ form, together with the nitrogen that carries them, an imidazolyl, pyrazolyl, 1,2,3-triazolyl or 1,2,4-triazolyl ring;

R$^a$ represents hydrogen or fluorine and R$^b$ represents hydrogen;

one of R$^4$ and R$^5$ represents hydrogen or methyl and the other represents hydrogen;

R$^6$ represents alkoxy of 2 to 4 carbon atoms (especially n-propoxy or n-butoxy);

Y represents alkylene or phenylalkylene and Z represents hydrogen or —COOH.

Preferably, the compounds of formula I$_{NPR}$ will at least have one of the following characteristics:

R$^1$ represents phenyl optionally substituted once by a substituent selected from the group consisting of halogen, methyl, methoxy, trifluoromethyl and trifluoromethoxy;

R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy; or R$^2$ and R$^3$ form, together with the nitrogen that carries them, an imidazolyl, pyrazolyl, 1,2,3-triazolyl or 1,2,4-triazolyl ring;

one of R$^4$ and R$^5$ represents hydrogen or methyl and the other represents hydrogen;

R$^6$ represents alkoxy of 1 to 3 carbon atoms;

Y represents alkylene or phenylalkylene and Z represents —COOH.

More preferably, the compounds of formula I$_{NR}$ will at least have one of the following characteristics:

R$^1$ represents phenyl optionally substituted once by a substituent selected from the group consisting of halogen, methyl and methoxy (and notably unsubstituted phenyl);

R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl, methoxy or ethoxy (and in particular hydroxy or methoxy); or R$^2$ and R$^3$ form, together with the nitrogen that carries them, an imidazolyl, pyrazolyl, 1,2,3-triazolyl or 1,2,4-triazolyl ring (and in particular a pyrazolyl ring);

R$^a$ represents hydrogen or fluorine and R$^b$ represents hydrogen;

each of R$^4$ and R$^5$ represents hydrogen;

R$^6$ represents alkoxy of 3 to 4 carbon atoms (notably n-propoxy or n-butoxy and especially n-butoxy);

Y represents alkylene (preferably —CH$_2$—, —CH$_2$—CH$_2$— or —CH$_2$—CH$_2$—CH$_2$— and more preferably —CH$_2$—CH$_2$—) and Z represents hydrogen or —COOH (preferably —COOH).

More preferably, the compounds of formula I$_{NPR}$ will at least have one of the following characteristics:

R$^1$ represents phenyl optionally substituted once by a substituent selected from the group consisting of halogen, methyl and methoxy (and notably unsubstituted phenyl);

R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl, methoxy or ethoxy (and in particular hydroxy or methoxy); or R$^2$ and R$^3$ form, together with the nitrogen that carries them, an imidazolyl, pyrazolyl, 1,2,3-triazolyl or 1,2,4-triazolyl ring (and in particular a pyrazolyl ring);

each of R$^4$ and R$^5$ represents hydrogen;

R$^6$ represents ethoxy;

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

Especially preferred compounds of formula I$_{NR}$ will be such that they will at least have one of the following characteristics:

R$^1$ represents phenyl optionally substituted once by a substituent selected from the group consisting of halogen, methyl and methoxy (and notably unsubstituted phenyl);

R$^2$ and R$^3$ form, together with the nitrogen that carries them, a heterocyclic ring of 4 to 6 members wherein the members needed to complete said heterocyclic ring are each independently selected from —CH$_2$— and —CHR$^x$—, it being understood however that said heterocyclic ring does not contain more than one —CHR$^x$— member, R$^x$ representing methoxy or ethoxy, and in particular methoxy (and notably R$^2$ and R$^3$ form, together with the nitrogen that carries them, 3-methoxy-pyrrolidin-1-yl, especially (S)-3-methoxy-pyrrolidin-1-yl);

each of R$^a$ and R$^b$ represents hydrogen;

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH;

each of R$^4$ and R$^5$ represents hydrogen;

R$^6$ represents alkoxy of 2 to 4 carbon atoms (and preferably alkoxy of 3 to 4 carbon atoms, notably n-propoxy or n-butoxy and especially n-butoxy).

Other especially preferred compounds of formula I$_{NR}$ will be such that they will at least have one of the following characteristics:

R$^1$ represents phenyl optionally substituted once by a substituent selected from the group consisting of halogen, methyl and methoxy (and notably unsubstituted phenyl);

R$^2$ and R$^3$ form, together with the nitrogen that carries them, a heterocyclic ring of 4 to 6 members wherein the members needed to complete said heterocyclic ring are each independently selected from —CH$_2$— and —CHR$^x$—, it being understood however that said heterocyclic ring does not contain more than one —CHR$^x$— member, R$^x$ representing methoxy or ethoxy, and in particular methoxy (and notably $R^2$ and $R^3$ form, together with the nitrogen that carries them, 3-methoxy-pyrrolidin-1-yl, especially (S)-3-methoxy-pyrrolidin-1-yl);

$R^a$ represents fluorine and $R^b$ represents hydrogen;

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH;

each of $R^4$ and $R^5$ represents hydrogen;

$R^6$ represents alkoxy of 2 to 4 carbon atoms (and preferably alkoxy of 3 to 4 carbon atoms, notably n-propoxy or n-butoxy and especially n-butoxy).

According to a fifth main embodiment of this invention, the compounds of formula I will be such that W represents —C≡C—; such compounds will be collectively designated by "compounds of formula $I_T$" throughout the specification and claims. In such case, the compounds of formula $I_T$ will preferably be such that:

$R^1$ represents phenyl optionally substituted once or twice by substituents each independently selected from the group consisting of halogen, methyl, methoxy, trifluoromethyl and trifluoromethoxy;

$R^2$ represents hydroxyalkyl or alkoxyalkyl;

$R^6$ represents alkoxy of 1 to 4 carbon atoms;

Y represents alkylene or phenylalkylene and Z represents hydrogen, —OH, —COOH, tetrazolyl or —COOR$^7$, $R^7$ representing alkyl.

According to a variant of said fifth main embodiment of this invention, the compounds of formula I will be compounds of formula $I_P$ that are such that W represents —C≡C—; such compounds will be collectively designated by "compounds of formula $I_{TP}$" throughout the specification and claims. In such case, the compounds of formula $I_{TP}$ will preferably be such that:

$R^1$ represents phenyl optionally substituted once or twice by substituents each independently selected from the group consisting of halogen, methyl, methoxy, trifluoromethyl and trifluoromethoxy;

$R^2$ represents hydroxyalkyl or alkoxyalkyl;

$R^6$ represents alkoxy of 1 to 4 carbon atoms;

Y represents alkylene or phenylalkylene and Z represents —OH, —COOH, tetrazolyl or —COOR$^7$, $R^7$ representing alkyl.

Preferably, the compounds of formula $I_T$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents hydroxyalkyl;

$R^a$ represents hydrogen or fluorine and $R^b$ represents hydrogen; one of $R^4$ and $R^5$ represents hydrogen or methyl and the other represents hydrogen;

$R^6$ represents alkoxy of 2 to 4 carbon atoms (especially n-propoxy or n-butoxy);

Y represents alkylene or phenylalkylene and Z represents —COOH.

Preferably, the compounds of formula $I_{TP}$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents hydroxyalkyl; one of $R^4$ and $R^5$ represents hydrogen or methyl and the other represents hydrogen;

$R^6$ represents alkoxy of 1 to 3 carbon atoms;

Y represents alkylene or phenylalkylene and Z represents —COOH.

More preferably, the compounds of formula $I_T$ will at least have one of the following characteristics:

$R^1$ represents phenyl optionally substituted once by a substituent selected from the group consisting of halogen, methyl and methoxy (and notably unsubstituted phenyl);

$R^2$ represents hydroxyalkyl of 1 to 4 carbon atoms (and notably 1-hydroxy-1-methyl-ethyl);

$R^a$ represents hydrogen or fluorine and $R^b$ represents hydrogen (and notably $R^a$ represents hydrogen and $R^b$ represents hydrogen);

each of $R^4$ and $R^5$ represents hydrogen;

$R^6$ represents alkoxy of 3 to 4 carbon atoms (notably n-propoxy or n-butoxy and especially n-butoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

More preferably, the compounds of formula $I_{TP}$ will at least have one of the following characteristics:

$R^1$ represents phenyl optionally substituted once by a substituent selected from the group consisting of halogen, methyl and methoxy (and notably unsubstituted phenyl);

$R^2$ represents hydroxyalkyl of 1 to 4 carbon atoms (and notably 1-hydroxy-1-methyl-ethyl);

each of $R^4$ and $R^5$ represents hydrogen;

$R^6$ represents ethoxy;

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to a sixth main embodiment of this invention, the compounds of formula I will be such that $R^a$ represents fluorine; such compounds will be collectively designated by "compounds of formula $I_F$" throughout the specification and claims. In such case, the compounds of formula $I_F$ will preferably be such that:

$R^1$ represents phenyl optionally substituted once by fluorine, methyl or methoxy;

$R^6$ represents alkoxy of 2 to 4 carbon atoms;

Y represents alkylene or phenylalkylene and Z represents hydrogen, —OH, —COOH, tetrazolyl or —COOR$^7$, $R^7$ representing alkyl.

Preferably, the compounds of formula $I_F$ will at least have one of the following characteristics:

$R^1$ represents phenyl optionally substituted once by fluorine, methyl or methoxy;

W represents —NR$^3$— and $R^2$ and $R^3$ form, together with the nitrogen that carries them, a heterocyclic ring of 4 to 7 members wherein the members needed to complete said heterocyclic ring are each independently selected from —$CH_2$— and —CHR$^x$—, it being understood however that said heterocyclic ring does not contain more than one —CHR$^x$— member, R$^x$ representing hydroxy, hydroxymethyl, alkoxymethyl or alkoxy, or W represents —NR$^3$— and $R^2$ and $R^3$ form, together with the nitrogen that carries them, an imidazolyl, pyrazolyl, 1,2,3-triazolyl or 1,2,4-triazolyl ring, which ring is optionally substituted by a methyl group;

one of $R^4$ and $R^5$ represents hydrogen or methyl and the other represents hydrogen;

$R^6$ represents alkoxy of 2 to 4 carbon atoms (especially n-propoxy or n-butoxy);

Y represents alkylene or phenylalkylene and Z represents —COOH.

More preferably, the compounds of formula $I_F$ will at least have one of the following characteristics:

R¹ represents phenyl optionally substituted once by fluorine, methyl or methoxy (especially unsubstituted phenyl);

W represents —NR³— and R² and R³ form, together with the nitrogen that carries them, a heterocyclic ring of 4 to 6 members wherein the members needed to complete said heterocyclic ring are each independently selected from —CH$_2$— and —CHR$^x$—, it being understood however that said heterocyclic ring does not contain more than one —CHR$^x$— member, R$^x$ representing methoxy or ethoxy, and in particular methoxy (and notably R² and R³ form, together with the nitrogen that carries them, 3-methoxy-pyrrolidin-1-yl, especially (S)-3-methoxy-pyrrolidin-1-yl);

each of R⁴ and R⁵ represents hydrogen;

R⁶ represents alkoxy of 3 to 4 carbon atoms (notably n-propoxy or n-butoxy and especially n-butoxy);

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a seventh main embodiment of this invention, the compounds of formula I will be such that R$^a$ represents hydrogen and R$^b$ represents alkoxy; such compounds will be collectively designated by "compounds of formula I$_A$" throughout the specification and claims. In such case, the compounds of formula I$_A$ will preferably be such that:

R¹ represents phenyl optionally substituted once or twice by substituents each independently selected from the group consisting of halogen, methyl, methoxy, trifluoromethyl and trifluoromethoxy;

R⁶ represents alkoxy of 2 to 4 carbon atoms;

Y represents alkylene or phenylalkylene and Z represents hydrogen, —OH, —COOH, tetrazolyl or —COOR⁷, R⁷ representing alkyl.

Preferably, the compounds of formula I$_A$ will at least have one of the following characteristics:

R¹ represents phenyl optionally substituted once by halogen, methyl, methoxy, trifluoromethyl and trifluoromethoxy;

W represents a bond and R² represents cycloalkyl of 3 to 6 carbon atoms which may be substituted once by hydroxy, hydroxymethyl, alkoxymethyl (preferably methoxymethyl or ethoxymethyl and more preferably methoxymethyl) or alkoxy (preferably methoxy or ethoxy and more preferably methoxy);

one of R⁴ and R⁵ represents hydrogen or methyl and the other represents hydrogen;

R⁶ represents alkoxy of 2 to 4 carbon atoms (especially n-propoxy or n-butoxy);

Y represents alkylene or phenylalkylene and Z represents —COOH.

More preferably, the compounds of formula I$_A$ will at least have one of the following characteristics:

R¹ represents phenyl optionally substituted once by fluorine, methyl or methoxy (especially unsubstituted phenyl);

W represents a bond and R² represents cyclopropyl which may be substituted once by hydroxy, hydroxymethyl, methoxymethyl, ethoxymethyl, methoxy or ethoxy (and in particular unsubstituted cyclopropyl);

R$^b$ represents methoxy;

each of R⁴ and R⁵ represents hydrogen;

R⁶ represents alkoxy of 3 to 4 carbon atoms (notably n-propoxy or n-butoxy and especially n-butoxy);

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

Besides, in a general manner, the side chain Y—Z of the compounds of formula I will preferably represent alkyl of 1 to 4 carbon atoms, hydroxyalkyl wherein the alkyl is an alkyl of 1 to 4 carbon atoms, carboxyalkyl wherein the alkyl is an alkyl of 1 to 4 carbon atoms, cyanoalkyl wherein the alkyl is an alkyl of 1 to 4 carbon atoms, tetrazolylalkyl wherein the alkyl is an alkyl of 1 to 4 carbon atoms or (4-carboxy-phenyl)alkyl. More preferably, in a general manner, the side chain Y—Z of the compounds of formula I will represent alkyl of 1 to 4 carbon atoms, hydroxyalkyl wherein the alkyl is an alkyl of 1 to 4 carbon atoms, carboxyalkyl wherein the alkyl is an alkyl of 1 to 4 carbon atoms, tetrazolylalkyl wherein the alkyl is an alkyl of 1 to 4 carbon atoms or (4-carboxy-phenyl)alkyl. Even more preferably, in a general manner, the side chain Y—Z of the compounds of formula I will be selected from the group consisting of iso-propyl, hydroxymethyl, carboxymethyl, 2-carboxy-ethyl, 3-carboxy-propyl, 2H-tetrazol-5-yl-methyl and (4-carboxy-phenyl)methyl (especially from the group consisting of iso-propyl, hydroxymethyl, 2-carboxy-ethyl, 2H-tetrazol-5-yl-methyl and (4-carboxy-phenyl)methyl).

The following compounds of formula I are especially preferred:

4-{(S)-4-carboxy-2-[(4-chloro-6-phenyl-pyridine-2-carbonyl)-amino]-butyryl}-piperazine-1-carboxylic acid ethyl ester;

4-{(S)-4-carboxy-2-[(6-chloro-4-phenyl-pyridine-2-carbonyl)-amino]-butyryl}-piperazine-1-carboxylic acid ethyl ester;

4-{(S)-4-carboxy-2-[(4-cyclopentyloxy-6-phenyl-pyridine-2-carbonyl)-amino]-butyryl}-piperazine-1-carboxylic acid ethyl ester;

4-((S)-4-carboxy-2-{[4-(1-hydroxy-1-methyl-ethyl)-6-phenyl-pyridine-2-carbonyl]-amino}-butyryl)-piperazine-1-carboxylic acid ethyl ester;

4-{(S)-4-carboxy-2-[(4,6-diphenyl-pyridine-2-carbonyl)-amino]-butyryl}-piperazine-1-carboxylic acid ethyl ester;

4-{(S)-4-carboxy-2-[(6-phenyl-4-pyrazol-1-yl-pyridine-2-carbonyl)-amino]-butyryl}-piperazine-1-carboxylic acid ethyl ester;

4-((S)-4-carboxy-2-{[4-(4-methoxy-phenyl)-6-phenyl-pyridine-2-carbonyl]-amino}-butyryl)-piperazine-1-carboxylic acid ethyl ester;

4-((S)-4-carboxy-2-{[4-cyclopropyl-6-phenyl-pyridine-2-carbonyl]-amino}-butyryl)-piperazine-1-carboxylic acid ethyl ester;

4-{(S)-2-[(4-butyl-6-phenyl-pyridine-2-carbonyl)-amino]-4-carboxy-butyryl}-piperazine-1-carboxylic acid ethyl ester;

4-((S)-4-carboxy-2-{[6-(2-fluoro-phenyl)-4-phenyl-pyridine-2-carbonyl]-amino}-butyryl)-piperazine-1-carboxylic acid ethyl ester;

4-((S)-4-carboxy-2-{[6-(4-fluoro-phenyl)-4-phenyl-pyridine-2-carbonyl]-amino}-butyryl)-piperazine-1-carboxylic acid ethyl ester;

4-{(S)-4-carboxy-2-[(4-phenyl-6-o-tolyl-pyridine-2-carbonyl)-amino]-butyryl}-piperazine-1-carboxylic acid ethyl ester;

4-{(S)-4-carboxy-2-[(4-phenyl-6-p-tolyl-pyridine-2-carbonyl)-amino]-butyryl}-piperazine-1-carboxylic acid ethyl ester;

4-((S)-4-carboxy-2-{[4-((R)-3-hydroxy-pyrrolidin-1-yl)-6-phenyl-pyridine-2-carbonyl]-amino}-butyryl)-piperazine-1-carboxylic acid ethyl ester;

4-{(S)-4-carboxy-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester;

4-{(S)-4-carboxy-2-[(6-phenyl-4-pyrrolidin-1-yl-pyridine-2-carbonyl)-amino]-butyryl}-piperazine-1-carboxylic acid ethyl ester;

4-((S)-4-carboxy-2-{[4-(2-hydroxy-ethylamino)-6-phenyl-pyridine-2-carbonyl]-amino}-butyryl)-piperazine-1-carboxylic acid ethyl ester;

4-((S)-4-carboxy-2-{[4-((S)-3-methoxy-pyrrolidin-1-yl)-6-phenyl-pyridine-2-carbonyl]-amino}-butyryl)-piperazine-1-carboxylic acid ethyl ester;

4-{(S)-4-carboxy-2-[(4-isopropylamino-6-phenyl-pyridine-2-carbonyl)-amino]-butyryl}-piperazine-1-carboxylic acid ethyl ester;

4-((S)-4-carboxy-2-{[4-(2-methoxymethyl-cyclopropyl)-6-phenyl-pyridine-2-carbonyl]-amino}-butyryl)-piperazine-1-carboxylic acid ethyl ester;

4-((S)-4-carboxy-2-{[4-(2-hydroxymethyl-cyclopropyl)-6-phenyl-pyridine-2-carbonyl]-amino}-butyryl)-piperazine-1-carboxylic acid ethyl ester;

4-{(S)-3-cyano-2-[(4,6-diphenyl-pyridine-2-carbonyl)-amino]-propionyl}-piperazine-1-carboxylic acid ethyl ester;

4-{(S)-4-carboxy-2-[(4,6-diphenyl-pyridine-2-carbonyl)-amino]-butyryl}-3-methyl-piperazine-1-carboxylic acid ethyl ester;

4-{(S)-2-[(4,6-diphenyl-pyridine-2-carbonyl)-amino]-3-hydroxy-propionyl}-piperazine-1-carboxylic acid ethyl ester;

4-{(S)-4-carboxy-2-[(4-phenyl-6-pyrazol-1-yl-pyridine-2-carbonyl)-amino]-butyryl}-piperazine-1-carboxylic acid ethyl ester;

4-((S)-4-carboxy-2-{[4-(3-hydroxy-propyl)-6-phenyl-pyridine-2-carbonyl]-amino}-butyryl)-piperazine-1-carboxylic acid ethyl ester;

4-((S)-4-carboxy-2-{[4-(3-hydroxy-3-methyl-butyl)-6-phenyl-pyridine-2-carbonyl]-amino}-butyryl)-piperazine-1-carboxylic acid ethyl ester;

4-((S)-4-carboxy-2-{[4-(3-hydroxy-3-methyl-butyl)-6-phenyl-pyridine-2-carbonyl]-amino}-butyryl)-piperazine-1-carboxylic acid ethyl ester;

4-((S)-4-carboxy-2-{[4-(4-hydroxy-cyclohexyl)-6-phenyl-pyridine-2-carbonyl]-amino}-butyryl)-piperazine-1-carboxylic acid ethyl ester;

4-{(S)-4-carboxy-2-[(6-phenyl-4-phenylsulfanyl-pyridine-2-carbonyl)-amino]-butyryl}-piperazine-1-carboxylic acid ethyl ester;

4-((S)-4-carboxy-2-{[4-(2-hydroxy-cyclohexyl)-6-phenyl-pyridine-2-carbonyl]-amino}-butyryl)-piperazine-1-carboxylic acid ethyl ester;

4-{(S)-4-carboxy-2-[(6-phenyl-4-thiophen-3-yl-pyridine-2-carbonyl)-amino]-butyryl}-piperazine-1-carboxylic acid ethyl ester;

4-{(S)-4-carboxy-2-[(4-furan-3-yl-6-phenyl-pyridine-2-carbonyl)-amino]-butyryl}-piperazine-1-carboxylic acid ethyl ester;

4-{(S)-4-carboxy-2-[(4-isopropylsulfanyl-6-phenyl-pyridine-2-carbonyl)-amino]-butyryl}-piperazine-1-carboxylic acid ethyl ester;

4-(S)-3-(4-carboxy-phenyl)-2-{[4-(2-methoxymethyl-cyclopropyl)-6-phenyl-pyridine-2-carbonyl]-amino}-propionyl)-piperazine-1-carboxylic acid ethyl ester;

4-{(S)-4-carboxy-2-[(4-methyl-6-phenyl-pyridine-2-carbonyl)-amino]-butyryl}-piperazine-1-carboxylic acid ethyl ester;

4-((S)-4-carboxy-2-{[6-phenyl-4-(tetrahydro-furan-3-yloxy)-pyridine-2-carbonyl]-amino}-butyryl)-piperazine-1-carboxylic acid ethyl ester;

4-{(S)-4-carboxy-2-[(6-phenyl-pyridine-2-carbonyl)-amino]-butyryl}-piperazine-1-carboxylic acid ethyl ester;

4-{(S)-4-O-tert-butoxycarbonyl-2-[(4-chloro-6-phenyl-pyridine-2-carbonyl)-amino]-butyryl}-piperazine-1-carboxylic acid ethyl ester;

4-{(S)-4-tert-butoxycarbonyl-2-[(4-cyclopentyloxy-6-phenyl-pyridine-2 carbonyl)-amino]-butyryl}-piperazine-1-carboxylic acid ethyl ester;

4-((S)-4-tert-butoxycarbonyl-2-{[4-(1-hydroxy-1-methyl-ethyl)-6-phenyl-pyridine-2-carbonyl]-amino}-butyryl)-piperazine-1-carboxylic acid ethyl ester;

4-{(S)-4-tert-butoxycarbonyl-2-[(4,6-diphenyl-pyridine-2-carbonyl)-amino]-butyryl}-piperazine-1-carboxylic acid ethyl ester;

4-{(S)-4-tert-butoxycarbonyl-2-[(6-phenyl-4-pyrazol-1-yl-pyridine-2-carbonyl)-amino]-butyryl}-piperazine-1-carboxylic acid ethyl ester;

4-((S)-4-tert-butoxycarbonyl-2-{[4-(4-methoxy-phenyl)-6-phenyl-pyridine-2-carbonyl]-amino}-butyryl)-piperazine-1-carboxylic acid ethyl ester;

4-((S)-4-tert-butoxycarbonyl-2-{[4-cyclopropyl-6-phenyl-pyridine-2-carbonyl]-amino}-butyryl)-piperazine-1-carboxylic acid ethyl ester;

4-{(S)-4-tert-butoxycarbonyl-2-[(4-butyl-6-phenyl-pyridine-2-carbonyl)-amino]-butyryl}-piperazine-1-carboxylic acid ethyl ester;

4-{(S)-4-O-tert-butoxycarbonyl-2-[(4-[(R)-3-hydroxy-pyrrolidin-1-yl]-6-phenyl-pyridine-2-carbonyl)-amino]-butyryl}-piperazine-1-carboxylic acid ethyl ester;

4-{(S)-4-tert-butoxycarbonyl-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester;

4-{(S)-4-tert-butoxycarbonyl-2-[(6-phenyl-4-pyrrolidin-1-yl-pyridine-2-carbonyl)-amino]-butyryl}-piperazine-1-carboxylic acid ethyl ester;

4-((S)-4-tert-butoxycarbonyl-2-{[4-(2-hydroxy-ethylamino)-6-phenyl-pyridine-2-carbonyl]-amino}-butyryl)-piperazine-1-carboxylic acid ethyl ester;

4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid ethyl ester;

4-{(S)-4-tert-butoxycarbonyl-2-[(4-isopropylamino-6-phenyl-pyridine-2-carbonyl)-amino]-butyryl}-piperazine-1-carboxylic acid ethyl ester;

4-((S)-4-tert-butoxycarbonyl-2-{[4-(2-methoxymethyl-cyclopropyl)-6-phenyl-pyridine-2-carbonyl]-amino}-butyryl)-piperazine-1-carboxylic acid ethyl ester;

4-((S)-4-tert-butoxycarbonyl-2-{[4-(2-hydroxymethyl-cyclopropyl)-6-phenyl-pyridine-2-carbonyl]-amino}-butyryl)-piperazine-1-carboxylic acid ethyl ester;

4-{(S)-4-tert-butoxycarbonyl-2-[(4,6-diphenyl-pyridine-2-carbonyl)-amino]-butyryl}-3-methyl-piperazine-1-carboxylic acid ethyl ester;

4-{(S)-4-tert-butoxycarbonyl-2-[(4-phenyl-6-pyrazol-1-yl-pyridine-2-carbonyl)-amino]-butyryl}-piperazine-1-carboxylic acid ethyl ester;

4-((S)-4-tert-butoxycarbonyl-2-{[4-(3-hydroxy-propyl)-6-phenyl-pyridine-2-carbonyl]-amino}-butyryl)-piperazine-1-carboxylic acid ethyl ester;

4-((S)-4-tert-butoxycarbonyl-2-{[4-(3-hydroxy-3-methyl-but-1-ynyl)-6-phenyl-pyridine-2-carbonyl]-amino}-butyryl)-piperazine-1-carboxylic acid ethyl ester;

4-((S)-4-tert-butoxycarbonyl-2-{[4-(3-hydroxy-3-methyl-butyl)-6-phenyl-pyridine-2-carbonyl]-amino}-butyryl)-piperazine-1-carboxylic acid ethyl ester;

4-{(S)-4-tert-butoxycarbonyl-2-[(6-phenyl-4-phenylsulfanyl-pyridine-2-carbonyl)-amino]-butyryl}-piperazine-1-carboxylic acid ethyl ester;

4-{(S)-4-tert-butoxycarbonyl-2-[(6-phenyl-4-thiophen-3-yl-pyridine-2-carbonyl)-amino]-butyryl}-piperazine-1-carboxylic acid ethyl ester;

4-{(S)-4-tert-butoxycarbonyl-2-[(4-furan-3-yl-6-phenyl-pyridine-2-carbonyl)-amino]-butyryl}-piperazine-1-carboxylic acid ethyl ester;

4-{(S)-4-tert-butoxycarbonyl-2-[(4-isopropylsulfanyl-6-phenyl-pyridine-2-carbonyl)-amino]-butyryl}-piperazine-1-carboxylic acid ethyl ester;

4-((S)-3-(4-tert-butoxycarbonyl-phenyl)-2-{[4-(2-methoxymethyl-cyclopropyl)-6-phenyl-pyridine-2-carbonyl]-amino}-propionyl)-piperazine-1-carboxylic acid ethyl ester;

4-{(S)-4-tert-butoxycarbonyl-2-[(6-phenyl-pyridine-2-carbonyl)-amino]-butyryl}-piperazine-1-carboxylic acid ethyl ester;

4-[(S)-2-[(4,6-diphenyl-pyridine-2-carbonyl)-amino]-3-(2H-tetrazol-5-yl)-propionyl]-piperazine-1-carboxylic acid ethyl ester;

4-((S)-4-carboxy-2-{[4-((S)-3-methoxy-pyrrolidin-1-yl)-6-phenyl-pyridine-2-carbonyl]-amino}-butyryl)-piperazine-1-carboxylic acid butyl ester;

4-((S)-3-hydroxy-2-{[4-((S)-3-methoxy-pyrrolidin-1-yl)-6-phenyl-pyridine-2-carbonyl]-amino}-propionyl)-piperazine-1-carboxylic acid butyl ester;

4-((S)-2-{[4-((S)-3-methoxy-pyrrolidin-1-yl)-6-phenyl-pyridine-2-carbonyl]-amino}-3-methyl-butyryl)-piperazine-1-carboxylic acid butyl ester;

4-((S)-4-carboxy-2-{[5-fluoro-4-((S)-3-methoxy-pyrrolidin-1-yl)-6-phenyl-pyridine-2-carbonyl]-amino}-butyryl)-piperazine-1-carboxylic acid butyl ester;

4-{(S)-4-carboxy-2-[(4-cyclopropyl-3-methoxy-6-phenyl-pyridine-2-carbonyl)-amino]-butyryl}-piperazine-1-carboxylic acid ethyl ester;

4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid butyl ester;

4-((S)-4-tert-butoxycarbonyl-2-{[5-fluoro-4-(3-methoxy-pyrrolidin-1-yl)-6-phenyl-pyridine-2-carbonyl]-amino}-butyryl)-piperazine-1-carboxylic acid butyl ester;

4-{(S)-4-tert-butoxycarbonyl-2-[(4-cyclopropyl-3-methoxy-6-phenyl-pyridine-2-carbonyl)-amino]-butyryl}-piperazine-1-carboxylic acid ethyl ester;

4-{(S)-2-[(4-butylamino-5-fluoro-6-phenyl-pyridine-2-carbonyl)-amino]-4-carboxy-butyryl}-piperazine-1-carboxylic acid ethyl ester;

4-{(S)-2-[(4-butylamino-5-fluoro-6-phenyl-pyridine-2-carbonyl)-amino]-4-carboxy-butyryl}-piperazine-1-carboxylic acid butyl ester;

4-{(S)-4-tert-butoxycarbonyl-2-[(4-chloro-5-fluoro-6-phenyl-pyridine-2-carbonyl)-amino]-butyryl}-piperazine-1-carboxylic acid ethyl ester;

4-{(S)-4-tert-butoxycarbonyl-2-[(4-chloro-5-fluoro-6-phenyl-pyridine-2-carbonyl)-amino]-butyryl}-piperazine-1-carboxylic acid butyl ester; as well as the salts thereof (in particular the pharmaceutically acceptable salts thereof).

The following compounds of formula $I_p$ are especially preferred:

4-{(S)-4-carboxy-2-[(4-chloro-6-phenyl-pyridine-2-carbonyl)-amino]-butyryl}-piperazine-1-carboxylic acid ethyl ester;

4-{(S)-4-carboxy-2-[(6-chloro-4-phenyl-pyridine-2-carbonyl)-amino]-butyryl}-piperazine-1-carboxylic acid ethyl ester;

4-{(S)-4-carboxy-2-[(4-cyclopentyloxy-6-phenyl-pyridine-2-carbonyl)-amino]-butyryl}-piperazine-1-carboxylic acid ethyl ester;

4-((S)-4-carboxy-2-{[4-(1-hydroxy-1-methyl-ethyl)-6-phenyl-pyridine-2-carbonyl]-amino}-butyryl)-piperazine-1-carboxylic acid ethyl ester;

4-{(S)-4-carboxy-2-[(4,6-diphenyl-pyridine-2-carbonyl)-amino]-butyryl}-piperazine-1-carboxylic acid ethyl ester;

4-{(S)-4-carboxy-2-[(6-phenyl-4-pyrazol-1-yl-pyridine-2-carbonyl)-amino]-butyryl}-piperazine-1-carboxylic acid ethyl ester;

4-((S)-4-carboxy-2-{[4-(4-methoxy-phenyl)-6-phenyl-pyridine-2-carbonyl]-amino}-butyryl)-piperazine-1-carboxylic acid ethyl ester;

4-((S)-4-carboxy-2-{[4-cyclopropyl-6-phenyl-pyridine-2-carbonyl]-amino}-butyryl)-piperazine-1-carboxylic acid ethyl ester;

4-{(S)-2-[(4-butyl-6-phenyl-pyridine-2-carbonyl)-amino]-4-carboxy-butyryl}-piperazine-1-carboxylic acid ethyl ester;

4-((S)-4-carboxy-2-{[6-(2-fluoro-phenyl)-4-phenyl-pyridine-2-carbonyl]-amino}-butyryl)-piperazine-1-carboxylic acid ethyl ester;

4-((S)-4-carboxy-2-{[6-(4-fluoro-phenyl)-4-phenyl-pyridine-2-carbonyl]-amino}-butyryl)-piperazine-1-carboxylic acid ethyl ester;

4-{(S)-4-carboxy-2-[(4-phenyl-6-o-tolyl-pyridine-2-carbonyl)-amino]-butyryl}-piperazine-1-carboxylic acid ethyl ester;

4-{(S)-4-carboxy-2-[(4-phenyl-6-p-tolyl-pyridine-2-carbonyl)-amino]-butyryl}-piperazine-1-carboxylic acid ethyl ester;

4-((S)-4-carboxy-2-{[4-((R)-3-hydroxy-pyrrolidin-1-yl)-6-phenyl-pyridine-2-carbonyl]-amino}-butyryl)-piperazine-1-carboxylic acid ethyl ester;

4-{(S)-4-carboxy-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester;

4-{(S)-4-carboxy-2-[(6-phenyl-4-pyrrolidin-1-yl-pyridine-2-carbonyl)-amino]-butyryl}-piperazine-1-carboxylic acid ethyl ester;

4-((S)-4-carboxy-2-{[4-(2-hydroxy-ethylamino)-6-phenyl-pyridine-2-carbonyl]-amino}-butyryl)-piperazine-1-carboxylic acid ethyl ester;

4-((S)-4-carboxy-2-{[4-((S)-3-methoxy-pyrrolidin-1-yl)-6-phenyl-pyridine-2-carbonyl]-amino}-butyryl)-piperazine-1-carboxylic acid ethyl ester;

4-{(S)-4-carboxy-2-[(4-isopropylamino-6-phenyl-pyridine-2-carbonyl)-amino]-butyryl}-piperazine-1-carboxylic acid ethyl ester;

4-((S)-4-carboxy-2-{[4-(2-methoxymethyl-cyclopropyl)-6-phenyl-pyridine-2-carbonyl]-amino}-butyryl)-piperazine-1-carboxylic acid ethyl ester;

4-((S)-4-carboxy-2-{[4-(2-hydroxymethyl-cyclopropyl)-6-phenyl-pyridine-2-carbonyl]-amino}-butyryl)-piperazine-1-carboxylic acid ethyl ester;

4-{(S)-3-cyano-2-[(4,6-diphenyl-pyridine-2-carbonyl)-amino]-propionyl}-piperazine-1-carboxylic acid ethyl ester;

4-{(S)-4-carboxy-2-[(4,6-diphenyl-pyridine-2-carbonyl)-amino]-butyryl}-3-methyl-piperazine-1-carboxylic acid ethyl ester;

4-{(S)-2-[(4,6-diphenyl-pyridine-2-carbonyl)-amino]-3-hydroxy-propionyl}-piperazine-1-carboxylic acid ethyl ester;

4-{(S)-4-carboxy-2-[(4-phenyl-6-pyrazol-1-yl-pyridine-2-carbonyl)-amino]-butyryl}-piperazine-1-carboxylic acid ethyl ester;

4-((S)-4-carboxy-2-{[4-(3-hydroxy-propyl)-6-phenyl-pyridine-2-carbonyl]-amino}-butyryl)-piperazine-1-carboxylic acid ethyl ester;

4-((S)-4-carboxy-2-{[4-(3-hydroxy-3-methyl-but-1-ynyl)-6-phenyl-pyridine-2-carbonyl]-amino}-butyryl)-piperazine-1-carboxylic acid ethyl ester;

4-((S)-4-carboxy-2-{[4-(3-hydroxy-3-methyl-butyl)-6-phenyl-pyridine-2-carbonyl]-amino}-butyryl)-piperazine-1-carboxylic acid ethyl ester;

4-((S)-4-carboxy-2-{[4-(4-hydroxy-cyclohexyl)-6-phenyl-pyridine-2-carbonyl]-amino}-butyryl)-piperazine-1-carboxylic acid ethyl ester;

4-{(S)-4-carboxy-2-[(6-phenyl-4-phenylsulfanyl-pyridine-2-carbonyl)-amino]-butyryl}-piperazine-1-carboxylic acid ethyl ester;

4-((S)-4-carboxy-2-{[4-(2-hydroxy-cyclohexyl)-6-phenyl-pyridine-2-carbonyl]-amino}-butyryl)-piperazine-1-carboxylic acid ethyl ester;

4-{(S)-4-carboxy-2-[(6-phenyl-4-thiophen-3-yl-pyridine-2-carbonyl)-amino]-butyryl}-piperazine-1-carboxylic acid ethyl ester;

4-{(S)-4-carboxy-2-[(4-furan-3-yl-6-phenyl-pyridine-2-carbonyl)-amino]-butyryl}-piperazine-1-carboxylic acid ethyl ester;

4-{(S)-4-carboxy-2-[(4-isopropylsulfanyl-6-phenyl-pyridine-2-carbonyl)-amino]-butyryl}-piperazine-1-carboxylic acid ethyl ester;

4-((S)-3-(4-carboxy-phenyl)-2-{[4-(2-methoxymethyl-cyclopropyl)-6-phenyl-pyridine-2-carbonyl]-amino}-propionyl)-piperazine-1-carboxylic acid ethyl ester;

4-{(S)-4-carboxy-2-[(4-methyl-6-phenyl-pyridine-2-carbonyl)-amino]-butyryl}-piperazine-1-carboxylic acid ethyl ester;

4-((S)-4-carboxy-2-{[6-phenyl-4-(tetrahydro-furan-3-yloxy)-pyridine-2-carbonyl]-amino}-butyryl)-piperazine-1-carboxylic acid ethyl ester;

4-{(S)-4-carboxy-2-[(6-phenyl-pyridine-2-carbonyl)-amino]-butyryl}-piperazine-1-carboxylic acid ethyl ester;

4-{(S)-4-O-tert-butoxycarbonyl-2-[(4-chloro-6-phenyl-pyridine-2-carbonyl)-amino]-butyryl}-piperazine-1-carboxylic acid ethyl ester;

4-{(S)-4-tert-butoxycarbonyl-2-[(4-cyclopentyloxy-6-phenyl-pyridine-2 carbonyl)-amino]-butyryl}-piperazine-1-carboxylic acid ethyl ester;

4-((S)-4-tert-butoxycarbonyl-2-{[4-(1-hydroxy-1-methyl-ethyl)-6-phenyl-pyridine-2-carbonyl]-amino}-butyryl)-piperazine-1-carboxylic acid ethyl ester;

4-{(S)-4-tert-butoxycarbonyl-2-[(4,6-diphenyl-pyridine-2-carbonyl)-amino]-butyryl}-piperazine-1-carboxylic acid ethyl ester;

4-{(S)-4-tert-butoxycarbonyl-2-[(6-phenyl-4-pyrazol-1-yl-pyridine-2-carbonyl)-amino]-butyryl}-piperazine-1-carboxylic acid ethyl ester;

4-((S)-4-tert-butoxycarbonyl-2-{[4-(4-methoxy-phenyl)-6-phenyl-pyridine-2-carbonyl]-amino}-butyryl)-piperazine-1-carboxylic acid ethyl ester;

4-((S)-4-tert-butoxycarbonyl-2-{[4-cyclopropyl-6-phenyl-pyridine-2-carbonyl]-amino}-butyryl)-piperazine-1-carboxylic acid ethyl ester;

4-{(S)-4-tert-butoxycarbonyl-2-[(4-butyl-6-phenyl-pyridine-2-carbonyl)-amino]-butyryl}-piperazine-1-carboxylic acid ethyl ester;

4-{(S)-4-O-tert-butoxycarbonyl-2-[(4-[(R)-3-hydroxy-pyrrolidin-1-yl]-6-phenyl-pyridine-2-carbonyl)-amino]-butyryl}-piperazine-1-carboxylic acid ethyl ester;

4-{(S)-4-tert-butoxycarbonyl-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester;

4-{(S)-4-tert-butoxycarbonyl-2-[(6-phenyl-4-pyrrolidin-1-yl-pyridine-2-carbonyl)-amino]-butyryl}-piperazine-1-carboxylic acid ethyl ester;

4-((S)-4-tert-butoxycarbonyl-2-{[4-(2-hydroxy-ethylamino)-6-phenyl-pyridine-2-carbonyl]-amino}-butyryl)-piperazine-1-carboxylic acid ethyl ester;

4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid ethyl ester;

4-{(S)-4-tert-butoxycarbonyl-2-[(4-isopropylamino-6-phenyl-pyridine-2-carbonyl)-amino]-butyryl}-piperazine-1-carboxylic acid ethyl ester;

4-((S)-4-tert-butoxycarbonyl-2-{[4-(2-methoxymethyl-cyclopropyl)-6-phenyl-pyridine-2-carbonyl]-amino}-butyryl)-piperazine-1-carboxylic acid ethyl ester;

4-((S)-4-tert-butoxycarbonyl-2-{[4-(2-hydroxymethyl-cyclopropyl)-6-phenyl-pyridine-2-carbonyl]-amino}-butyryl)-piperazine-1-carboxylic acid ethyl ester;

4-{(S)-4-tert-butoxycarbonyl-2-[(4,6-diphenyl-pyridine-2-carbonyl)-amino]-butyryl}-3-methyl-piperazine-1-carboxylic acid ethyl ester;

4-{(S)-4-tert-butoxycarbonyl-2-[(4-phenyl-6-pyrazol-1-yl-pyridine-2-carbonyl)-amino]-butyryl}-piperazine-1-carboxylic acid ethyl ester;

4-((S)-4-tert-butoxycarbonyl-2-{[4-(3-hydroxy-propyl)-6-phenyl-pyridine-2-carbonyl]-amino}-butyryl)-piperazine-1-carboxylic acid ethyl ester;

4-((S)-4-tert-butoxycarbonyl-2-{[4-(3-hydroxy-3-methyl-but-1-ynyl)-6-phenyl-pyridine-2-carbonyl]-amino}-butyryl)-piperazine-1-carboxylic acid ethyl ester;

4-((S)-4-tert-butoxycarbonyl-2-{[4-(3-hydroxy-3-methyl-butyl)-6-phenyl-pyridine-2-carbonyl]-amino}-butyryl)-piperazine-1-carboxylic acid ethyl ester;

4-{(S)-4-tert-butoxycarbonyl-2-[(6-phenyl-4-phenylsulfanyl-pyridine-2-carbonyl)-amino]-butyryl}-piperazine-1-carboxylic acid ethyl ester;

4-{(S)-4-tert-butoxycarbonyl-2-[(6-phenyl-4-thiophen-3-yl-pyridine-2-carbonyl)-amino]-butyryl}-piperazine-1-carboxylic acid ethyl ester;

4-{(S)-4-tert-butoxycarbonyl-2-[(4-furan-3-yl-6-phenyl-pyridine-2-carbonyl)-amino]-butyryl}-piperazine-1-carboxylic acid ethyl ester;

4-{(S)-4-tert-butoxycarbonyl-2-[(4-isopropylsulfanyl-6-phenyl-pyridine-2-carbonyl)-amino]-butyryl}-piperazine-1-carboxylic acid ethyl ester;

4-((S)-3-(4-tert-butoxycarbonyl-phenyl)-2-{[4-(2-methoxymethyl-cyclopropyl)-6-phenyl-pyridine-2-carbonyl]-amino}-propionyl)-piperazine-1-carboxylic acid ethyl ester;

4-{(S)-4-tert-butoxycarbonyl-2-[(6-phenyl-pyridine-2-carbonyl)-amino]-butyryl}-piperazine-1-carboxylic acid ethyl ester;

4-[(S)-2-[(4,6-diphenyl-pyridine-2-carbonyl)-amino]-3-(2H-tetrazol-5-yl)-propionyl]-piperazine-1-carboxylic acid ethyl ester;

as well as the salts thereof (in particular the pharmaceutically acceptable salts thereof).

A further object of the invention is the compounds of formula I or $I_p$ (or of formula $I_{CE}$ or $I_{CEP}$) or their pharmaceutically acceptable salts as medicaments.

The compounds of formula I or $I_P$ and their pharmaceutically acceptable salts can be used as medicaments, e.g. in the form of pharmaceutical compositions for enteral or parental administration.

The invention thus also relates to pharmaceutical compositions containing at least one compound according to this invention (notably a compound of formula I or $I_P$ or $I_{CE}$ or $I_{CEP}$), or a pharmaceutically acceptable salt thereof, and a pharmaceutically acceptable carrier, diluent or excipient. In particular, the invention relates to pharmaceutical compositions containing at least one compound of formula I or $I_P$ (or of formula $I_{CE}$ or $I_{CEP}$) and a pharmaceutically acceptable carrier, diluent or excipient.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or $I_P$ or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Yet another object of this invention is the use of a compound of formula I or $I_P$ (or of formula $I_{CE}$ or $I_{CEP}$), or of a pharmaceutically acceptable salt thereof, for the manufacture of a medicament for:

the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocythaemia, sickle cell disease, inflammatory bowel disease, thrombotic thrombocytopaenic purpura, haemolytic uraemic syndrome;

for preventing thrombotic complications of septicaemia, adult respiratory distress syndrome, anti-phospholipid syndrome, heparin-induced thrombocytopaenia and pre-eclampsia/eclampsia;

for preventing cardiovascular complications after certain surgery procedures (notably coronary revascularisation like angioplasty (PTCA), other vascular graft surgery, endarterectomy or stent placement) or after accidental trauma;

for preventing organ graft rejection.

More generally, the invention relates to the use of a compound of formula I or $I_P$ (or of formula $I_{CE}$ or $I_{CEP}$), or of a pharmaceutically acceptable salt thereof, for the manufacture of a medicament for the treatment and/or prevention of occlusive vascular disorders as well as to the use of a compound of formula I or $I_P$ (or of formula $I_{CE}$ or $I_{CEP}$) for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

Among the above-mentioned uses of compounds of formula I or $I_P$ (or of formula $I_{CE}$ or $I_{CEP}$) or of pharmaceutically acceptable salts thereof for the manufacture of medicaments, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

The invention further relates to the use of a compound of formula I or $I_P$ (or of formula $I_{CE}$ or $I_{CEP}$), or of a pharmaceutically acceptable salt thereof, for the preservation of blood products in vitro (e.g. the preservation of platelet concentrates), or for the prevention of occlusion in extra-corporeal blood or blood product treatment machines (such as renal dialysis machines or plasmapheresis machines).

The invention also relates to methods of treatment for said disorders, said methods comprising the administration to a patient in need thereof of an effective amount of a compound of formula I or $I_P$ (or of formula $I_{CE}$ or $I_{CEP}$) or of a pharmaceutically acceptable salt thereof.

The preferences indicated for the compounds of formula I of course apply *mutatis mutandis* to the compounds of formula $I_P$, of formula $I_{CE}$, of formula $I_{CEP}$, of formula $I_B$, of formula $I_{BP}$, Of formula $I_O$, of formula $I_{OP}$, of formula $I_S$, of formula $I_{SP}$, of formula $I_N$, of formula $I_{NP}$, of formula $I_{NL}$, of formula $I_{NPL}$, of formula $I_{NR}$, of formula $I_{NPR}$, of formula $I_T$ or of formula $I_{TP}$, as well as to the salts and pharmaceutically acceptable salts of the compounds of formula I, of formula $I_P$, of formula $I_{CE}$, of formula $I_{CEP}$, of formula $I_B$, of formula $I_{BP}$, of formula $I_O$, of formula $I_{OP}$, of formula $I_S$, of formula $I_{SP}$, of formula $I_N$, of formula $I_{NP}$, of formula $I_{NL}$, of formula $I_{NPL}$, of formula $I_{NR}$, of formula $I_{NPR}$, of formula $I_T$ or of formula $I_{TP}$. The same applies to these compounds as medicaments, to pharmaceutical compositions containing these compounds as active principles or to the uses of these compounds for the manufacture of a medicament for the treatment of the diseases according to this invention.

According to the invention, the compounds of formula I (or of formula $I_{CE}$) can be prepared by the process described below.

Preparation of the Compounds of Formula I

Abbreviations:

The following abbreviations are used throughout the specification and the examples:

abs. anhydrous
Ac acetyl
aq. aqueous
bR. broad
BSA bovine serum albumin
CC column chromatography
conc. concentrated
DCC 1,3-dicyclohexylcarbodiimide
DCM dichloromethane
DIPEA diisopropylethylamine
DME 1,2-dimethoxyethane
DMF N,N-dimethylformamide
EA ethyl acetate
EDCI N-(3-dimethylaminopropyl)-N'-ethylcarbodiimide (as HCl salt)
EDTA ethylenediaminetetraacetic acid
Et ethyl
Hept heptane
Hex hexane
HOBT 1-hydroxybenzotriazole
HV high vacuum
MCPBA meta-chloroperbenzoic acid
Me methyl
n-BuLi n-butyl lithium
org. organic Pd/C palladium on carbon
Ph phenyl
PyBOP benzotriazole-1-yl-oxy-tris-pyrrolidino-phosphonium hexafluorophosphate
TBAF tetrabutylammonium fluoride
TBTU O-benzotriazol-1-yl-N,N,N',N'-tetramethyluronium tetrafluoroborate
tBu tert-butyl
TFA trifluoroacetic acid
THF tetrahydrofuran
TLC thin layer chromatography
TMSCN trimethylsilyl cyanide
RT room temperature
$t_R$ retention time
Tris tris-(hydroxymethyl)aminomethane General Preparation Routes:

Preparation of the Compounds of Formula I Wherein Both $R^a$ and $R^b$ are Hydrogen The various compounds of formula I wherein both $R^a$ and $R^b$ are hydrogen can be prepared using the general routes summarised in Scheme 1 hereafter.

Scheme 1

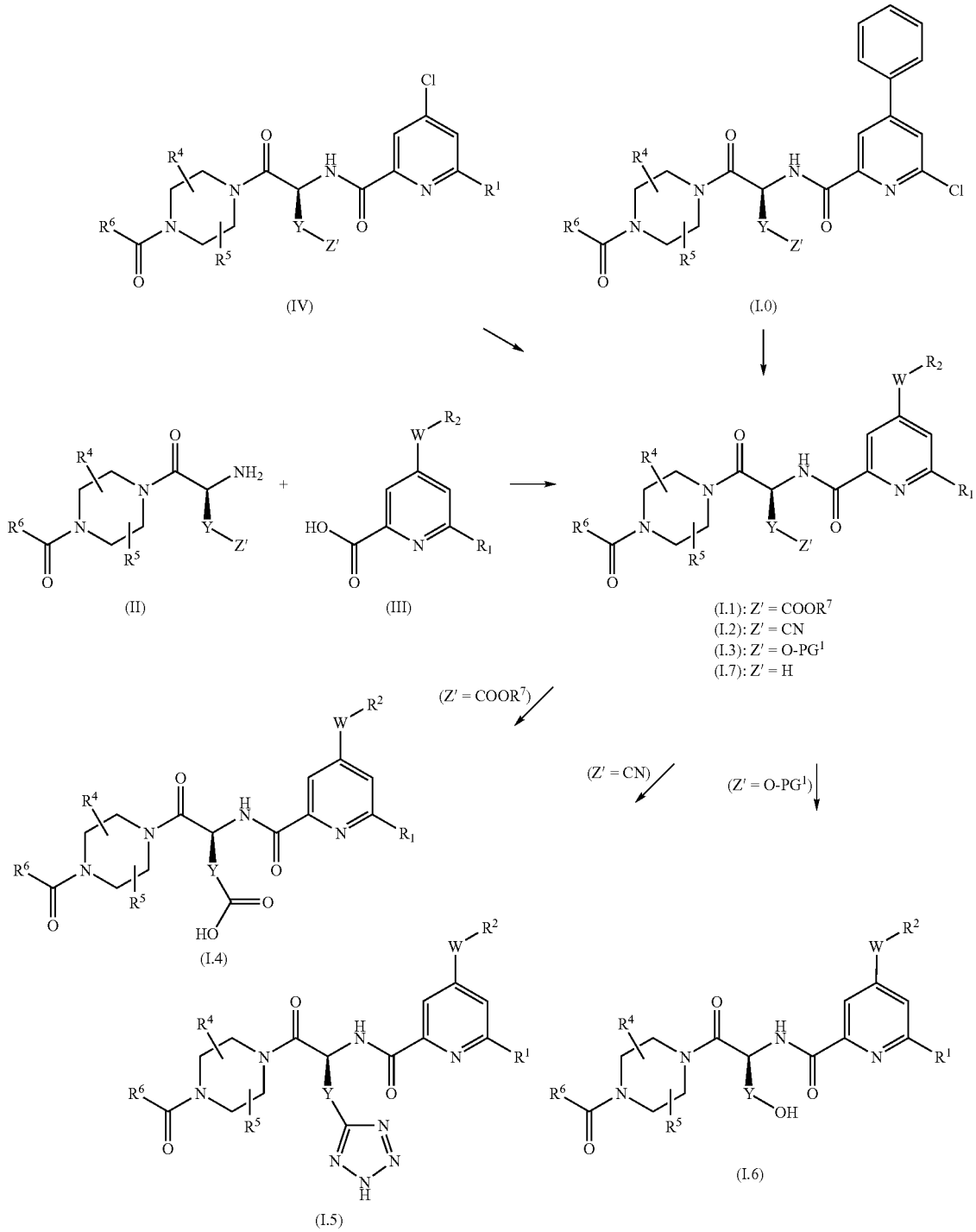

The compounds of formula I wherein both $R^a$ and $R^b$ are hydrogen and Z represents $COOR^7$ (i.e. the compounds of formula I.1 in which W, Y, $R^1$, $R^2$, $R^4$, $R^5$ and $R^6$ are as defined in formula I and Z' represents $COOR^7$), wherein both $R^a$ and $R^b$ are hydrogen and Z represents CN (i.e. the compounds of formula I.2 in which W, Y, $R^1$, $R^2$, $R^4$, $R^5$ and $R^6$ are as defined in formula I and Z' represents CN), wherein both $R^a$ and $R^b$ are hydrogen and Z represents O-$PG^1$, $PG^1$ being a suitable protecting group for an alcohol function (i.e. the compounds of formula I.3 in which W, Y, $R^1$, $R^2$, $R^4$, $R^5$ and $R^6$ are as defined in formula I and Z' represents O-$PG^1$) or wherein both $R^a$ and $R^b$ are hydrogen and Z represents hydrogen (i.e. the compounds of formula I.7 in which W, Y, $R^1$, $R^2$, $R^4$, $R^5$ and $R^6$ are as defined in formula I and Z' represents hydrogen) can be prepared (Scheme 1) by coupling a compound of formula II wherein $R^4$, $R^5$, $R^6$, Y and Z' have the same meanings as in formula I.1, I.2, I.3 or I.7 with a compound of formula III wherein W, $R^1$ and $R^2$ have the same meanings as in formula I.1, I.2, I.3 or I.7, using standard peptide coupling methods such as HOBT, EDCI, DCC, benzotriazole-1-yl-oxy-tris-pyr-rolidino-phosphonium hexafluorophosphate, benzotriazole-1-yl-oxy-tris-(dimethylamino)-phosphonium hexafluorophosphate, 2-(1H-benzotriazole-1-yl)-1,1,3,3-tetramethyl uronium tetrafluoroborate, optionally in the presence of a suitable base such as TEA, DIPEA or N-methylmorpholine and in a suitable solvent such as DCM, THF or DMF, preferably at a temperature around RT.

The compounds of formula I.4 can then be obtained (Scheme 1) by hydrolysis of the corresponding compounds of formula I.1 wherein Z' is —$COOR^7$ ($R^7$ being alkyl) under standard conditions well known to one skilled in the art.

The tetrazole derivatives of formula I.5 can be prepared (Scheme 1) by conversion of the corresponding cyano derivatives of formula I.2 wherein Z' is —CN using the well-known methodology with sodium azide, optionally in the presence of zinc dibromide.

The compounds of formula I.6 can be prepared (Scheme 1) by deprotection of the corresponding compounds of formula I.3 wherein Z' is —O-$PG^1$ and $PG^1$ is a suitable protecting group for an alcohol function. Suitable alcohol function protection groups and protection and deprotection methods are well known to one skilled in the art (see notably "Protective groups in organic synthesis", Greene T. W. and Wuts P. G. M., Wiley-Interscience, 1999).

Alternatively, compounds of formula I.1, I.2 or I.3 wherein $R^1$ is however different from halogen can be obtained as described hereafter.

The compounds of formula IV (wherein $R^1$ has the same meaning as in formula I.1, I.2 or I.3 except that it is not halogen and the other symbols are as defined in formula I.1, I.2 or I.3) can be converted into a compound of formula I.1, I.2 or I.3 wherein W is —$NR^3$— by aromatic substitution reaction with an amine of formula $HNR^2R^3$, the reaction being carried out in a microwave apparatus preferably at a temperature between 160° C. and 180° C., in a suitable solvent such as THF, MeCN or DMF.

The intermediates of formula IV can also be converted into a compound of formula I.1, I.2 or I.3 wherein W is —O— by aromatic substitution reaction with a alcohol of formula $HOR^2$ in the presence of a suitable base such as NaH, the reaction being carried out in a suitable solvent such as THF, MeCN or DMF and preferably heating between 50° C. and 80° C.

The intermediates of formula IV can also be converted into a compound of formula I.1, I.2 or I.3 wherein W is —S— by aromatic substitution reaction with a thiol of formula $HSR^2$ in the presence of a suitable base such as NaH, the reaction being carried out in a suitable solvent such as THF, MeCN or DMF and preferably around RT.

The intermediates of formula IV can also be converted into a compound of formula I.1, I.2 or I.3 wherein W is a bond, using a reagent of formula $R^2$—B—$(OR)_2$, R being hydrogen or alkyl, using standard conditions for a Suzuki reaction, and preferably a boronic acid or ester derivative in the presence of a suitable base such as aq. $Na_2CO_3$ or $K_2CO_3$, in the presence of a suitable palladium catalyst such as tetrakis(triphenylphosphine) palladium or tris-(dibenzylidenaceton)-di-palladium, optionally in the presence of a ligand such as $PPh_3$, in a suitable solvent such as DME, EtOH or toluene, and preferably heating between 90° C. and 110° C.

The intermediates of formula IV can also be converted into a compound of formula I.1, I.2 or I.3 wherein W is a bond, using a reagent of formula $R^2$—Sn—$(Bu)_3$, using standard conditions for a Stille reaction, and preferably a stannane derivative in the presence of a suitable palladium catalyst such as tetrakis(triphenylphosphine)palladium, in a suitable solvent such as toluene, and preferably heating between 110° C. and 13° C.

The intermediates of formula IV can also be converted into a compound of formula I.1, I.2 or I.3 wherein W is —C≡C—, using a reagent of formula $R^2$—C≡CH, using standard conditions for a Sonogashira reaction, and preferably an alkyne derivative in the presence of a suitable base such as $NEt_3$, in the presence of a suitable palladium catalyst such as bis-(triphenylphosphine) palladium(II)-dichloride, in the presence of a suitable copper catalyst such as CuI, in a suitable solvent such as DMF, and at RT. The compounds of formula I.1, I.2 or I.3 wherein W is —C≡C— can then be reduced in the presence of a suitable catalyst such as Raney Nickel, in a suitable solvent such as MeOH, at a temperature preferably around RT and under hydrogen to allow the preparation of particular compounds of formula I.1, I.2 or I.3 wherein W is a bond.

In the particular case wherein W represents a bond and $R^2$ is phenyl, the compounds of formula I.1, I.2 or I.3 can be obtained by conversion of the compound of formula I.0 using the same methods as those described previously for the compounds of formula IV.

The compounds of formula I.0 can be obtained as summarised in Scheme 1a hereafter.

Scheme 1a

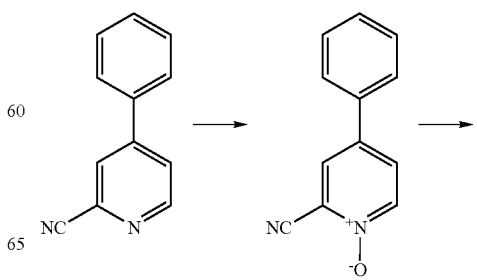

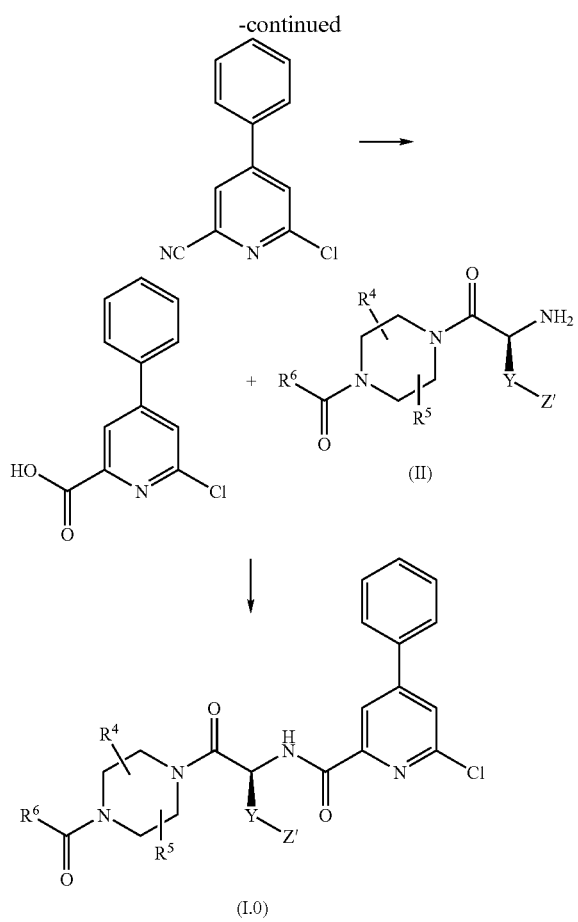

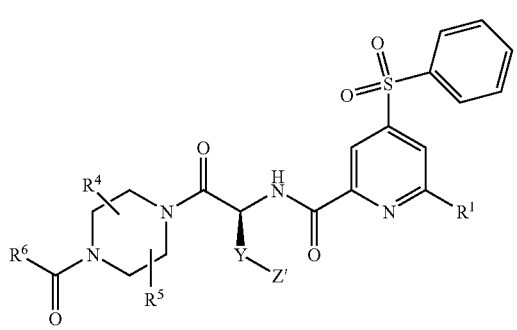

which bears a phenylsulfonyl instead of a chloro as leaving group.

4-phenyl-pyridine-2-carbonitrile is easily accessible using a literature procedure (*J. Org. Chem.* (1992), 57, 6020-6025). It can be oxidised using standard conditions for the oxidation of a pyridine, using standard oxidizing agents such as MCPBA, in a suitable solvent such as DCM, and at a temperature between RT and 40° C. The pyridine oxide derivative thus obtained can be chlorinated using standard conditions (e.g. phosphoryl chloride at reflux). The cyano group can be further hydrolysed using standard conditions (e.g. conc. hydrochloric acid at reflux). The chloropyridine derivative can be coupled to compounds of formula II as defined earlier, using the same standard coupling methods as those described above for the coupling reaction involving compounds of formulae II and III, yielding the compounds of formula (I.0).

In particular cases, the intermediate of formula IV may be replaced by an intermediate of formula V Preparation of the Compounds of Formula I Wherein $R^a$ is Fluorine (Compounds of Formula $I_F$)

The compounds of formula $I_F$ can be prepared from compounds of formula XVI

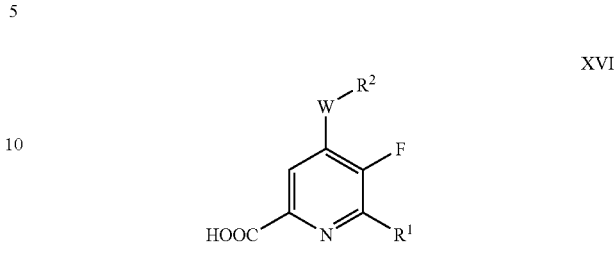

wherein W, $R^1$ and $R^2$ have the same meaning as in formula $I_F$. The compounds of formula XVI can then be used in place of the compounds of formula III in the corresponding route of Scheme 1 to yield the compounds of formula $I_F$.

Alternatively the compounds of formula $I_F$ can be prepared from compounds of formula $IV_F$

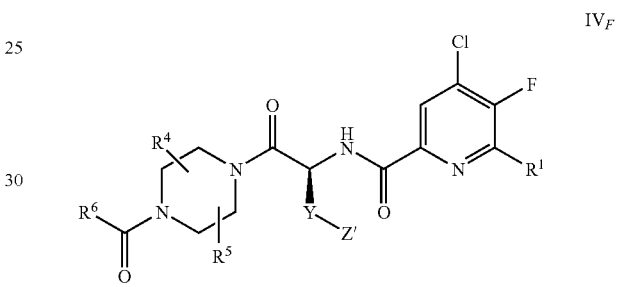

wherein $R^1$, $R^2$, $R^4$, $R^5$, $R^6$, Y and Z' have the same meaning as in formula $I_F$. The compounds of formula $IV_F$ can then be used in place of the compounds formula IV in the corresponding route of Scheme 1 to yield the compounds of formula $I_F$.

Preparation of the Compounds of Formula I Wherein $R^B$ is Alkoxy (Compounds of Formula $I_a$)

The compounds of formula $I_A$ can be prepared from compounds of formula $IV_A$

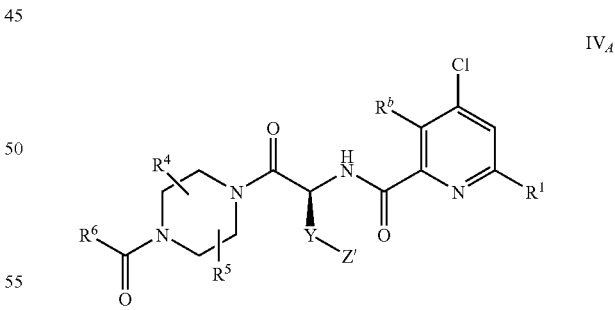

wherein $R^1$, Y, Z', $R^4$, $R^5$ and $R^6$ have the same meanings as in formula IV and $R^b$ has the same meanings as in formula $I_A$. The compounds of formula $IV_A$ can then be used in place of the compounds of formula IV in the corresponding route of Scheme 1 to yield the compounds of formula $I_A$.

Preparation of the Various Synthesis Intermediates
Preparation of the Compounds of Formula II The compounds of formula II can be prepared (Scheme 2) by coupling the piperazine derivatives of formula VI wherein $R^4$, $R^5$ and $R^6$ have the same meanings as in formula II with the compounds of formula VII wherein Y and Z' have the same meanings as in formula II and $PG^2$ is a suitable protecting group for an amine function, using the same standard peptide coupling methods as those described above for the coupling reaction involving compounds of formulae II and III. The resulting intermediates of formula VIII can then be deprotected using standard methods (see e.g. "Protective groups in organic synthesis", Greene T. W. and Wuts P. G. M., Wiley-Interscience, 1999) to yield the compounds of formula II.

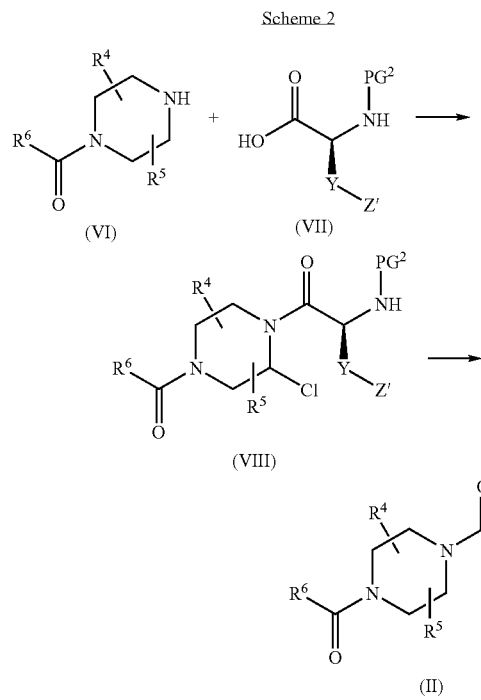

Preparation of the Compounds of Formula III

The carboxypyridine derivatives of formula III wherein W represents an oxygen atom and $R^1$ is phenyl can be prepared as summarised in Scheme 3 hereafter.

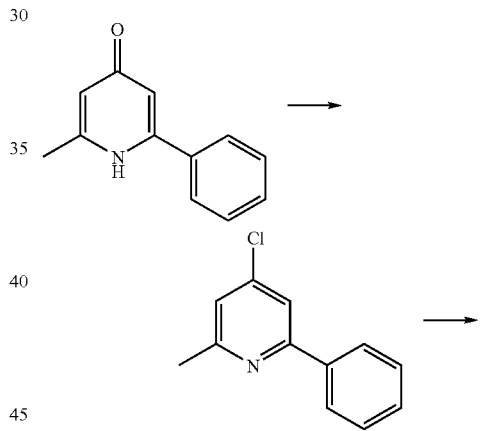

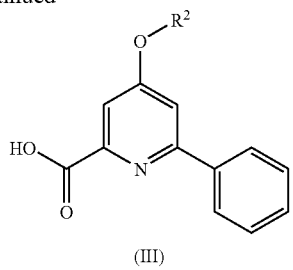

The starting material 2-methyl-6-phenyl-1H-pyridin-4-one is easily accessible using a literature procedure (*J. Med. Chem.* (2004), 47, 4277-4285). It can be alkylated using a reagent of formula $R^2$—Hal (wherein Hal is Cl, Br or I), in the presence of a suitable base such as $Na_2CO_3$, $K_2CO_3$ or $Cs_2CO_3$, in a suitable solvent such as MeCN, THF or DMF, and at a temperature preferably between RT and 70° C. The intermediate of formula IX thus obtained can then be oxidised using standard methods known to the skilled artisan, preferably by refluxing it in pyridine in the presence of $SeO_2$.

Alternatively, the carboxypyridine derivatives of formula III wherein W represents a bond and $R^2$ represents aryl, heteroaryl or pyrazolyl can be prepared as summarised in Scheme 3a hereafter.

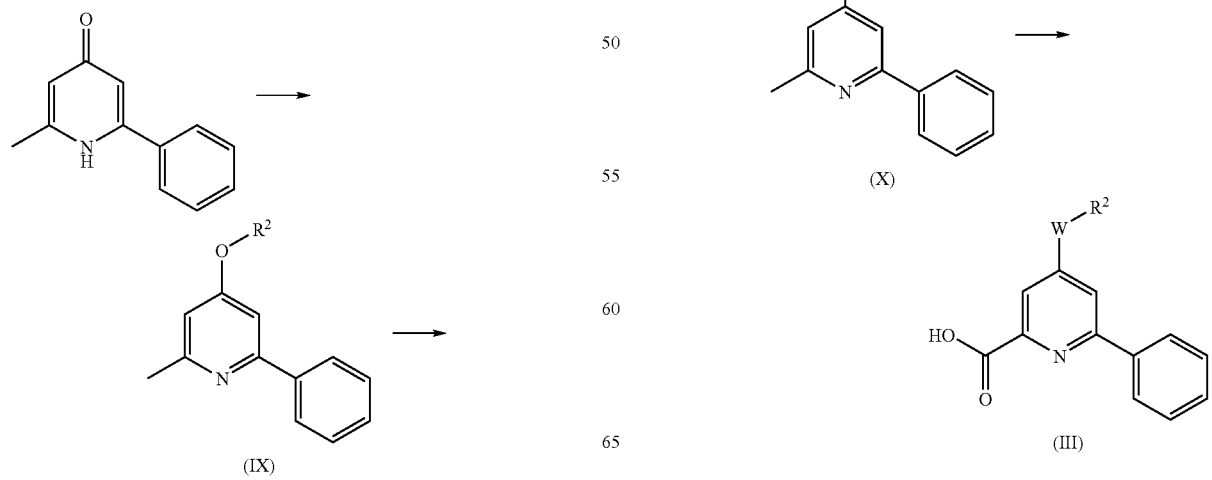

According to this alternative route, 2-methyl-6-phenyl-1H-pyridin-4-one is chlorinated to yield 4-chloro-2-methyl-6-phenyl-pyridine using standard conditions (e.g. phosphoryl chloride at reflux). 4-chloro-2-methyl-6-phenyl-pyridine can then be substituted (aromatic nucleophilic substitution) by pyrazole in the presence of a base such as NaH, in a suitable solvent such as THF or DMF and heating at a temperature preferably between 80° C. and 120° C. The resulting compound of formula X can then be oxidised into a compound of formula III using the same methods as those described above for the oxidation reaction of compounds of formula IX.

Alternatively, 4-chloro-2-methyl-6-phenyl-pyridine can also be converted into a compound of formula X wherein W is a bond using a reagent of formula $R^2$—B—$(OR)_2$, R being hydrogen or alkyl, using the same standard conditions for a Suzuki reaction as those described above for the Suzuki reaction involving compounds of formula IV.

Besides, 4-chloro-2-methyl-6-phenyl-pyridine can also be converted into 4-chloro-6-phenyl-pyridine-2-carboxylic acid using the same methods as those described above for the oxidation reaction of compounds of formula IX. 4-chloro-6-phenyl-pyridine-2-carboxylic acid can then be converted into a compound of formula III wherein W is —$NR^3$—, using an amine of formula $HNR^2R^3$, using the same conditions as those described above for the aromatic nucleophilic substitution of compounds of formula IV.

Preparation of the Compounds of Formula IV

The compounds of formula IV can be obtained (Scheme 4) by coupling of the compounds of formula II with the chloropyridine derivatives of formula XI wherein $R^1$ has the same meaning as in formula IV, using the same standard coupling methods as those described above for the coupling reaction involving compounds of formulae TI and III, and preferably using PyBOP.

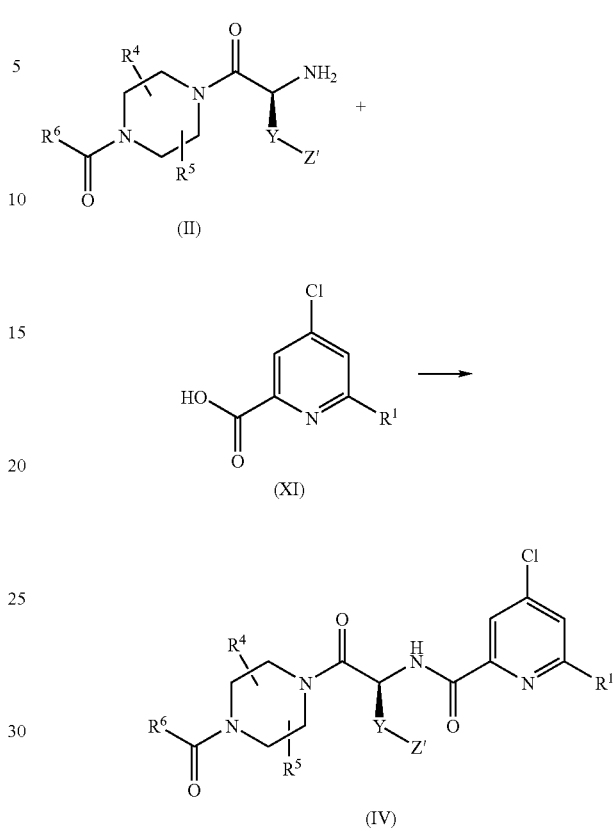

Preparation of the Compounds of Formula $IV_F$

The compounds of formula $IV_F$ can be obtained as summarised in Scheme 4a hereafter.

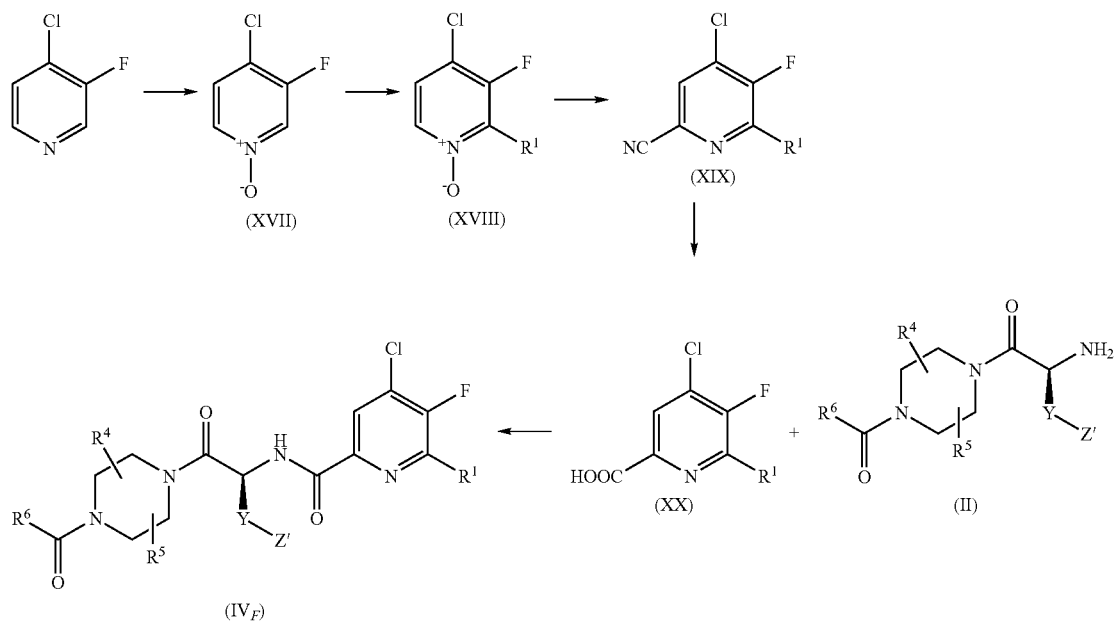

4-chloro-3-fluoropyridine can be oxidised into a compound of formula XVII using standard conditions for the oxidation of a pyridine, using standard oxidizing agents such as MCPBA, in a suitable solvent such as DCM or CHCl₃, and at a temperature between RT and 45° C. The pyridine oxide derivative of formula XVII thus obtained can be converted into a compound of formula XVIII using Br—R¹, in the presence of a suitable palladium catalyst such as palladium diacetate, in the presence of a suitable ligand such as tri-tert-butylphosphonium tetrafluoroborate, in the presence of a suitable base such as K₂CO₃, in a suitable solvent such as toluene, and preferably heating at 110° C. The compound of formula XVIII can then be converted into a compound of formula XIX using standard conditions for the introduction of a cyano group, using reagents such as trimethylsilyl cyanide and acetyl chloride, in a suitable solvent such as DCM, and preferably at RT. The compound of formula XX can then be obtained by using standard conditions for the hydrolysis of a cyano group (e.g. conc. hydrochloric acid at reflux). The compounds of formula XX can then be used in place of the compounds of formula XI in the corresponding route of Scheme 4 to yield the compounds of formula IV$_F$.

Preparation of the Compounds of Formula IV$_A$

The compounds of formula IV$_A$ can be obtained by coupling the compounds of formula XXI

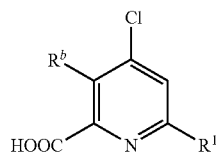

XXI wherein R¹ has the same meaning as in formula IV and R$^b$ has the same meaning as in formula I$_A$ with the appropriate compounds of formula II using the same standard coupling methods as those described above for the coupling reaction involving compounds of formulae II and III, and preferably using PyBOP.

Preparation of the Compounds of Formula V

The compounds of formula V can be prepared as summarised in Scheme 5 hereafter.

Scheme 5

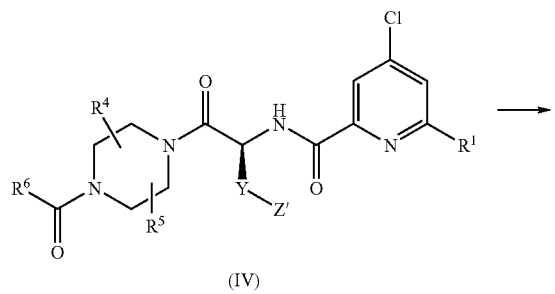

(IV)

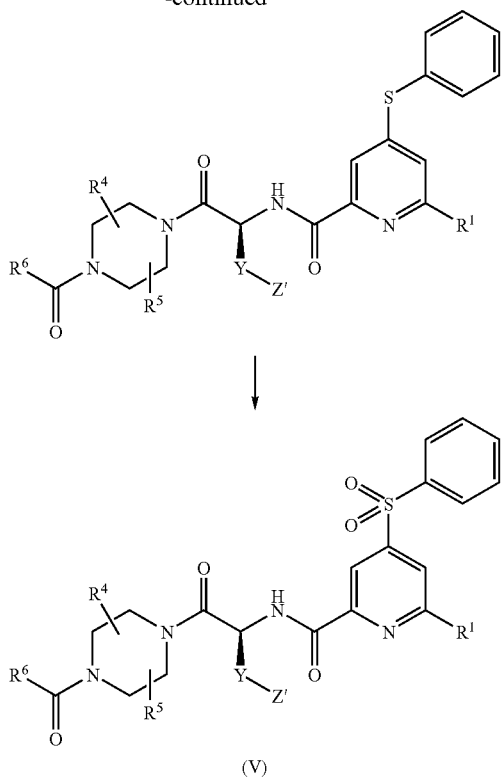

Accordingly, the required thiol intermediate (which is a compound of formula I wherein W is —S— and R² is phenyl) can be obtained from the compound of formula IV using the method described above for preparing the compounds of formula I.1, I.2 or I.3 wherein W is —S— and then be oxidised into the compound of formula V using standard oxidizing agents such as MCPBA, in a suitable solvent such as DCM, and at a temperature between 0° C. and RT.

Preparation of the Compounds of Formula VI

Three situations have to be distinguished for the preparation of compounds of formula VI, namely the cases wherein R⁴ and R⁵ are both hydrogen (Scheme 5), the cases wherein one of and R⁵ is hydrogen whereas the other is methyl (Scheme 5a) and eventually the cases wherein R⁴ and R⁵ are both methyl.

Scheme 6

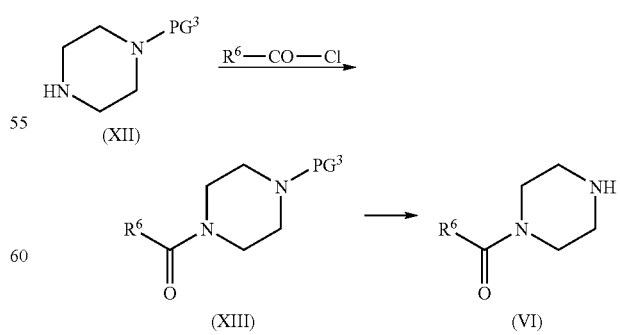

The compounds of formula VI wherein R⁴ and R⁵ are both hydrogen can be prepared (Scheme 6) by reacting the piperazine derivative of formula XII (wherein PG³ is a suitable protecting group for an amine function) with the acid chloride of formula $R^6$—CO—Cl (wherein $R^6$ has the same meaning as in formula VI) in the presence of a suitable base such as $NEt_3$, DIPEA, N-methylmorpholine, in a suitable solvent such as DCM, THF or DMF, at a temperature preferably around RT. The intermediates of formula XIV are converted into the compounds of formula VIII by cleaving off the protecting group $PG^3$ using standard conditions for the deprotection of amines, and preferentially Pd/C in a suitable solvent such as MeOH, EtOH, THF or EA, or TFA or hydrochloric acid in a suitable solvent such as DCM, $Et_2O$, dioxane or EA.

The two cases wherein one of $R^4$ and $R^5$ is hydrogen whereas the other is methyl are dealt with in Scheme 6a hereafter.

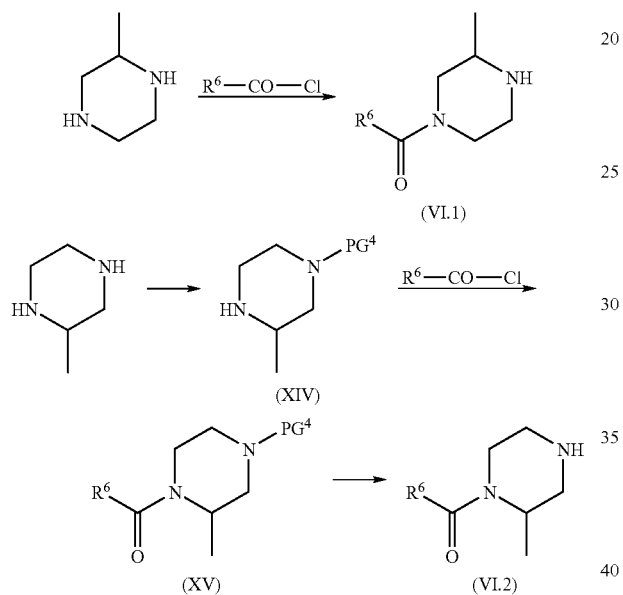

The compounds of formula VI.1 can be prepared (top of Scheme 6a) by direct coupling with a chloro derivative of formula $R^6$—CO—Cl. To obtain the compounds of formula VI.2 (bottom of Scheme 6a), a protection by an amine protecting group $PG^4$ should first be carried out. The intermediate of formula XIV thus obtained is then coupled with the acid chloride of formula $R^6$—CO—Cl and the coupling product of formula XV is then deprotected as described above for the compounds of formula XIII.

For the particular case wherein $R^4$ and $R^5$ are both methyl, the disubstituted piperazine may be coupled to the acid chloride of formula $R^6$—CO—Cl according to a procedure described by Bishop M. J., et al. in *J. Med. Chem.* (2003), 623-633, yielding the corresponding piperazine derivative of formula VI.

Preparation of the Compounds of Formula VII

If not commercially available, these compounds can be prepared according to standard methods by the skilled artisan from commercially available compounds.

Preparation of the Compounds of Formula XVI

The compounds of formula XVI can be obtained as summarised in Scheme 7 hereafter.

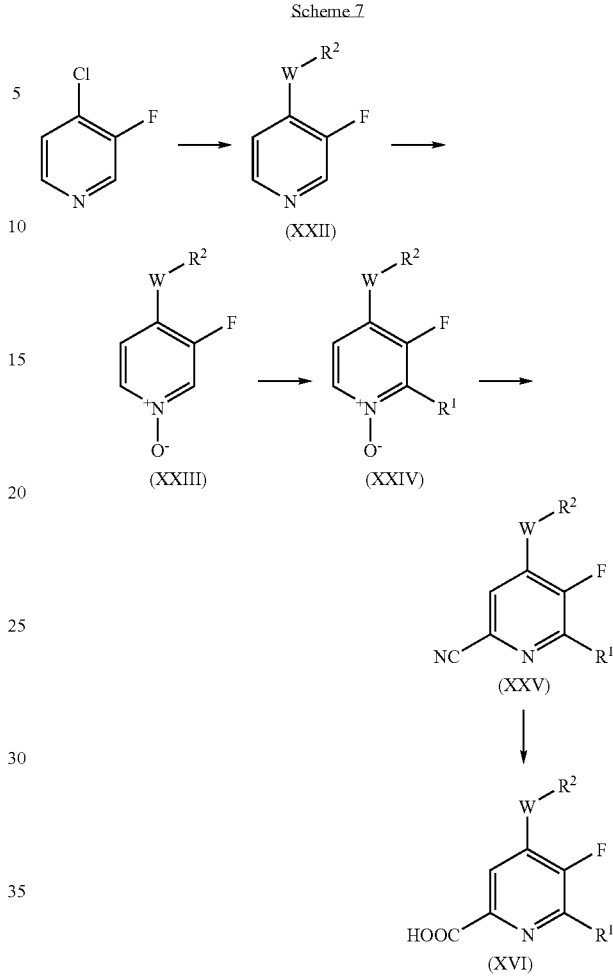

4-chloro-3-fluoropyridine can be converted (Scheme 7) into a compound of formula XXII wherein W is —$NR^3$—, using an amine of formula $HNR^2R^3$, using the same conditions as those described above for the aromatic nucleophilic substitution of compounds of formula IV. Alternatively, 4-chloro-3-fluoropyridine can also be converted into a compound of formula XXII wherein W is a bond using a reagent of formula $R^2$—B—$(OR)_2$, R being hydrogen or alkyl and $R^2$ being aryl, using the same standard conditions for a Suzuki reaction as those described above for the compounds of formula IV. Furthermore, 4-chloro-3-fluoropyridine can also be converted into a compound of formula XXII wherein W is a bond, using a reagent of formula $R^2$—Sn—$(Bu)_3$, $R^2$ being alkyl, hydroxyalkyl, alkoxyalkyl or cycloalkyl, using the same standard conditions for a Stille reaction as those described above for the compounds of formula IV. Moreover, 4-chloro-3-fluoropyridine can also be converted into a compound of formula XXII wherein W is —C≡C—, using a reagent of formula $R^2$—C≡CH, using the same standard conditions for a Sonogashira reaction as those described above for the compounds of formula IV.

The intermediate of formula XXII can be oxidised using standard conditions for the oxidation of a pyridine as those described above for 4-chloro-3-fluoropyridine. The pyridine oxide derivative of formula XXIII thus obtained can be converted into a compound of formula XXIV using Br—$R^1$, using the same standard conditions as those described above for the compounds of formula XVIII. The compound of formula XXIV can then be converted into a compound of formula XXV using the same standard conditions for the introduction of a cyano group as those described above for the compounds of formula XXX, however using dimethylcarbamoyl chloride instead of acetyl chloride. The compound of formula XVI can then be obtained by using standard conditions for the hydrolysis of a cyano group (e.g. conc. hydrochloric acid at reflux).

Preparation of the Compounds of Formula XXI

The compounds of formula XXI can be obtained as summarised in Scheme 8 hereafter.

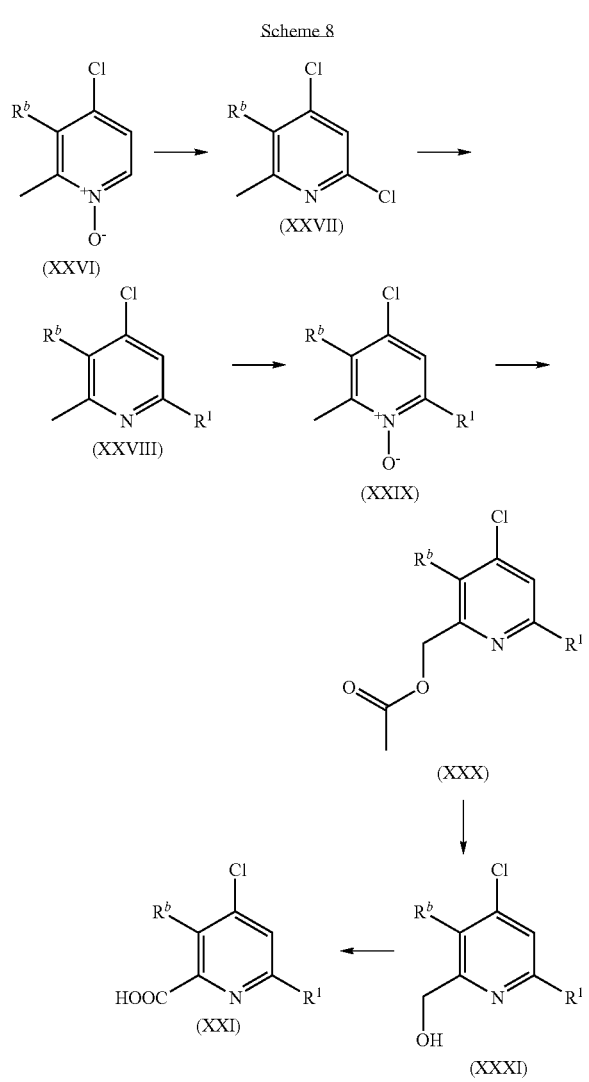

The compounds of formula XXVI can be converted into compounds of formula XXVII by refluxing in POCl$_3$. The compounds of formula XXVIII can be obtained using the same conditions as those described above for the Suzuki reaction of compounds of formula IV, using a reagent of formula R$^1$—B—(OH)$_2$. The compounds of formula XXIX can then be prepared using the same standard conditions as those described above for the pyridine oxidation reaction of 4-phenyl-pyridine-2-carbonitrile. The compounds of formula XXX can then be obtained by heating in acetic anhydride, preferably at 120° C. The hydrolysis of the compounds of formula XXX can be performed using standard conditions for an ester cleavage reaction (e.g. NaOH in MeOH/H$_2$O). The intermediates of formula XXXI thus obtained can then be oxidised into the acids of formula XXI using standard oxidising agents such as KMnO$_4$, preferably in the presence of a base such as NaOH, in a suitable solvent such as dioxane.

Preparation of the Compounds of Formula XXVI

The compounds of formula XXVI can be obtained as summarised in Scheme 9 hereafter.

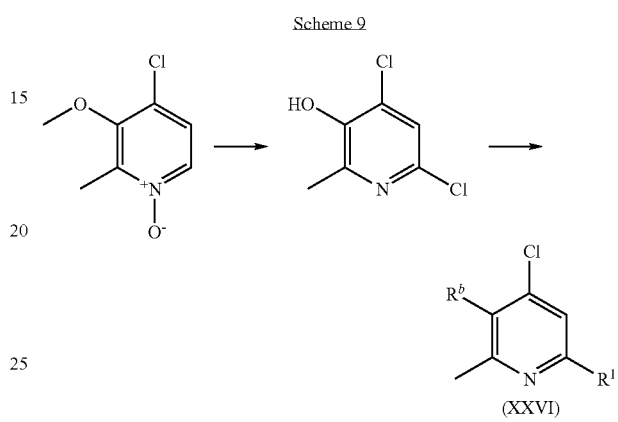

4-chloro-3-methoxy-2-methylpyridine N-oxide can be converted into 4-chloro-3-hydroxy-2-methylpyridine N-oxide by using standard reagents for a demethylation reaction such as BBr$_3$, in a suitable solvent such as DCM, at a suitable temperature between 0° C. and RT. The compounds of formula XXVI can then be obtained by using the same standard conditions for an alkylation reaction as those described above for the compounds of formula III wherein W represents an oxygen atom, using a reagent of formula R$'^b$-Hal (wherein Hal is Cl, Br or I), R$'^b$ being an alkyl group such that OR$'^b$=R$^b$.

Particular embodiments of the invention are described in the following Examples, which serve to illustrate the invention in more detail without limiting its scope in any way.

EXAMPLES

Characterization Methods Used

The LC-MS retention times have been obtained using the following elution conditions:

A) LC-MS (A):

A X-terra column (MS C18 5 µm, 4.6×50 mm) was used. The two elution solvents were as follows: solvent A=water+0.06% formic acid; solvent B=acetonitrile+0.06% formic acid. The eluent flow rate was 3 ml/min and the characteristics of the eluting mixture proportion in function of the time t from start of the elution are summarized in the table below (a linear gradient being used between two consecutive time points):

| | t (min) | | | | |
|---|---|---|---|---|---|
| | 0 | 1 | 1.25 | 1.30 | 1.75 |
| Solvent A (%) | 95 | 5 | 5 | 95 | 95 |
| Solvent B (%) | 5 | 95 | 95 | 5 | 5 |

B) LC-MS (B):

A Zorbax® column (Agilent SB.Aq 5 μm, 4.6×50 mm) was used. The two elution solvents were as follows: solvent A=water+0.04% TFA; solvent B=acetonitrile. The eluent flow rate was 4.5 ml/min and the characteristics of the eluting mixture proportion in function of the time t from start of the elution are summarized in the table below (a linear gradient being used between two consecutive time points):

|  | t (min) | | | |
| --- | --- | --- | --- | --- |
|  | 0 | 1 | 1.45 | 1.55 |
| Solvent A (%) | 95 | 5 | 5 | 95 |
| Solvent B (%) | 5 | 95 | 95 | 5 |

Preparative LC-MS Methods Used

The purifications by preparative LC-MS have been performed using the conditions described hereafter.

A Zorbax® column (PrepHT SB.Aq 5 mm, 21.2×50 mm) was used. The two elution solvents were as follows: solvent A=water+0.2% formic acid; solvent B=acetonitrile+0.2% formic acid. The eluent flow rate was 95 ml/min and the characteristics of the eluting mixture proportion in function of the time t from start of the elution are summarized in the tables below (a linear gradient being used between two consecutive time points):

I) Preparative LC-MS (I):

|  | t (min) | | | | | | | |
| --- | --- | --- | --- | --- | --- | --- | --- | --- |
|  | 0 | 0.6 | 3.3 | 3.9 | 4.5 | 5.1 | 5.2 | 6 |
| Solvent A (%) | 89.5 | 89.5 | 68.5 | 68.5 | 0 | 0 | 89.5 | 89.5 |
| Solvent B (%) | 10.5 | 10.5 | 31.5 | 31.5 | 100 | 100 | 10.5 | 10.5 |

II) Preparative LC-MS (II):

|  | t (min) | | | | | | | |
| --- | --- | --- | --- | --- | --- | --- | --- | --- |
|  | 0 | 0.6 | 3.3 | 3.9 | 4.5 | 5.1 | 5.2 | 6 |
| Solvent A (%) | 79 | 79 | 58 | 58 | 0 | 0 | 79 | 79 |
| Solvent B (%) | 21 | 21 | 42 | 42 | 100 | 100 | 21 | 21 |

III) Preparative LC-MS (III):

|  | t (min) | | | | | | | |
| --- | --- | --- | --- | --- | --- | --- | --- | --- |
|  | 0 | 0.6 | 3.3 | 3.9 | 4.5 | 5.1 | 5.2 | 6 |
| Solvent A (%) | 68.5 | 68.5 | 42 | 42 | 0 | 0 | 68.5 | 68.5 |
| Solvent B (%) | 31.5 | 31.5 | 58 | 58 | 100 | 100 | 31.5 | 31.5 |

IV) Preparative LC-MS (IV):

|  | t (min) | | | | | | | |
| --- | --- | --- | --- | --- | --- | --- | --- | --- |
|  | 0 | 0.6 | 3.3 | 3.9 | 4.5 | 5.1 | 5.2 | 6 |
| Solvent A (%) | 58 | 58 | 31.6 | 31.6 | 0 | 0 | 58 | 58 |
| Solvent B (%) | 42 | 42 | 68.4 | 68.4 | 100 | 100 | 42 | 42 |

V) Preparative LC-MS (V):

|  | t (min) | | | | | | | |
| --- | --- | --- | --- | --- | --- | --- | --- | --- |
|  | 0 | 0.6 | 3.3 | 3.9 | 4.5 | 5.1 | 5.2 | 6 |
| Solvent A (%) | 42 | 42 | 21 | 21 | 0 | 0 | 42 | 42 |
| Solvent B (%) | 58 | 58 | 79 | 79 | 100 | 100 | 58 | 58 |

Example 1

4-{(S)-4-carboxy-2-[(4-chloro-6-phenyl-pyridine-2-carbonyl)-amino]-butyryl}-piperazine-1-carboxylic acid ethyl ester 1.1. (Z)-4-phenylamino-pent-3-en-2-one A solution of 2,4-pentanedione (7.2 ml), aniline (7.65 ml) and a catalytic amount of para-toluenesulfonic acid monohydrate (665 mg) in toluene (70 ml) was refluxed for 8 h in a round bottom flask equipped with a Dean Stark apparatus and condenser. The solution was concentrated to dryness and the crude purified by CC (Hept/EA 8:2, then 7:3) to give 6.74 g of the desired compound.

LC-MS (B): $t_R$=0.88 min; [M+H]$^+$: 176.3.

1.2. 2-methyl-6-phenyl-4(1H)-pyridinone

To a solution of 2,2,6,6-tetramethylpiperidine (18.2 ml) in THF (160 ml) at −78° C. was added dropwise n-BuLi (43 ml, 2.5M solution in Hex). After the addition, the reaction mixture was stirred for 30 min at −78° C. To this solution was added intermediate 1.1 (6.17 g) in THF (20 ml) at −78° C. After addition, stirring was continued for 30 min. A solution of benzonitrile (4.67 ml) in THF (20 ml) at −78° C. was added dropwise. After addition, the mixture was slowly warmed to −50° C. and stirred for 20 min. The solution was poured into 10% aq. HCl (200 ml), stirred for 45 min at RT and neutralized with aq. NaOH to pH 9-10. The org. phase was separated, the aq. phase extracted twice with EA, and the combined org. phases dried over MgSO$_4$. CC (Hept/EA 1:1, then DCM/MeOH 95:5, then DCM/MeOH 8:2) afforded 1.96 g of the desired compound.

LC-MS (B): $t_R$=0.62 min; [M+H]$^+$: 186.2.

1.3. 4-chloro-2-methyl-6-phenyl-pyridine

Intermediate 1.2 (1.68 g) was suspended in POCl$_3$ (12 ml) and heated at 80° C. for 3 h. The reaction mixture was poured carefully onto ice water and extracted with DCM. The aq. phase was neutralized with Na$_2$CO$_3$ and washed with EA. The combined org. phases were dried over Na$_2$SO$_4$ and evaporated off to give 1.75 g of the desired compound.

LC-MS (B): $t_R$=0.81 min; [M+H]$^+$: 204.2.

1.4. 4-chloro-6-phenyl-pyridine-2-carboxylic acid

A solution of intermediate 1.3 (950 mg) and SeO$_2$ (776 mg) in dioxane (20 ml) was heated at reflux for 5 days. The reaction mixture was filtered over celite and evaporated off. The crude was dissolved in EtOH/H$_2$O (1:1, 140 ml), and NaOH (1.73 g) followed by AgNO$_3$ (2.30 g) were added. The reaction mixture was stirred for 2 h at RT, and then acidified with aq. HCl (1N). After filtration over celite, the org. solvent was removed in vacuo. The aq. phase was extracted with EA, dried over MgSO$_4$ and evaporated off. The desired compound (0.88 g) was used without further purification.

LC-MS (B): $t_R$=0.89 min; [M+H]$^+$: 234.2.

1.5. 4-((S)-2-benzyloxycarbonylamino-4-tert-butoxycarbonyl-butyryl)-piperazine-1-carboxylic acid ethyl ester To a solution of Z-(L)Glu(OtBu)-OH (5 g) in DCM/THF (1:1, 42 ml) were added at RT HOBT (2.5 g) and EDCI (3.1 g). After 15 min stirring at RT, 1-ethoxycarbonylpiperazine (2.6 g) was added and the stirring was continued at RT overnight. 150 ml of EA and 60 ml of a NaHCO$_3$ solution were added to the reaction mixture and the phases were separated. The org. phase was washed with an aq. NaHSO$_4$ (1M) solution and with brine, dried over Na$_2$SO$_4$ and evaporated off. After HV drying, 7 g of the desired compound were obtained.

LC-MS (A): $t_R$=1.12 min; [M+H]$^+$: 478.12.

1.6. 4-((S)-2-amino-4-tert-butoxycarbonyl-butyryl)-piperazine-1-carboxylic acid ethyl ester Intermediate 1.5 (7 g) was hydrogenated in EtOH (17 ml) with Pd/C (10%, 350 mg) for 24 h. The mixture was filtered through celite and evaporated off. HV drying afforded 5.3 g of the desired compound.

LC-MS (A): $t_R$=0.66 min; [M+H]$^+$: 344.06.

1.7. 4-{(S)-4-O-tert-butoxycarbonyl-2-[(4-chloro-6-phenyl-pyridine-2-carbonyl)-amino]-butyryl}-piperazine-1-carboxylic acid ethyl ester To a solution of intermediate 1.4 (900 mg) in DCM (30 ml) was added PyBOP (2.2 g), and the reaction mixture stirred for 10 min at RT. Intermediate 1.6 (1.32 g), and DIPEA (0.79 ml) were added and the mixture stirred overnight at RT. The reaction mixture was washed twice with aq. Na$_2$CO$_3$ (2N) and once with brine. The combined aq. phases were extracted with DCM, the org. phases dried over Na$_2$SO$_4$ and evaporated off. Purification by CC (EA/Hept 1:1) gave 1.2 g of the desired compound.

LC-MS (B): $t_R$=1.07 min; [M+H]$^+$: 559.3.

1.8. 4-{(S)-4-carboxy-2-[(4-chloro-6-phenyl-pyridine-2-carbonyl)-amino]-butyryl}-piperazine-1-carboxylic acid ethyl ester To a solution of intermediate 1.7 (500 mg) in DCM (10 ml) was added TFA (1.72 ml) at RT. The reaction mixture was stirred for 2 h at RT and the solvent evaporated off. CC (DCM/MeOH 95/5 to 90/10) gave 420 mg of the desired compound.

LC-MS (B): $t_R$=0.93 min; [M+H]$^+$: 503.5.

Example 2

4-{(S)-4-carboxy-2-[(6-chloro-4-phenyl-pyridine-2-carbonyl)-amino]-butyryl}-piperazine-1-carboxylic acid ethyl ester

2.1. 2-cyano-4-phenylpyridine

To a solution of 4-phenylpyridine N-oxide (5 g) in DCM (50 ml) was added at RT TMSCN (4 ml), and the solution was stirred for 5 min at RT. Then, dimethylcarbamoyl chloride (2.8 ml) was added at RT, and the resulting solution was stirred at RT for 48 h. To the reaction mixture was added a solution of aq. 10% K$_2$CO$_3$ (50 ml) and stirring was continued for 10 min. The phases were separated and the aq. layer extracted twice with DCM. The combined org. phases were dried over MgSO$_4$ and evaporated off. Filtration over a plug of SiO$_2$ (Hept/EA 8:2) gave 4.98 g of the desired compound.

LC-MS (B): $t_R$=0.91 min; [M+H]$^+$: 181.2.

2.2. 1-oxy-4-phenyl-pyridine-2-carbonitrile

MCPBA (4.88 g) was added to a solution of intermediate 2.1 (3.40 g) in DCM (80 ml) at RT. The reaction mixture was stirred 30 min at RT, then heated to 40-45° C. overnight. Another batch of MCPBA (1.63 g) was added, and the reaction mixture heated at reflux for 6 h and over for 48 h at RT. The reaction was quenched at 0° C. with aq. 40% NaHSO$_3$, and the mixture filtered off. The solid was washed with sat. aq. Na$_2$CO$_3$, H$_2$O, and DCM. The mother liquor was treated with aq. sat. Na$_2$CO$_3$, filtered, and the solid washed with H$_2$O. The desired compound (3.76 g) was used without further purification in the next step.

LC-MS (B): $t_R$=0.77 min; [M+H]$^+$: 238.3.

2.3. 6-chloro-4-phenyl-pyridine-2-carbonitrile

To intermediate 2.2 (3.76 g) was added at RT POCl$_3$ (50 ml) at once, and the suspension stirred at reflux for 30 min. The reaction mixture was transferred carefully to H$_2$O for quench. The aq. phase was extracted with DCM. The combined org. phases were washed with brine, dried over MgSO$_4$ and evaporated off to give 3.08 g of the desired compound.

LC-MS (B): $t_R$=1.00 min; [M+H+CH$_3$CN]$^+$: 256.3.

2.4. 6-chloro-4-phenyl-pyridine-2-carboxylic acid

Intermediate 2.3 (1.45 g) in conc. HCl (50 ml) was heated to reflux for 150 min. The reaction mixture was added to a conc. NaOH solution and the pH adjusted to 4-5. The aq. phase was extracted with EA, acidified with conc. HCl and extracted again with EA. The combined organic layers were dried over MgSO$_4$ and evaporated off to give 1.56 g of the desired compound.

LC-MS (B): $t_R$=0.85 min; [M+H]$^+$: 234.3.

2.5. 4-{(S)-4-tert-butoxycarbonyl-2-[(6-chloro-4-phenyl-pyridine-2-carbonyl)-amino]-butyryl}-piperazine-1-carboxylic acid ethyl ester To a solution of intermediate 2.4 (1.24 g) in DCM (20 ml), was added DIPEA (1.82 ml), then PyBOP (3.32 g). The mixture was stirred 15 min at RT, then the intermediate 1.6 (2.01 g) in DCM (10 ml) was added, and the reaction mixture stirred on at RT. The org. solvent was evaporated off, the residue taken up in EA. The org. phase was washed with sat.

aq. NaHCO$_3$, with sat. aq. NH$_4$Cl, dried over MgSO$_4$ and evaporated off. CC (Hept/EA 8:2, then 7:3) yielded 1.73 g of the desired compound.

LC-MS (B): $t_R$=1.07 min; [M+H]$^+$: 559.4.

2.6. 4-{(S)-4-carboxy-2-[(6-chloro-4-phenyl-pyridine-2-carbonyl)-amino]-butyryl}-piperazine-1-carboxylic acid ethyl ester This compound was prepared using a method analogous to that of Example 1, step 1.8, intermediate 2.5 replacing intermediate 1.7.

LC-MS (B): $t_R$=0.93 min; [M+H]$^+$: 503.4.

Example 3

4-{(S)-4-carboxy-2-[(4-cyclopentyloxy-6-phenyl-pyridine-2-carbonyl)-amino]-butyryl}-piperazine-1-carboxylic acid ethyl ester

3.1. 4-cyclopentyloxy-2-methyl-6-phenyl-pyridine

To a solution of intermediate 1.2 (400 mg) in DMF (15 ml) was added Cs$_2$CO$_3$ (1.76 g), followed by cyclopentylbromide (0.58 ml) at RT, and the reaction mixture heated to 50° C. overnight. After cooling to RT, the reaction mixture was diluted with H$_2$O and extracted twice with EA. The combined org. phases were washed with brine, dried over MgSO$_4$, and evaporated off to give 0.43 g of the desired solid.

LC-MS (B): $t_R$=1.11 min.
$^1$H-NMR (CDCl$_3$): 7.9 (d, 2H); 7.35-7.46 (m, 3H); 7.0 (d, 1H); 6.6 (d, 1H); 4.86 (m, 1H); 2.6 (s, 3H); 1.6-2.0 (m, 8H).

3.2. 4-cyclopentyloxy-6-phenyl-pyridine-2-carboxylic acid

To a solution of intermediate 3.1 (400 mg) in pyridine (10 ml) was added SeO$_2$ (210 mg) at RT. The reaction mixture was stirred at reflux overnight, subsequently filtered off over Celite, and aq. NaOH (1M) was added to the filtrate to reach pH=9-10. The aq. phase was acidified with HCl (2M) and extracted with EA. The combined org. phases were dried over MgSO$_4$ and evaporated off to give 430 mg of the desired compound.

LC-MS (B): $t_R$=0.85 min; [M+H]$^+$: 284.0.

3.3. 4-{(S)-4-tert-butoxycarbonyl-2-[(4-cyclopentyloxy-6-phenyl-pyridine-2-carbonyl)-amino]-butyryl}-piperazine-1-carboxylic acid ethyl ester To a solution of intermediate 3.2 (450 mg) in DCM (5 ml) was added HOBT (322 mg) followed by EDCI (365 mg) at RT. After 15 min stirring, intermediate 1.6 (545 mg) in DCM (2 ml) was added and the reaction mixture stirred at RT for 4 h. The reaction mixture was washed with sat. aq. NH$_4$Cl and with brine. The org. phase was dried over MgSO$_4$ and evaporated off. CC (Hept/EA 1/1 to 3/7) gave 600 mg of the desired compound.

LC-MS (B): $t_R$=1.14 min; [M+H]$^+$: 609.4.

3.4 4-{(S)-4-carboxy-2-[(4-cyclopentyloxy-6-phenyl-pyridine-2-carbonyl)-amino]-butyryl}-piperazine-1-carboxylic acid ethyl ester This compound was prepared using a method analogous to that of Example 1, step 1.8, intermediate 3.3 replacing intermediate 1.7.

LC-MS (B): $t_R$=0.98 min; [M+H]$^+$: 553.4.

Example 4

4-((S)-4-carboxy-2-{[4-(1-hydroxy-1-methyl-ethyl)-6-phenyl-pyridine-2-carbonyl]-amino}-butyryl)-piperazine-1-carboxylic acid ethyl ester

4.1. 4-((S)-4-tert-butoxycarbonyl-2-{[4-(1-ethoxy-vinyl)-6-phenyl-pyridine-2-carbonyl]-amino}-butyryl)-piperazine-1-carboxylic acid ethyl ester To intermediate 1.7 (400 mg) and (1-ethoxyvinyl)-tributyl-stannane (0.36 ml) was added toluene (10 ml) and the solution was stirred at RT under argon for 5 min. Pd(PPh$_3$)$_4$ (84 mg) was then added and the stirring was continued for 3 h at reflux. The reaction mixture was filtered off through Celite and evaporated off. CC (Hept/EA 1:1) yielded 420 mg of the desired compound.

LC-MS (B): $t_R$=1.11 min; [M+H]$^+$: 595.5.

4.2. 4-{(S)-2-[(4-acetyl-6-phenyl-pyridine-2-carbonyl)-amino]-4-tert-butoxycarbonyl-butyryl}-piperazine-1-carboxylic acid ethyl ester To a solution of intermediate 4.1 (420 mg) in acetone (4 ml) was added aq HCl (1M, 0.92 ml) at RT and the reaction mixture heated to reflux for 1 h. The solvent was evaporated off and the residue taken up in sat. aq. NaHCO$_3$. The aq. phase was extracted with EA, the combined org. phases were dried over MgSO$_4$ and evaporated off. The desired crude compound (380 mg) was used without further purification in the next step.

LC-MS (B): $t_R$=1.03 min; [M+H]$^+$: 567.5.

4.3. 4-((S)-4-tert-butoxycarbonyl-2-{[4-(1-hydroxy-1-methyl-ethyl)-6-phenyl-pyridine-2-carbonyl]-amino}-butyryl)-piperazine-1-carboxylic acid ethyl ester To a solution of intermediate 4.2 (380 mg) in Et$_2$O (5 ml) at −20° C. was added MeMgBr (0.45 ml, as 3 M solution in Et$_2$O) dropwise and the reaction mixture warmed up to RT for 2 h. The reaction mixture was quenched with sat. aq. NH$_4$Cl, and the aq. phase extracted with EA. The combined org. phases were dried over MgSO$_4$ and evaporated off. CC (Hept/EA 1:1) gave 165 mg of the desired compound.

LC-MS (B): $t_R$=0.99 min; [M+H]$^+$: 583.52.

4.4. 4-((S)-4-carboxy-2-{[4-(1-hydroxy-1-methyl-ethyl)-6-phenyl-pyridine-2-carbonyl]-amino}-butyryl)-piperazine-1-carboxylic acid ethyl ester This compound was prepared using a method analogous to that of Example 1, step 1.8, intermediate 2.5 replacing intermediate 1.7. Additionally, the compound was purified by preparative LC-MS (IV).

LC-MS (B): $t_R$=0.84 min; [M+H]$^+$: 527.4.

Example 5

4-{(S)-4-carboxy-2-[(4,6-diphenyl-pyridine-2-carbonyl)-amino]-butyryl}-piperazine-1-carboxylic acid ethyl ester

5.1. 2-methyl-4,6-diphenyl-pyridine

To a suspension of intermediate 1.3 (2.1 g) and Pd(PPh$_3$)$_4$ (0.33 g) in DME (15 ml) were added aq. K$_2$CO$_3$ (10.3 ml, 2M) followed by a suspension of phenylboronic acid (1.64 g) in EtOH (1 ml). The mixture was heated to 90° C. for 2 h, filtered over Celite and the solvent evaporated off. CC (Hept/EA 95:5) gave 0.12 g of the desired compound.
LC-MS (B): t$_R$=0.80 min; [M+H]$^+$: 246.0.

5.2. 4,6-diphenyl-pyridine-2-carboxylic acid

To intermediate 5.1 (120 mg) in pyridine (5 ml) was added SeO$_2$ (120 mg) at RT and the reaction mixture heated to reflux for 48 h. H$_2$O was added, the reaction mixture filtered through Celite, and the Celite washed with EA. The org. phase was separated, dried over MgSO$_4$ and evaporated to dryness. CC (EA/Hept 7:3 to EA/MeOH 95:5) gave 25 mg of the desired compound.
LC-MS (B): t$_R$=0.96 min; [M+H]$^+$: 276.2.

5.3. 4-{(S)-4-tert-butoxycarbonyl-2-[(4,6-diphenyl-pyridine-2-carbonyl)-amino]-butyryl}-piperazine-1-carboxylic acid ethyl ester This compound was prepared using a method analogous to that of Example 3, step 3.3, intermediate 5.2 replacing intermediate 3.2.
LC-MS (B): t$_R$=1.10 min; [M+H]$^+$: 601.3.

5.4. 4-{(S)-4-carboxy-2-[(4,6-diphenyl-pyridine-2-carbonyl)-amino]-butyryl}-piperazine-1-carboxylic acid ethyl ester To a solution of intermediate 5.3 (54 mg) in DCM (2 ml) was added TFA (1 ml) at RT. The reaction mixture was stirred at RT for 2 h. Evaporation of the solvent and purification by preparative LC-MS (IV) provided 15 mg of the desired compound.
LC-MS (B): t$_R$=0.97 min; [M+H]$^+$: 545.2.

Example 6

4-{(S)-4-carboxy-2-[(6-phenyl-4-pyrazol-1-yl-pyridine-2-carbonyl)-amino]-butyryl}-piperazine-1-carboxylic acid ethyl ester

6.1. 2-methyl-6-phenyl-4-pyrazol-1-yl-pyridine

To a solution of pyrazole (290 mg) in abs. DMF (5 ml) was added at RT NaH (186 mg, 55% in mineral oil). After stirring for 5 min at RT, intermediate 1.3 (174 mg) was added and the reaction mixture stirred overnight at 120° C. Sat aq. NH$_4$Cl was added, followed by H$_2$O, and the aq. phase extracted with EA. The combined org. phases were dried over MgSO$_4$ and evaporated off. CC (Hept/EA 1:1) gave 195 mg of the desired compound.
LC-MS (B): t$_R$=0.68 min; [M+H]$^+$: 236.1.

6.2. 6-phenyl-4-pyrazol-1-yl-pyridine-2-carboxylic acid

This compound was prepared using a method analogous to that of Example 5, step 5.2, intermediate 6.1 replacing intermediate 5.1.
LC-MS (B): t$_R$=0.87 min; [M+H]$^+$: 266.0.

6.3. 4-{(S)-4-tert-butoxycarbonyl-2-[(6-phenyl-4-pyrazol-1-yl-pyridine-2-carbonyl)-amino]-butyryl}-piperazine-1-carboxylic acid ethyl ester To a solution of intermediate 6.2 (54 mg) in DMF (1 ml) was added at RT TBTU (85 mg) followed by DIPEA (0.1 ml) and intermediate 1.6 (140 mg). After stirring 3 h at RT, the reaction mixture was evaporated off and directly purified by CC (Hept/EA) 1:1 to give 60 mg of the desired compound.
LC-MS (B): t$_R$=1.06 min; [M+H]$^+$: 591.5.

6.4 4-{(S)-4-carboxy-2-[(6-phenyl-4-pyrazol-1-yl-pyridine-2-carbonyl)-amino]-butyryl}-piperazine-1-carboxylic acid ethyl ester This compound was prepared using a method analogous to that of Example 1, step 1.8, intermediate 2.5 replacing intermediate 1.7.
LC-MS (B): t$_R$=0.89 min; [M+H]$^+$: 535.2.

Example 7

4-((S)-4-carboxy-2-{[4-(4-methoxy-phenyl)-6-phenyl-pyridine-2-carbonyl]-amino}-butyryl)-piperazine-1-carboxylic acid ethyl ester

7.1. 4-((S)-4-tert-butoxycarbonyl-2-{[4-(4-methoxy-phenyl)-6-phenyl-pyridine-2-carbonyl]-amino}-butyryl)-piperazine-1-carboxylic acid ethyl ester A mixture of intermediate 1.7 (100 mg), 4-methoxyphenylboronic acid (33 mg), Pd(PPh$_3$)$_4$ (6 mg), aq. K$_2$CO$_3$ (0.18 ml, 2M) in DME was heated at 90° C. for 48 h. The reaction mixture was filtered over celite and the solvent evaporated off. CC (Hept/EA 85/15) gave 51 mg of the desired compound together with some dehalogenated side-product (20%). The mixture was engaged without further purification in the next step.
LC-MS (B): t$_R$=1.10 min; [M+H]$^+$: 631.6.

7.2. 4-((S)-4-carboxy-2-{[4-(4-methoxy-phenyl)-6-phenyl-pyridine-2-carbonyl]-amino}-butyryl)-piperazine-1-carboxylic acid ethyl ester This compound was prepared using a method analogous to that of Example 5, step 5.4, intermediate 7.1 replacing intermediate 5.3.
LC-MS (B): t$_R$=0.98 min; [M+H]$^+$: 575.4.

Example 8

4-((S)-4-carboxy-2-{[4-cyclopropyl-6-phenyl-pyridine-2-carbonyl]-amino}-butyryl)-piperazine-1-carboxylic acid ethyl ester

8.1. 4-((S)-4-tert-butoxycarbonyl-2-{[4-cyclopropyl-6-phenyl-pyridine-2-carbonyl]-amino}-butyryl)-piperazine-1-carboxylic acid ethyl ester This compound was prepared using a method analogous to that of Example 7, step 7.1, cyclopropylboronic acid replacing 4-methoxyphenylboronic acid.
LC-MS (B): $t_R$=1.07 min; [M+H]$^+$: 565.5.

8.2. 4-((S)-4-carboxy-2-{[4-cyclopropyl-6-phenyl-pyridine-2-carbonyl]-amino}-butyryl)-piperazine-1-carboxylic acid ethyl ester This compound was prepared using a method analogous to that of Example 5, step 5.4, intermediate 8.1 replacing intermediate 5.3. However, the compound was purified by preparative LC-MS (III).
LC-MS (B): $t_R$=0.93 min; [M+H]$^+$: 509.4.

Example 9

4-{(S)-2-[(4-butyl-6-phenyl-pyridine-2-carbonyl)-amino]-4-carboxy-butyryl}-piperazine-1-carboxylic acid ethyl ester 9.1. 4-{(S)-4-tert-butoxycarbonyl-2-[(4-butyl-6-phenyl-pyridine-2-carbonyl)-amino]-butyryl}-piperazine-1-carboxylic acid ethyl ester This compound was prepared using a method analogous to that of Example 7, step 7.1, butylboronic acid replacing 4-methoxyphenylboronic acid.
LC-MS (B): $t_R$=1.13 min; [M+H]$^+$: 581.5.

9.2. 4-{(S)-2-[(4-butyl-6-phenyl-pyridine-2-carbonyl)-amino]-4-carboxy-butyryl}-piperazine-1-carboxylic acid ethyl ester This compound was prepared using a method analogous to that of Example 5, step 5.4, intermediate 9.1 replacing intermediate 5.3.
LC-MS (B): $t_R$=0.99 min; [M+H]$^+$: 525.5.

Example 10

4-((S)-4-carboxy-2-{[6-(2-fluoro-phenyl)-4-phenyl-pyridine-2-carbonyl]-amino}-butyryl)-piperazine-1-carboxylic acid ethyl ester A mixture of intermediate 2.6 (50 mg), 2-fluorophenylboronic acid (70 mg), Pd(PPh$_3$)$_4$ (6 mg), aq. K$_2$CO$_3$ (0.1 ml, 2M) in DME (2 ml) was heated under argon in a sealed vial at 120° C. for 30 min. The reaction mixture was filtered over celite and the solvent evaporated off. Preparative LC-MS (IV) gave 26 mg of the desired compound.
LC-MS (B): $t_R$=0.99 min; [M+H]$^+$: 563.4.

Example 11

4-((S)-4-carboxy-2-{[6-(4-fluoro-phenyl)-4-phenyl-pyridine-2-carbonyl]-amino}-butyryl)-piperazine-1-carboxylic acid ethyl ester This compound was prepared using a method analogous to that of Example 10, 4-fluorophenylboronic acid replacing 2-fluorophenylboronic acid.
LC-MS (B): $t_R$=1.00 min; [M+H]$^+$: 563.4.

Example 12

4-{(S)-4-carboxy-2-[(4-phenyl-6-o-tolyl-pyridine-2-carbonyl)-amino]-butyryl}-piperazine-1-carboxylic acid ethyl ester This compound was prepared using a method analogous to that of Example 10, o-tolylboronic acid replacing 2-fluorophenylboronic acid. It was however purified by preparative LC-MS (V).
LC-MS (B): $t_R$=1.00 min; [M+H]$^+$: 559.4.

Example 13

4-{(S)-4-carboxy-2-[(4-phenyl-6-p-tolyl-pyridine-2-carbonyl)-amino]-butyryl}-piperazine-1-carboxylic acid ethyl ester This compound was prepared using a method analogous to that of Example 10, p-tolylboronic acid replacing 2-fluorophenylboronic acid. It was however purified by preparative LC-MS (V).
LC-MS (B): $t_R$=1.01 min; [M+H]$^+$: 559.4.

Example 14

4-((S)-4-carboxy-2-{[4-((R)-3-hydroxy-pyrrolidin-1-yl)-6-phenyl-pyridine-2-carbonyl]-amino}-butyryl)-piperazine-1-carboxylic acid ethyl ester 14.1. 4-{(S)-4-O-tert-butoxycarbonyl-2-[(4-[(R)-3-hydroxy-pyrrolidin-1-yl]-6-phenyl-pyridine-2-carbonyl)-amino]-butyryl}-piperazine-1-carboxylic acid ethyl ester A mixture of intermediate 1.7 (100 mg) and (R)-3-pyrrolidinol (62 mg) in THF was heated under microwave irradiation at 160° C. until completion of the reaction. The solvent was evaporated off and the crude directly subjected to CC (Hept/EA 1:1) to provide 60 mg of the desired compound.
LC-MS (B): $t_R$=0.81 min; [M+H]$^+$: 609.7.

14.2. 4-((S)-4-carboxy-2-{[4-((R)-3-hydroxy-pyrrolidin-1-yl)-6-phenyl-pyridine-2-carbonyl]-amino}-butyryl)-piperazine-1-carboxylic acid ethyl ester This compound was prepared using a method analogous to that of Example 1, step 1.8, intermediate 14.1 replacing intermediate 1.7.
LC-MS (B): $t_R$=0.69 min; [M+H]$^+$: 554.4.

Example 15

4-{(S)-4-carboxy-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester 15.1. 4-{(S)-4-tert-butoxycarbonyl-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester This compound was prepared using a method analogous to that of Example 14, step 14.1, 4-hydroxypiperidine replacing (R)-3-pyrrolidinol.
LC-MS (B): $t_R$=0.83 min; [M+H]$^+$: 624.5.

15.2. 4-{(S)-4-carboxy-2-[(4-hydroxy-6'-phenyl-3,4, 5,6-tetrahydro-2H-[1,4']bipyridinyl-2'-carbonyl)-amino]-butyryl}-piperazine-1-carboxylic acid ethyl ester This compound was prepared using a method analogous to that of Example 1, step 1.8, intermediate 15.1 replacing intermediate 1.7.

LC-MS (B): $t_R$=0.76 min; $[M+H]^+$: 568.4.

Example 16

4-{(S)-4-carboxy-2-[(6-phenyl-4-pyrrolidin-1-yl-pyridine-2-carbonyl)-amino]-butyryl}-piperazine-1-carboxylic acid ethyl ester

16.1. 4-{(S)-4-tert-butoxycarbonyl-2-[(6-phenyl-4-pyrrolidin-1-yl-pyridine-2-carbonyl)-amino]-butyryl}-piperazine-1-carboxylic acid ethyl ester This compound was prepared using a method analogous to that of Example 14, step 14.1, pyrrolidine replacing (R)-3-pyrrolidinol.

LC-MS (B): $t_R$=0.89 min; $[M+H]^+$: 594.5.

16.2. 4-{(S)-4-carboxy-2-[(6-phenyl-4-pyrrolidin-1-yl-pyridine-2-carbonyl)-amino]-butyryl}-piperazine-1-carboxylic acid ethyl ester This compound was prepared using a method analogous to that of Example 1, step 1.8, intermediate 16.1 replacing intermediate 1.7.

LC-MS (B): $t_R$=0.74 min; $[M+H]^+$: 538.4.

Example 17

4-((S)-4-carboxy-2-{[4-(2-hydroxy-ethylamino)-6-phenyl-pyridine-2-carbonyl]-amino}-butyryl)-piperazine-1-carboxylic acid ethyl ester

17.1. 4-((S)-4-tert-butoxycarbonyl-2-{[4-(2-hydroxy-ethylamino)-6-phenyl-pyridine-2-carbonyl]-amino}-butyryl)-piperazine-1-carboxylic acid ethyl ester This compound was prepared using a method analogous to that of Example 14, step 14.1, ethanolamine replacing (R)-3-pyrrolidinol and the reaction mixture being heated at 180° C. under microwave irradiation for further 12 h.

LC-MS (B): $t_R$=0.89 min; $[M+H]^+$: 584.5.

17.2. 4-((S)-4-carboxy-2-{[4-(2-hydroxy-ethylamino)-6-phenyl-pyridine-2-carbonyl]-amino}-butyryl)-piperazine-1-carboxylic acid ethyl ester This compound was prepared using a method analogous to that of Example 1, step 1.8, intermediate 16.1 replacing intermediate 1.7. Additionally, the compound was further purified by precipitation and filtration from pentane.

LC-MS (B): $t_R$=0.67 min; $[M+H]^+$: 528.5.

Example 18

4-((S)-4-carboxy-2-{[4-((S)-3-methoxy-pyrrolidin-1-yl)-6-phenyl-pyridine-2-carbonyl]-amino}-butyryl)-piperazine-1-carboxylic acid ethyl ester

18.1. 4-((S)-4-tert-butoxycarbonyl-2-{[4-((S)-3-hydroxy-pyrrolidin-1-yl)-6-phenyl-pyridine-2-carbonyl]-amino}-butyryl)-piperazine-1-carboxylic acid ethyl ester This compound was prepared using a method analogous to that of Example 14, step 14.1, (S)-3-pyrrolidinol replacing (R)-3-pyrrolidinol.

LC-MS (B): $t_R$=0.81 min; $[M+H]^+$: 610.5.

18.2. 4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid ethyl ester To a solution of intermediate 18.1 (80 mg) in THF (1 ml) was added NaH (24 mg, 55% in mineral oil) at RT. The reaction mixture was stirred for 10 min at RT, then MeI (0.01 ml) was added. Stirring was continued for additional 2 h. The reaction mixture was diluted with DCM and washed with $H_2O$. The organic phase was dried over $MgSO_4$ and evaporated off. Purification by preparative LC-MS (IV) gave 25 mg of the desired compound.

LC-MS (B): $t_R$=0.88 min; $[M+H]^+$: 624.6.

18.3. 4-((S)-4-carboxy-2-{[4-((S)-3-methoxy-pyrrolidin-1-yl)-6-phenyl-pyridine-2-carbonyl]-amino}-butyryl)-piperazine-1-carboxylic acid ethyl ester This compound was prepared using a method analogous to that of Example 1, step 1.8, intermediate 18.2 replacing intermediate 1.7. However, the compound was purified by preparative LC-MS (II).

LC-MS (B): $t_R$=0.75 min; $[M+H]^+$: 568.5.

Example 19

4-{(S)-4-carboxy-2-[(4-isopropylamino-6-phenyl-pyridine-2-carbonyl)-amino]-butyryl}-piperazine-1-carboxylic acid ethyl ester

19.1. 4-{(S)-4-tert-butoxycarbonyl-2-[(4-isopropylamino-6-phenyl-pyridine-2-carbonyl)-amino]-butyryl}-piperazine-1-carboxylic acid ethyl ester A mixture of intermediate 1.7 (100 mg), isopropylamine (0.018 ml), acetato(2'-di-t-butylphosphino-1,1'-biphenyl-2-yl)palladium (0.8 mg), KOH (15 mg) in toluene (2 ml) was heated at 90° C. overnight. The reaction mixture was filtered through celite and the solvent evaporated off. CC (Hept/EA 7:3) gave 58 mg of the desired compound.

LC-MS (B): $t_R$=0.87 min; $[M+H]^+$: 582.5.

19.2. 4-{(S)-4-carboxy-2-[(4-isopropylamino-6-phenyl-pyridine-2-carbonyl)-amino]-butyryl}-piperazine-1-carboxylic acid ethyl ester This compound was prepared using a method analogous to that of Example 1, step 1.8, intermediate 19.1 replacing intermediate 1.7. However, the compound was purified by preparative LC-MS (IV).

LC-MS (B): $t_R$=0.76 min; [M+H]$^+$: 526.4.

Example 20

4-((S)-4-carboxy-2-{[4-(2-methoxymethyl-cyclopropyl)-6-phenyl-pyridine-2-carbonyl]-amino}-butyryl)-piperazine-1-carboxylic acid ethyl ester 20.1. (E)-3-tributylstannanyl-prop-2-en-1-ol To neat propargyl alcohol (1 ml) were added tributyltin hydride (5.8 ml) followed by 1,1'-azobis(cyclohexanecarbonitrile) (213 mg). The mixture was heated for 2 h at 80° C., cooled to RT and directly purified by CC (EA/Hept 4/96 to 5/95) to afford 2.98 g of the desired compound.

$^1$H-NMR (CDCl$_3$): 6.2 (m, 2H); 4.15 (m, 2H); 1.55-1.25 (m, 18H); 0.90 (t, 9H).

20.2. Trans-(2-tributylstannanyl-cyclopropyl)-methanol

To a stirred solution of diethylzinc (3.32 ml, 1M in hexane) in abs. DCM (5 ml) at 0° C. was added diiodomethane (538 ml). The mixture was stirred at 0° C. for 10 min and a solution of intermediate 20.1 (514 mg) in DCM (10 ml) was added slowly. The mixture was stirred at RT for 2 h, cooled down to 0° C. and quenched with a sat. aq. NH$_4$Cl solution. The org. phase was separated and the aq. phase extracted with EA. The combined org. phases were dried over Na$_2$SO$_4$ and evaporated off. CC (EA/Hept 5/95) gave 434 mg of the desired compound.

$^1$H-NMR (CDCl$_3$): 3.52-3.60 (m, 1H); 3.37-3.43 (m, 1H); 1.55-1.25 (m, 13H); 1.10 (m, 1H); 0.90 (t, 9H); 0.75 (m, 1H); 0.51-0.57 (m, 2H); −0.35--0.28 (m, 1H).

20.3. Trans-tributyl-(2-methoxymethyl-cyclopropyl)-stannane

To a solution of intermediate 20.2 (600 mg) in THF (20 ml) was added NaH (104 mg, 60% in mineral oil) at RT, and the mixture stirred 30 min at RT. MeI (0.5 ml) was added at 0° C. and stirring was continued at RT overnight. The reaction mixture was quenched with MeOH and evaporated off. The crude was diluted with H$_2$O and extracted with DCM. The combined org. phases were dried over MgSO$_4$ and evaporated off. CC (Hept/EA 95:5) gave 353 mg of the desired compound.

$^1$H-NMR (CDCl$_3$): 3.42-3.48 (dd, 1H); 3.38 (s, 3H); 3.08-3.14 (dd, 1H); 1.55-1.25 (m, 18H); 1.10 (m, 1H); 0.90 (t, 9H); 0.51-0.57 (m, 2H); −0.35--0.28 (m, 1H).

20.4. 4-((S)-4-tert-butoxycarbonyl-2-{[4-(2-methoxymethyl-cyclopropyl)-6-phenyl-pyridine-2-carbonyl]-amino}-butyryl)-piperazine-1-carboxylic acid ethyl ester A mixture of intermediate 1.7 (100 mg), intermediate 20.3 (101 mg), Pd(PPh$_3$)$_4$ (10 mg) in degassed toluene (3 ml) was heated at 130° C. in a sealed vial until reaction completion.

The crude mixture was filtered over Celite, evaporated off and directly purified by CC (Hept/EA 5.6/4.4 to 1:1) to give 78 mg of the desired compound.

LC-MS (B): $t_R$=1.06 min; [M+H]$^+$: 609.6.

20.5. 4-((S)-4-carboxy-2-{[4-(2-methoxymethyl-cyclopropyl)-6-phenyl-pyridine-2-carbonyl]-amino}-butyryl)-piperazine-1-carboxylic acid ethyl ester This compound was prepared using a method analogous to that of Example 1, step 1.8, intermediate 20.4 replacing intermediate 1.7.

LC-MS (B): $t_R$=0.93 min; [M+H]$^+$: 553.3.

Example 21

4-((S)-4-carboxy-2-{[4-(2-hydroxymethyl-cyclopropyl)-6-phenyl-pyridine-2-carbonyl]-amino}-butyryl)-piperazine-1-carboxylic acid ethyl ester 21.1. 4-((S)-4-tert-butoxycarbonyl-2-{[4-(2-hydroxymethyl-cyclopropyl)-6-phenyl-pyridine-2-carbonyl]-amino}-butyryl)-piperazine-1-carboxylic acid ethyl ester This compound was prepared using a method analogous to that of Example 20, step 20.4, intermediate 20.2 replacing intermediate 20.3.

LC-MS (B): $t_R$=1.01 min; [M+H]$^+$: 595.3.

21.2. 4-((S)-4-carboxy-2-{[4-(2-hydroxymethyl-cyclopropyl)-6-phenyl-pyridine-2-carbonyl]-amino}-butyryl)-piperazine-1-carboxylic acid ethyl ester To a solution of intermediate 21.1 (51 mg) in DCM (2 ml) was added TFA (1 ml), and the reaction mixture stirred for 3 h at RT. The reaction mixture was evaporated off, the residue taken up in MeOH (2 ml), and aq. LiOH (2 ml, 1N) was added in order to hydrolyse the trifluoroester. Stirring was continued for 4 h at RT. The reaction mixture was acidified with aq. HCl (1N), diluted with H$_2$O and extracted with EA. The combined org. phases were dried over MgSO$_4$ and evaporated off. CC (DCM/MeOH, 95:5, then 9:1, then DCM/MeOH/AcOH 95:5:0.33) and prep TLC (DCM/MeOH 9:1) gave 9 mg of the desired product.

LC-MS (B): $t_R$=0.84 min; [M+H]$^+$: 539.4.

Example 22

4-{(S)-3-cyano-2-[(4,6-diphenyl-pyridine-2-carbonyl)-amino]-propionyl}-piperazine-1-carboxylic acid ethyl ester 22.1. 4-((S)-2-tert-butoxycarbonylamino-3-cyano-propionyl)-piperazine-1-carboxylic acid ethyl ester To a solution of Boc-β-cyano-(L)-Ala-OH (566 mg) in THF/DCM (25 ml, 4:1) were added HOBT (428 mg) and EDCI (608 mg). After 5 min at RT, 1-(ethoxycarbonyl)piperazine (418 mg) was added and stirring was continued overnight at RT. The reaction mixture was diluted with EA and H$_2$O, the phases separated and the org. phase washed twice with aq. Na$_2$CO$_3$ (2M). The combined org. phases were dried over Na$_2$SO$_4$ and evaporated off to give 863 mg of the desired compound.

LC-MS (B): $t_R$=0.81 min; [M+H]$^+$: 355.2.

22.2. 4-((S)-2-amino-3-cyano-propionyl)-piperazine-1-carboxylic acid ethyl ester To a solution of intermediate 22.1 (863 mg) in EA (5 ml) was added HCl (5 ml, as 3N solution in EA) at RT. After 4 h, HCl (5 ml, as 3N solution in EA) was again added, and stirring was continued overnight. The reaction mixture was evaporated off, the crude taken up in Et$_2$O, filtered, and the precipitate washed with Et$_2$O and dried on HV to give 551 mg of the desired compound.

LC-MS (B): t$_R$=0.47 min; [M+H]$^+$: 255.3.

22.3. 4-{(S)-3-cyano-2-[(4,6-diphenyl-pyridine-2-carbonyl)-amino]-propionyl}-piperazine-1-carboxylic acid ethyl ester To a solution of intermediate 5.2 (200 mg) in DCM (2 ml) was added PyBOP (416 mg), and the reaction mixture stirred for 10 min at RT. Intermediate 22.2 (1.32 g), and DIPEA (0.79 ml) in DCM (1 ml) were added and the mixture stirred overnight at RT. The reaction mixture was diluted with DCM, washed with sat. aq. Na$_2$CO$_3$ and with brine. The combined aq. phases were extracted with DCM. The combined org. phases were dried over MgSO$_4$ and evaporated off. Purification by CC (EA/Hept 3:7 to 1:1) gave 215 mg of the desired compound.

LC-MS (B): t$_R$=1.03 min; [M+H]$^+$: 512.5.

Example 23

4-{(S)-4-carboxy-2-[(4,6-diphenyl-pyridine-2-carbonyl)-amino]-butyryl}-3-methyl-piperazine-1-carboxylic acid ethyl ester

23.1. 3-methyl-piperazine-1-carboxylic acid ethyl ester

To a solution of 2-methylpiperazine (1 g) in MeOH (12 ml) was added AcOH (1.8 ml). The mixture was cooled down to 0° C., ethyl chloroformate (0.95 ml) was added over a 60 min period. The mixture was allowed to warm to RT and was stirred overnight. Water was added and MeOH was evaporated off. The residue was extracted with toluene and the org. layers were washed with water. The combined aq. layers were basified to pH 14 with an aq. NaOH (2 M) solution and extracted with toluene. The combined org. layers were washed with brine, dried over Na$_2$SO$_4$ and evaporated off to give 936 mg of the desired compound.

$^1$H-NMR (CDCl$_3$): 4.1 (q, 2H); 3.95 (br s, 2H); 2.9 (d, 1H); 2.75 (m, 3H); 2.4 (t, 1H); 1.6 (br. s, 1H); 1.25 (t, 3H); 1.05 (t, 3H).

23.2. 4-((S)-2-benzyloxycarbonylamino-4-tert-butoxycarbonyl-butyryl)-3-ethyl-piperazine-1-carboxylic acid ethyl ester This compound was prepared using a method analogous to that of Example 22. step 22.1, intermediate 23.1 replacing 1-(ethoxycarbonyl)piperazine, and Z-(L)-Glu(OtBu)-OH replacing Boc-β-cyano-(L)-Ala-OH, but in DCM/THF (10 ml, 1:1).

LC-MS (B): t$_R$=0.92 min; [M+H]$^+$: 492.6.

23.3. 4-((S)-2-amino-4-tert-butoxycarbonyl-butyryl)-3-ethyl-piperazine-1-carboxylic acid ethyl ester To a solution of intermediate 23.2 (200 mg) in EtOH (6 ml) were added 4 drops of AcOH. The degassed reaction mixture was hydrogenated at RT (1 atm) for 1 h. The crude was filtered over Celite, evaporated off to give 142 mg of the desired compound.

LC-MS (B): t$_R$=0.70 min; [M+H]$^+$: 358.5.

23.4. 4-{(S)-4-tert-butoxycarbonyl-2-[(4,6-diphenyl-pyridine-2-carbonyl)-amino]-butyryl}-3-methyl-piperazine-1-carboxylic acid ethyl ester This compound was prepared using a method analogous to that of Example 22, step 22.3, intermediate 23.3 replacing intermediate 22.2.

LC-MS (B): t$_R$=1.12 min; [M+H]$^+$: 615.5.

23.5. 4-{(S)-4-carboxy-2-[(4,6-diphenyl-pyridine-2-carbonyl)-amino]-butyryl}-3-methyl-piperazine-1-carboxylic acid ethyl ester This compound was prepared using a method analogous to that of Example 5, step 5.4, intermediate 23.4 replacing intermediate 5.3. However, the compound was purified by preparative LC-MS (III).

LC-MS (B): t$_R$=0.99 min; [M+H]$^+$: 559.5.

Example 24

4-{(S)-2-[(4,6-diphenyl-pyridine-2-carbonyl)-amino]-3-hydroxy-propionyl}-piperazine-1-carboxylic acid ethyl ester

24.1. 4-((S)-2-benzyloxycarbonylamino-3-tert-butoxy-propionyl)-piperazine-1-carboxylic acid ethyl ester This compound was prepared using a method analogous to that of Example 1, step 1.5, Z-(L)-Ser-(tBu)-OH replacing Z-(L)Glu(OtBu)-OH.

LC-MS (A): t$_R$=1.08 min; [M+H]$^+$: 436.1.

24.2. 4-((S)-2-amino-3-tert-butoxy-propionyl)-piperazine-1-carboxylic acid ethyl ester This compound was prepared using a method analogous to that of Example 1, step 1.6, intermediate 24.1 replacing intermediate 1.5.

LC-MS (A): t$_R$=0.63 min; [M+H]$^+$: 302.2.

24.3. 4-{(S)-3-tert-butoxy-2-[(4,6-diphenyl-pyridine-2-carbonyl)-amino]-propionyl}-piperazine-1-carboxylic acid ethyl ester This compound was prepared using a method analogous to that of Example 22, step 22.3, intermediate 24.2 replacing 22.2.

LC-MS (B): t$_R$=1.11 min; [M+H]$^+$: 559.5.

24.4. 4-{(S)-2-[(4,6-diphenyl-pyridine-2-carbonyl)-amino]-3-hydroxy-propionyl}-piperazine-1-carboxylic acid ethyl ester To a solution of intermediate 24.3 (41 mg) in DCM (1 ml) was added TFA (0.4 ml), and the reaction mixture stirred for 3 h at RT. The reaction mixture was evaporated off, the residue taken up in MeOH (1 ml), and aq. LiOH (1 ml, 1N) was added in order to hydrolyse the trifluoroester. Stirring was continued for 2 h at RT. The solvent was evaporated off, and the residue directly purified by preparative LC-MS (III).
LC-MS (B): $t_R$=0.97 min; [M+H]$^+$: 503.5.

Example 25

4-{(S)-4-carboxy-2-[(4-phenyl-6-pyrazol-1-yl-pyridine-2-carbonyl)-amino]-butyryl}-piperazine-1-carboxylic acid ethyl ester

25.1. 4-phenyl-6-pyrazol-1-yl-pyridine-2-carbonitrile

To a solution of pyrazole (666 mg) in DMF (2 ml), was added at RT NaH (569 mg, 55% in mineral oil). After 15 min at RT a solution of intermediate 2.3 (700 mg) in DMF (2 ml) was added and the reaction mixture heated at 110° C. for 2 h. H$_2$O was added, and the aq. phase extracted with EA. The combined org phases were dried over MgSO$_4$ and the solvent was evaporated off to give 750 mg of the desired compound together with the corresponding amide (from partial hydrolysis of nitrile). The crude mixture was used without further purification in the next step.
LC-MS (B): $t_R$=1.02 min; [M+H]$^+$: 247.1.

25.2. 5-pyrazol-1-yl-biphenyl-3-carboxylic acid

Conc. HCl (20 ml) was added to intermediate 25.1 (750 mg), and the suspension was heated to reflux for 30 min. The reaction mixture was diluted with H$_2$O and extracted with DCM/MeOH (9:1). The combined org. phases were dried over MgSO$_4$ and evaporated off to give 780 mg of the desired compound.
LC-MS (B): $t_R$=0.88 min; [M+H]$^+$: 266.3.

25.3. 4-{(S)-4-tert-butoxycarbonyl-2-[(4-phenyl-6-pyrazol-1-yl-pyridine-2-carbonyl)-amino]-butyryl}-piperazine-1-carboxylic acid ethyl ester This compound was prepared using a method analogous to that of Example 2, step 2.5, intermediate 25.2 replacing intermediate 2.4. However DMF was used as solvent and no CC was carried out.
LC-MS (B): $t_R$=1.08 min; [M+H]$^+$: 591.3.

25.4. 4-{(S)-4-carboxy-2-[(4-phenyl-6-pyrazol-1-yl-pyridine-2-carbonyl)-amino]-butyryl}-piperazine-1-carboxylic acid ethyl ester This compound was prepared using a method analogous to that of Example 1, step 1.8, intermediate 25.3 replacing intermediate 1.7. Additionally, the compound was purified by preparative LC-MS (IV).
LC-MS (B): $t_R$=0.81 min; [M+H]$^+$: 535.4.

Example 26

4-((S)-4-carboxy-2-{[4-(3-hydroxy-propyl)-6-phenyl-pyridine-2-carbonyl]-amino}-butyryl)-piperazine-1-carboxylic acid ethyl ester

26.1. 4-((S)-4-tert-butoxycarbonyl-2-{[4-(3-hydroxy-prop-1-ynyl)-6-phenyl-pyridine-2-carbonyl]-amino}-butyryl)-piperazine-1-carboxylic acid ethyl ester NEt$_3$ (75 μl) and propargyl alcohol (32 μl) in DMF (1.35 ml) were syringed into a flask containing cupper iodide (2.75 mg), bis-(triphenylphosphine) palladium(II)-dichloride (6.96 mg) and intermediate 1.7 (151 mg) under argon. The mixture was allowed to stir at RT overnight. As the reaction was not complete, the same amount of each reagent was added to the mixture which was heated at 60° C. for 36 h. The solvent was evaporated off and the residue chromatographied (EA/Hept 2/1) to afford 33 mg of the desired compound.
LC-MS (B): $t_R$=1.00 min; [M+H]$^+$: 579.64.

26.2. 4-((S)-4-tert-butoxycarbonyl-2-{[4-(3-hydroxy-propyl)-6-phenyl-pyridine-2-carbonyl]-amino}-butyryl)-piperazine-1-carboxylic acid ethyl ester Raney Nickel in water was decanted, the supernatant was removed and MeOH was added. The process was repeated three times and the resulting Raney Nickel in MeOH was added to a solution of intermediate 26.1 (35 mg) in MeOH (3 ml). The mixture was stirred under hydrogen overnight, filtered through Celite and the solution evaporated off. The resulting compound (37 mg) was used in the next step without further purification.
LC-MS (B): $t_R$=0.98 min; [M+H]$^+$: 583.60.

26.3. 4-((S)-4-carboxy-2-{[4-(3-hydroxy-propyl)-6-phenyl-pyridine-2-carbonyl]-amino}-butyryl)-piperazine-1-carboxylic acid ethyl ester Intermediate 26.2 (37 mg) was dissolved in TFA/DCM (1/2, 0.9 ml), and it was stirred at RT for 1 h 30. The mixture was evaporated off and the residue taken up in THF/solution of LiOH in order to cleave off the trifluoroacetic ester. After 2 h, the desired compound was obtained. The mixture was acidified (1M HCl) and extracted twice with EA. The org. phases were dried and evaporated off and the crude was purified by preparative LC-MS (II) to afford 1.5 mg of the desired compound.
LC-MS (B): $t_R$=0.83 min; [M+H]$^+$: 527.61.

Example 27

4-((S)-4-carboxy-2-{[4-(3-hydroxy-3-methyl-but-1-ynyl)-6-phenyl-pyridine-2-carbonyl]-amino}-butyryl)-piperazine-1-carboxylic acid ethyl ester

27.1. 4-((S)-4-tert-butoxycarbonyl-2-{[4-(3-hydroxy-3-methyl-but-1-ynyl)-6-phenyl-pyridine-2-carbonyl]-amino}-butyryl)-piperazine-1-carboxylic acid ethyl ester This compound was prepared using a method analogous to that of Example 26, step 26.1, 2-methyl-3-butyn-2-ol replacing propargyl alcohol.
LC-MS (B): $t_R$=1.03 min; [M+H]$^+$: 607.69.

27.2. 4-((S)-4-carboxy-2-{[4-(3-hydroxy-3-methyl-but-1-ynyl)-6-phenyl-pyridine-2-carbonyl]-amino}-butyryl)-piperazine-1-carboxylic acid ethyl ester This compound was prepared using a method analogous to that of Example 1, step 1.8, intermediate 27.1 replacing intermediate 1.7. No CC was performed. The title compound was however purified by preparative LC-MS (III).
LC-MS (B): $t_R$=0.89 min; [M+H]$^+$: 551.62.

Example 28

4-((S)-4-carboxy-2-{[4-(3-hydroxy-3-methyl-butyl)-6-phenyl-pyridine-2-carbonyl]-amino}-butyryl)-piperazine-1-carboxylic acid ethyl ester

28.1. 4-((S)-4-tert-butoxycarbonyl-2-{[4-(3-hydroxy-3-methyl-butyl)-6-phenyl-pyridine-2-carbonyl]-amino}-butyryl)-piperazine-1-carboxylic acid ethyl ester This compound was prepared using a method analogous to that of Example 26, step 26.2, intermediate 27.1 replacing intermediate 26.1.
LC-MS (B): $t_R$=1.01 min; [M+H]$^+$: 611.75.

28.2. 4-((S)-4-carboxy-2-{[4-(3-hydroxy-3-methyl-butyl)-6-phenyl-pyridine-2-carbonyl]-amino}-butyryl)-piperazine-1-carboxylic acid ethyl ester This compound was prepared using a method analogous to that of Example 1, step 1.8, intermediate 28.1 replacing intermediate 1.7. No CC was performed, but the title compound was purified by preparative LC-MS (III).
LC-MS (B): $t_R$=0.87 min; [M+H]$^+$: 555.68.

Example 29

4-((S)-4-carboxy-2-{[4-(4-hydroxy-cyclohexyl)-6-phenyl-pyridine-2-carbonyl]-amino}-butyryl)-piperazine-1-carboxylic acid ethyl ester

29.1. Trifluoro-methanesulfonic acid 1,4-dioxa-spiro[4.5]dec-7-en-8-yl ester A lithium bis(trimethysilyl)amide solution (1M in THF, 13.7 ml) in THF (38 ml) was cooled down to −78° C. and 1,4-dioxaspiro[4,5]decan-8-one (2 g) in THF (14 ml) was added slowly. The mixture was stirred for 2 h 30 at −78° C. N-phenyl-bis(trifluoromethanesulfonimide) (4.76 g) in THF (15 ml) was added slowly. The temperature was then allowed to increase to 0° C. It was further stirred at 0° C. for 2 h. The solvent was evaporated off (water bath temperature: 25° C.) and HV dried. The crude was used without purification.
$^1$H-NMR (CDCl$_3$): 7.05 (m, 4H); 5.6 (s, 1H); 3.9 (s, 4H); 2.5 (s, 2H); 2.3 (s, 2H); 1.8 (m, 2H).

29.2. 8-(4,4,5,5-tetramethyl-[1,3,2]dioxaborolan-2-yl)-1,4-dioxa-spiro[4.5]dec-7-ene Intermediate 29.1 (3.58 g), bis(pinacolato)diboron (3.48 g), bis(triphenylphosphine)palladium(II) dichloride (262 mg), triphenylphosphine (195 mg) and K$_2$CO$_3$ (2.57 g) were dissolved in anhydrous dioxane (75 ml) under argon and refluxed overnight. After cooling down, a NaCl solution was added and the mixture was extracted with Hept. The org. layers were dried (Na$_2$SO$_4$) and evaporated off. The compound was used in the next step without purification or characterisation.

29.3. 4-((S)-4-tert-butoxycarbonyl-2-{[6-(1,4-dioxa-spiro[4.5]dec-7-en-8-yl)-2-phenyl-pyrimidine-4-carbonyl]-amino}-butyryl)-piperazine-1-carboxylic acid ethyl ester Intermediate 29.2 (2.16 mmol), intermediate 1.7 (0.36 mmol, 201 mg), tris-(dibenzylidenaceton)-dipalladium (0.011 mmol, 9.96 mg) and triphenylphosphine (0.076 mmol, 19.8 mg) were dissolved in toluene (0.432 ml), EtOH (0.108 ml) and a 1M Na$_2$CO$_3$ solution (0.108 ml). The mixture was refluxed for 48 h under argon. After cooling down, water was added and the mixture was extracted with chloroform. The org. layers were dried (Na$_2$SO$_4$) and evaporated off. CC (EA4Hept 1/1) afforded 238 mg of the desired compound.
LC-MS (B): $t_R$=1.07 min; [M+H]$^+$: 663.56.

29.4. 4-((S)-4-tert-butoxycarbonyl-2-{[6-(1,4-dioxa-spiro[4.5]dec-8-yl)-2-phenyl-pyrimidine-4-carbonyl]-amino}-butyryl)-piperazine-1-carboxylic acid ethyl ester Intermediate 29.3 (238 mg) was hydrogenated in EtOH (5 ml) with platinum dioxide (60 mg) for 48 h. The mixture was filtered through Celite and evaporated off. HV drying afforded 242 mg of the desired product.
LC-MS (B): $t_R$=1.10 min; [M+H]$^+$: 665.41.

29.5. 4-((S)-4-carboxy-2-{[6-(4-oxo-cyclohexyl)-2-phenyl-pyrimidine-4 carbonyl]-amino}-butyryl)-piperazine-1-carboxylic acid ethyl ester Intermediate 29.4 (239 mg) was dissolved in dioxane (3 ml) and the solution was cooled down to 5° C. A mixture of sulfuric acid (0.421 ml) and water (0.421 ml) cooled at 10° C. was added and the mixture was further stirred at RT for 1 h 30. Water was added and the mixture extracted with EA. The org. layers were dried (Na$_2$SO$_4$) and evaporated off. The crude residue was taken up in DCM/TFA (2/1, 3 ml). The mixture was stirred for 1 h 30 at RT and the solvents were removed under a stream of air. The residue was taken up in EA and washed with water. The org. layer was dried (Na$_2$SO$_4$) and evaporated off to afford the desired compound (203 mg).
LC-MS (B): $t_R$=1.13 min; [M+H]$^+$: 565.24.

29.6. 4-((S)-4-carboxy-2-{[4-(4-hydroxy-cyclohexyl)-6-phenyl-pyridine-2-carbonyl]-amino}-butyryl)-piperazine-1-carboxylic acid ethyl ester Intermediate 29.5 (203 mg) was dissolved in MeOH (3.6 ml) and NaBH$_4$ (14.2 mg) was added. The mixture was stirred at RT for 5 h. Water was added and the mixture was extracted with EA. The aq. phase was acidified with a 2M HCl solution (0.2 ml) and extracted again with EA. The org. layers were dried (Na$_2$SO$_4$) and evaporated off. Preparative TLC (EA4Hept, 5/1) followed by preparative LC-MS (II) afforded 6.2 mg of the desired compound.
LC-MS (B): $t_R$=0.85 min; [M+H]$^+$: 567.67.

Example 30

4-{(S)-4-carboxy-2-[(6-phenyl-4-phenylsulfanyl-pyridine-2-carbonyl)-amino]-butyryl}-piperazine-1-carboxylic acid ethyl ester

30.1. 4-{(S)-4-tert-butoxycarbonyl-2-[(6-phenyl-4-phenylsulfanyl-pyridine-2-carbonyl)-amino]-butyryl}-piperazine-1-carboxylic acid ethyl ester Thiophenol (44 ml) was added to a suspension of NaH (16 mg) in anhydrous DMF (0.16 ml) at 0° C. After 1 h stirring at 0° C., intermediate 1.7 (200 mg) was added. The mixture was allowed to warm to RT and was stirred at RT until completion. Water was added and the resulting mixture was extracted with DCM. The org. phases were dried (Na$_2$SO$_4$) and evaporated off. The crude was directly used in the next step.

LC-MS (B): t$_R$=1.14 min; [M+H]$^+$: 633.37.

30.2. 4-{(S)-4-carboxy-2-[(6-phenyl-4-phenylsulfanyl-pyridine-2-carbonyl)-amino]-butyryl}-piperazine-1-carboxylic acid ethyl ester This compound was prepared using a method analogous to that of Example 1, step 1.8, intermediate 30.1 replacing intermediate 1.7. No CC was performed, but the title compound was purified by preparative LC-MS (IV).

LC-MS (B): t$_R$=1.01 min; [M+H]$^+$: 577.42.

Example 31

4-((S)-4-carboxy-2-{[4-(2-hydroxy-cyclohexyl)-6-phenyl-pyridine-2-carbonyl]-amino}-butyryl)-piperazine-1-carboxylic acid ethyl ester

31.1. 4-{(S)-2-[(4-benzenesulfonyl-6-phenyl-pyridine-2-carbonyl)-amino]-4-tert-butoxycarbonyl-butyryl}-piperazine-1-carboxylic acid ethyl ester MCPBA (205 mg) was added to a 0° C. solution of intermediate 30.1 (240 mg) in DCM (12 ml). After 30 min stirring at 0° C., the mixture was allowed to warm to RT and was stirred at RT for 1 h 30. A K$_2$CO$_3$ solution was added and the org. phase was dried (Na$_2$SO$_4$) and evaporated off to afford 260 mg of the desired compound.

LC-MS (B): t$_R$=1.07 min; [M+H]$^+$: 665.42.

31.2. 4-((S)-4-carboxy-2-{[4-(2-oxo-cyclohexyl)-6-phenyl-pyridine-2-carbonyl]-amino}-butyryl)-piperazine-1-carboxylic acid ethyl ester Cyclohexanone (405 µl) was added to a suspension of NaH (62 mg) in THF (2.5 ml). After 15 min stirring at RT, intermediate 31.1 (260 mg) was added and the mixture was stirred at RT for 48 h. NaH (60 mg) and cyclohexanone (420 µl) were again added. After 2 h at RT, the mixture was extracted with Na$_2$CO$_3$ solution/DCM. The aq. layer was further washed with DCM. The combined DCM org. phases were washed with water and the combined aq. phases were acidified (1M HCl) and extracted with EA. The combined DCM and EA org. phases were dried (Na$_2$SO$_4$) and evaporated off to give 150 mg of the crude compound.

LC-MS (B): t$_R$=0.92 min; [M+H]$^+$: 565.45.

31.3. 4-((S)-4-carboxy-2-{[4-(2-hydroxy-cyclohexyl)-6-phenyl-pyridine-2-carbonyl]-amino}-butyryl)-piperazine-1-carboxylic acid ethyl ester Intermediate 31.2 (150 mg) was dissolved in MeOH (2 ml) and NaBH$_4$ (20 mg) was added at 0° C. After 2 h at 0° C., NaBH$_4$ (40 mg) was again added. After 18 h stirring at RT, water and DCM were added. The aq. phase was acidified (1M HCl) and extracted with DCM. The last org. phase was dried (Na$_2$SO$_4$) and evaporated off. Preparative LC-MS (III) afforded 5 mg of the desired product.

LC-MS (B): t$_R$=0.90 min; [M+H]$^+$: 567.49.

Example 32

4-{(S)-4-carboxy-2-[(6-phenyl-4-thiophen-3-yl-pyridine-2-carbonyl)-amino]-butyryl}-piperazine-1-carboxylic acid ethyl ester

32.1. 4-{(S)-4-tert-butoxycarbonyl-2-[(6-phenyl-4-thiophen-3-yl-pyridine-2-carbonyl)-amino]-butyryl}-piperazine-1-carboxylic acid ethyl ester Intermediate 1.7 (100 mg), 3-thiopheneboronic acid (27 mg) and tetrakis(triphenylphosphine)palladium (12.4 mg) were dissolved in anhydrous DME (1 ml) and a 2M K$_2$CO$_3$ solution (0.179 ml) and the mixture was degassed with argon. The mixture was heated at 80° C. overnight, filtered through Celite and evaporated off. Preparative TLC (EA/Hept 1/1) offered 29 mg of the desired compound.

LC-MS (B): t$_R$=1.10 min; [M+H]$^+$: 607.49.

32.2. 4-{(S)-4-carboxy-2-[(6-phenyl-4-thiophen-3-yl-pyridine-2-carbonyl)-amino]-butyryl}-piperazine-1-carboxylic acid ethyl ester This compound was prepared using a method analogous to that of Example 1, step 1.8, intermediate 32.1 replacing intermediate 1.7. No CC was performed, but the title compound was purified by preparative LC-MS (IV).

LC-MS (B): t$_R$=0.97 min; [M+H]$^+$: 551.42.

Example 33

4-{(S)-4-carboxy-2-[(4-furan-3-yl-6-phenyl-pyridine-2-carbonyl)-amino]-butyryl}-piperazine-1-carboxylic acid ethyl ester

33.1. 4-{(S)-4-tert-butoxycarbonyl-2-[(4-furan-3-yl-6-phenyl-pyridine-2-carbonyl)-amino]-butyryl}-piperazine-1-carboxylic acid ethyl ester This compound was prepared using a method analogous to that of Example 32, step 32.2, 3-furanboronic acid replacing 3-thiopheneboronic acid.

LC-MS (B): t$_R$=1.09 min; [M+H]$^+$: 591.58.

33.2. 4-{(S)-4-carboxy-2-[(4-furan-3-yl-6-phenyl-pyridine-2-carbonyl)-amino]-butyryl}-piperazine-1-carboxylic acid ethyl ester This compound was prepared using a method analogous to that of Example 1, step 1.8, intermediate 33.1 replacing intermediate 1.7. No CC was performed. The title compound was however purified by preparative LC-MS (III).

LC-MS (B): t$_R$=0.95 min; [M+H]$^+$: 535.45.

Example 34

4-{(S)-4-carboxy-2-[(4-isopropylsulfanyl-6-phenyl-pyridine-2-carbonyl)-amino]-butyryl}-piperazine-1-carboxylic acid ethyl ester

34.1. 4-{(S)-4-tert-butoxycarbonyl-2-[(4-isopropylsulfanyl-6-phenyl-pyridine-2-carbonyl)-amino]-butyryl}-piperazine-1-carboxylic acid ethyl ester This compound was prepared using a method analogous to that of Example 30, step 30.1, 2-propanethiol replacing thiophenol.

LC-MS (B): t$_R$=1.12 min; [M+H]$^+$: 599.54.

34.2. 4-{(S)-4-carboxy-2-[(4-isopropylsulfanyl-6-phenyl-pyridine-2-carbonyl)-amino]-butyryl}-piperazine-1-carboxylic acid ethyl ester This compound was prepared using a method analogous to that of Example 1, step 1.8, intermediate 34.1 replacing intermediate 1.7. No CC was performed, but the title compound was purified by preparative LC-MS (IV).
LC-MS (B): $t_R$=0.98 min; $[M+H]^+$: 543.43.

Example 35

4-((S)-3-(4-carboxy-phenyl)-2-{[4-(2-methoxymethyl-cyclopropyl)-6-phenyl-pyridine-2-carbonyl]-amino}-propionyl)-piperazine-1-carboxylic acid ethyl ester

35.1. [(S)-2-benzyloxycarbonylamino-3-(4-tert-butoxycarbonyl-phenyl)-propionyl]piperazine-1-carboxylic acid ethyl ester To a solution of Z-p-carboxy-(L)-Phe(OtBu)-OH (5 g) in DCM (100 ml) were added at RT HOBT (2.11 g), EDCI (2.5 g) and DIPEA (4.4 ml). After 15 min stirring at RT, 1-ethoxycarbonylpiperazine (2 g) was added and the stirring was continued at RT overnight. 150 ml of EA and 60 ml of a NaHCO$_3$ solution were added to the reaction mixture and the phases were separated. The org. phase was washed with an aq. NaHSO$_4$ (1M) solution and with brine, dried over Na$_2$SO$_4$ and evaporated off. After HV drying, 6 g of the desired compound were obtained.
LC-MS (B): $t_R$=1.03 min; $[M+H]^+$: 540.58.

35.2. 4-[(S)-2-amino-3-(4-tert-butoxycarbonyl-phenyl)-propionyl]-piperazine-1-carboxylic acid ethyl ester This compound was prepared using a method analogous to that of Example 1, step 1.6, intermediate 35.1 replacing intermediate 1.5.
LC-MS (B): $t_R$=0.75 min; $[M+H]^+$: 406.53.

35.3. 4-[(S)-2-[(4-chloro-6-phenyl-pyridine-2-carbonyl)-amino]-3-(4-ethoxycarbonyl-phenyl)-propionyl]-piperazine-1-carboxylic acid tert-butyl ester This compound was prepared using a method analogous to that of Example 1, step 1.7, intermediate 35.2 replacing intermediate 1.6.
LC-MS (B): $t_R$=1.13 min; $[M+H]^+$: 621.47.

35.4. 4-((S)-3-(4-tert-butoxycarbonyl-phenyl)-2-{[4-(2-methoxymethyl-cyclopropyl)-6-phenyl-pyridine-2-carbonyl]-amino}-propionyl)-piperazine-1-carboxylic acid ethyl ester This compound was prepared using a method analogous to that of Example 20, step 20.4, intermediate 35.3 replacing intermediate 1.7. The compound was however purified by CC (EE/Hept 3/7).
LC-MS (B): $t_R$=1.12 min; $[M+H]^+$: 671.58.

35.5. 4-((S)-3-(4-carboxy-phenyl)-2-{[4-(2-ethoxyethyl-cyclopropyl)-6-phenyl-pyridine-2-carbonyl]-amino}-propionyl)-piperazine-1-carboxylic acid ethyl ester This compound was prepared using a method analogous to that of Example 1, step 1.8, intermediate 35.4 replacing intermediate 1.7. The compound was however purified by preparative TLC (DCM/MeOH/AcOH 100/5/1).
LC-MS (B): $t_R$=0.96 min; $[M+H]^+$: 615.45.

Example 36

4-{(S)-4-carboxy-2-[(4-methyl-6-phenyl-pyridine-2-carbonyl)-amino]-butyryl}-piperazine-1-carboxylic acid ethyl ester This compound was prepared using a method analogous to that of Example 7, step 7.1, 8, intermediate 1.8 replacing intermediate 1.7 and methylboronic acid replacing 4-methoxyphenylboronic acid. The compound was purified by preparative LC-MS (V).
LC-MS (B): $t_R$=0.90 min; $[M+H]^+$: 483.46.

Example 37

4-((S)-4-carboxy-2-{[6-phenyl-4-(tetrahydro-furan-3-yloxy)-pyridine-2-carbonyl]-amino}-butyryl)-piperazine-1-carboxylic acid ethyl ester To a solution of 3-hydroxytetrahydrofurane (314 mg) in DMF (6 ml) were added, at RT, NaH (156 mg, 55% in oil), and, after 15 min stirring at RT, intermediate 1.7 (400 mg). The stirring was continued at 70° C. overnight. Sat. aq. NH$_4$Cl was added and the mixture was extracted with Et$_2$O. The aq. phase was acidified with an aq. HCl (1M) solution and extracted again with Et$_2$O and DCM. The org. phases were combined, dried over Na$_2$SO$_4$ and evaporated off. After purification by CC (EA/AcOH 100/1), followed by preparative LC-MS (III, then II), 21 mg of the desired product were obtained.
LC-MS (B): $t_R$=0.89 min; $[M+H]^+$: 555.49.

Example 38

4-{(S)-4-carboxy-2-[(6-phenyl-pyridine-2-carbonyl)-amino]-butyryl}-piperazine-1-carboxylic acid ethyl ester

38.1. 2-phenyl-pyridine 1-oxide 3-chloroperbenzoic acid (19 g) was added portionwise to an ice-cold solution of 2-phenylpyridine (10 g) in DCM (30 ml). The mixture was allowed to warm to RT and was stirred at RT for 4 h. 100 ml of a NaHCO$_3$ solution were added to the reaction mixture and the phases were separated. The aq. phase was further extracted with DCM and the combined org. phases were washed with an aq. NaHSO$_3$ (40%) solution and evaporated off. Recrystallisation (EA) afforded 8.77 g of the desired compound.
LC-MS (B): $t_R$=0.65 min; $[M+H]^+$: 172.10.

38.2. 6-phenyl-pyridine-2-carbonitrile

Trimethylsilylcyanide (8 ml) was added to a solution of intermediate 38.1 (8.16 g) in DCM (95 ml). A solution of benzoyl chloride (7 ml) in DCM (50 ml) was added dropwise to the previous mixture. The reaction was stirred for 24 h at RT. Diisopropylamine (10.2 ml) was added and the reaction was stirred for 3 h. A Na$_2$CO$_3$ solution was added to the reaction mixture. The layers were separated and the aq. phase was extracted with DCM. The org. phases were combined, dried over Na$_2$SO$_4$ and evaporated off. The compound was purified by CC (EA/Hept 1/3) to afford 8.13 g of the desired product.

LC-MS (B): $t_R$=0.94 min; [M+H+MeCN]$^+$: 222.34.

38.3. 6-phenyl-pyridine-2-carboxylic acid

Intermediate 38.2 (8.12 g) was dissolved in EtOH (30 ml), water (30 ml) and a 32% aq. NaOH solution. The mixture was heated at 110° C. for 2 h 30. Ethanol was evaporated off, water (60 ml) was added to the remaining mixture, followed by a 10% aq. HCl solution (60 ml, until pH 1). The suspension was filtered off, the powder was washed with water and dried to afford 8.11 g of the desired compound. No further purification was carried out.

LC-MS (B): $t_R$=0.78 min; [M+H]$^+$: 200.02.

38.4. 4-{(S)-4-tert-butoxycarbonyl-2-[(6-phenyl-pyridine-2-carbonyl)-amino]-butyryl}-piperazine-1-carboxylic acid ethyl ester This compound was prepared using a method analogous to that of Example 1, step 1.5, intermediate 1.6 replacing 1-ethoxycarbonylpiperazine, intermediate 38.3 replacing Z-(L)Glu(OtBu)-OH and DCM being used instead of DCM/THF.

LC-MS (B): $t_R$=1.03 min; [M+H]$^+$: 525.50.

38.5. 4-{(S)-4-carboxy-2-[(6-phenyl-pyridine-2-carbonyl)-amino]-butyryl}-piperazine-1-carboxylic acid ethyl ester This compound was prepared using a method analogous to that of Example 1, step 1.8, intermediate 38.4 replacing intermediate 1.7. No CC was performed but the compound was purified by preparative LC-MS (V).

LC-MS (B): $t_R$=0.85 min; [M+H]$^+$: 469.38.

The compounds of Examples 39 to 65 were prepared using a method analogous to that of the Example indicated between brackets, except that the last step of the corresponding Example was not carried out.

Example 39

4-{(S)-4-O-tert-butoxycarbonyl-2-[(4-chloro-6-phenyl-pyridine-2-carbonyl)-amino]-butyryl}-piperazine-1-carboxylic acid ethyl ester (Example 1). LC-MS (B): $t_R$=1.07 min; [M+H]$^+$: 559.3.

Example 40

4-{(S)-4-tert-butoxycarbonyl-2-[(4-cyclopentyloxy-6-phenyl-pyridine-2-carbonyl)-amino]-butyryl}-piperazine-1-carboxylic acid ethyl ester (Example 3). LC-MS (B): $t_R$=1.14 min; [M+H]$^+$: 609.4.

Example 41

4-((S)-4-tert-butoxycarbonyl-2-{[4-(1-hydroxy-1-methyl-ethyl)-6-phenyl-pyridine-2-carbonyl]-amino}-butyryl)-piperazine-1-carboxylic acid ethyl ester (Example 4). LC-MS (B): $t_R$=0.99 min; [M+H]$^+$: 583.52.

Example 42

4-{(S)-4-tert-butoxycarbonyl-2-[(4,6-diphenyl-pyridine-2-carbonyl)-amino]-butyryl}-piperazine-1-carboxylic acid ethyl ester (Example 5). LC-MS (B): $t_R$=1.10 min; [M+H]$^+$: 601.3.

Example 43

4-{(S)-4-tert-butoxycarbonyl-2-[(6-phenyl-4-pyrazol-1-yl-pyridine-2-carbonyl)-amino]-butyryl}-piperazine-1-carboxylic acid ethyl ester (Example 6). LC-MS (B): $t_R$=1.06 min; [M+H]$^+$: 591.5.

Example 44

4-((S)-4-tert-butoxycarbonyl-2-{[4-(4-methoxy-phenyl)-6-phenyl-pyridine-2-carbonyl]-amino}-butyryl)-piperazine-1-carboxylic acid ethyl ester (Example 7). LC-MS (B): $t_R$=1.10 min; [M+H]$^+$: 631.6.

Example 45

4-((S)-4-tert-butoxycarbonyl-2-{[4-cyclopropyl-6-phenyl-pyridine-2-carbonyl]-amino}-butyryl)-piperazine-1-carboxylic acid ethyl ester (Example 8). LC-MS (B): $t_R$=1.07 min; [M+H]$^+$: 565.5.

Example 46

4-{(S)-4-tert-butoxycarbonyl-2-[(4-butyl-6-phenyl-pyridine-2-carbonyl)-amino]-butyryl}-piperazine-1-carboxylic acid ethyl ester (Example 9). LC-MS (B): $t_R$=1.13 min; [M+H]$^+$: 581.5.

Example 47

4-{(S)-4-O-tert-butoxycarbonyl-2-[(4-[(R)-3-hydroxy-pyrrolidin-1-yl]-6-phenyl-pyridine-2-carbonyl)-amino]-butyryl}-piperazine-1-carboxylic acid ethyl ester (Example 14). LC-MS (B): $t_R$=0.81 min; [M+H]$^+$: 609.7.

Example 48

4-{(S)-4-tert-butoxycarbonyl-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester (Example 15). LC-MS (B): $t_R$=0.83 min; [M+H]$^+$: 624.5.

Example 49

4-{(S)-4-tert-butoxycarbonyl-2-[(6-phenyl-4-pyrrolidin-1-yl-pyridine-2-carbonyl)-amino]-butyryl}-piperazine-1-carboxylic acid ethyl ester (Example 16). LC-MS (B): $t_R$=0.89 min; [M+H]$^+$: 594.5.

Example 50

4-((S)-4-tert-butoxycarbonyl-2-{[4-(2-hydroxy-ethylamino)-6-phenyl-pyridine-2-carbonyl]-amino}-butyryl)-piperazine-1-carboxylic acid ethyl ester (Example 17). LC-MS (B): $t_R$=0.89 min; $[M+H]^+$: 584.5.

Example 51

4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid ethyl ester (Example 18). LC-MS (B): $t_R$=0.88 min; $[M+H]^+$: 624.6.

Example 52

4-{(S)-4-tert-butoxycarbonyl-2-[(4-isopropylamino-6-phenyl-pyridine-2-carbonyl)-amino]-butyryl}-piperazine-1-carboxylic acid ethyl ester (Example 19). LC-MS (B): $t_R$=0.87 min; $[M+H]^+$: 582.5.

Example 53

4-((S)-4-tert-butoxycarbonyl-2-{[4-(2-methoxymethyl-cyclopropyl)-6-phenyl-pyridine-2-carbonyl]-amino}-butyryl)-piperazine-1-carboxylic acid ethyl ester (Example 20). LC-MS (B): $t_R$=1.06 min; $[M+H]^+$: 609.6.

Example 54

4-((S)-4-tert-butoxycarbonyl-2-{[4-(2-hydroxymethyl-cyclopropyl)-6-phenyl-pyridine-2-carbonyl]-amino}-butyryl)-piperazine-1-carboxylic acid ethyl ester (Example 21). LC-MS (B): $t_R$=1.01 min; $[M+H]^+$: 595.3.

Example 55

4-{(S)-4-tert-butoxycarbonyl-2-[(4,6-diphenyl-pyridine-2-carbonyl)-amino]-butyryl}-3-methyl-piperazine-1-carboxylic acid ethyl ester (Example 23). LC-MS (B): $t_R$=1.12 min; $[M+H]^+$: 615.5.

Example 56

4-{(S)-4-tert-butoxycarbonyl-2-[(4-phenyl-6-pyrazol-1-yl-pyridine-2-carbonyl)-amino]-butyryl}-piperazine-1-carboxylic acid ethyl ester (Example 25). LC-MS (B): $t_R$=1.08 min; $[M+H]^+$: 591.3.

Example 57

4-((S)-4-tert-butoxycarbonyl-2-{[4-(3-hydroxy-propyl)-6-phenyl-pyridine-2-carbonyl]-amino}-butyryl)-piperazine-1-carboxylic acid ethyl ester (Example 26). LC-MS (B): $t_R$=0.98 min; $[M+H]^+$: 583.60.

Example 58

4-((S)-4-tert-butoxycarbonyl-2-{[4-(3-hydroxy-3-methyl-but-1-ynyl)-6-phenyl-pyridine-2-carbonyl]-amino}-butyryl)-piperazine-1-carboxylic acid ethyl ester (Example 27). LC-MS (B): $t_R$=1.03 min; $[M+H]^+$: 607.69.

Example 59

4-((S)-4-tert-butoxycarbonyl-2-{[4-(3-hydroxy-3-methyl-butyl)-6-phenyl-pyridine-2-carbonyl]-amino}-butyryl)-piperazine-1-carboxylic acid ethyl ester (Example 28). LC-MS (B): $t_R$=1.01 min; $[M+H]^+$: 611.75.

Example 60

4-{(S)-4-tert-butoxycarbonyl-2-[(6-phenyl-4-phenylsulfanyl-pyridine-2-carbonyl)-amino]-butyryl}-piperazine-1-carboxylic acid ethyl ester (Example 30). LC-MS (B): $t_R$=1.14 min; $[M+H]^+$: 633.37.

Example 61

4-{(S)-4-tert-butoxycarbonyl-2-[(6-phenyl-4-thiophen-3-yl-pyridine-2-carbonyl)-amino]-butyryl}-piperazine-1-carboxylic acid ethyl ester (Example 32). LC-MS (B): $t_R$=1.10 min; $[M+H]^+$: 607.49.

Example 62

4-{(S)-4-tert-butoxycarbonyl-2-[(4-furan-3-yl-6-phenyl-pyridine-2-carbonyl)-amino]-butyryl}-piperazine-1-carboxylic acid ethyl ester (Example 33). LC-MS (B): $t_R$=1.09 min; $[M+H]^+$: 591.58.

Example 63

4-{(S)-4-tert-butoxycarbonyl-2-[(4-isopropylsulfanyl-6-phenyl-pyridine-2-carbonyl)-amino]-butyryl}-piperazine-1-carboxylic acid ethyl ester (Example 34). LC-MS (B): $t_R$=1.12 min; $[M+H]^+$: 599.54.

Example 64

4-((S)-3-(4-tert-butoxycarbonyl-phenyl)-2-{[4-(2-methoxymethyl-cyclopropyl)-6-phenyl-pyridine-2-carbonyl]-amino}-propionyl)-piperazine-1-carboxylic acid ethyl ester (Example 35). LC-MS (B): $t_R$=1.12 min; $[M+H]^+$: 671.58.

Example 65

4-{(S)-4-tert-butoxycarbonyl-2-[(6-phenyl-pyridine-2-carbonyl)-amino]-butyryl}-piperazine-1-carboxylic acid ethyl ester (Example 38). LC-MS (B): $t_R$=1.03 min; $[M+H]^+$: 525.50.

Example 66

4-[(S)-2-[(4,6-diphenyl-pyridine-2-carbonyl)-amino]-3-(2H-tetrazol-5-yl)-propionyl]-piperazine-1-carboxylic acid ethyl ester To a microwave vial was added intermediate 22.3 (50 mg), sodium azide (7 mg), zinc dibromide (22 mg). Water (0.4 ml) was added and the mixture was heated under microwave irradiation at 100° C. for 1 h. A 2M HCl solution was added until pH 1, followed by EA. The aq. layer was extracted with EA, the combined org. phases were dried (Na$_2$SO$_4$) and evaporated off. The compound was purified by CC (DCM to DCM/MeOH 8/2) to afford 20 mg of the desired product.

LC-MS (B): $t_R$=0.96 min; [M+H]$^+$: 555.39.

Example 67

4-((S)-4-carboxy-2-{[4-((S)-3-methoxy-pyrrolidin-1-yl)-6-phenyl-pyridine-2-carbonyl]-amino}-butyryl)-piperazine-1-carboxylic acid butyl ester

67.1. 4-benzyl-piperazine-1-carboxylic acid butyl ester

To a solution of 1-benzyl-piperazine (1.97 ml) and NEt$_3$ (1.9 ml) in DCM (100 ml) was added n-butyl chloroformate (1.47 ml). The mixture was stirred at RT for 2 h. Water was added, the org. phase separated, dried (Na$_2$SO$_4$) and evaporated off to give 3.13 g of a yellow oil.

LC-MS (B): $t_R$=0.73 min; [M+H]$^+$: 277.42.

67.2. Piperazine-1-carboxylic acid butyl ester

This compound was prepared using a method analogous to that of Example 1, step 1.6, intermediate 67.1 replacing intermediate 1.5.

LC-MS (B): $t_R$=0.54 min; [M+H+MeCN]$^+$: 226.39.

67.3. 4-((S)-2-benzyloxycarbonylamino-4-tert-butoxycarbonyl-butyryl)-piperazine-1-carboxylic acid butyl ester This compound was prepared using a method analogous to that of Example 1, step 1.5, intermediate 67.2 replacing 1-ethoxycarbonylpiperazine and using DCM instead of DCM/THF.

LC-MS (B): $t_R$=1.04 min; [M+H]$^+$: 506.49.

67.4. 4-((S)-2-amino-4-tert-butoxycarbonyl-butyryl)-piperazine-1-carboxylic acid butyl ester acetic acid salt This compound was prepared using a method analogous to that of Example 1, step 1.6, intermediate 67.3 replacing intermediate 1.5 and using EtOH/AcOH (100/1) instead of EtOH.

LC-MS (B): $t_R$=0.75 min; [M+H]$^+$: 372.49.

67.5. (S)-3-hydroxypyrrolidine-1-carboxylic acid tert-butyl ester

Di-tert-butyl-dicarbonate (27.5 g) was added portionwise to a solution of (S)-3-hydroxypyrrolidine (10 g) and NEt$_3$ (32 ml) in DCM (240 ml). The reaction mixture was stirred overnight at RT. Water was added and the org. phase was separated. It was washed with sat. aq. NH$_4$Cl, sat. aq. NaHCO$_3$ and sat. aq. NaCl. The org. phase was dried (Na$_2$SO$_4$) and evaporated off to afford 21.4 g of the desired compound.

$^1$H-NMR (CDCl$_3$): 4.43 (br. s, 1H); 3.40 (m, 4H); 2.70 (m, 1H); 1.93 (m, 2H); 1.46 (s, 9H).

67.6. (S)-3-methoxy-pyrrolidine-1-carboxylic acid tert-butyl ester

To an ice-cold solution of intermediate 67.5 (22 g) in THF (300 ml) was added NaH (7.7 g, 55% in mineral oil) portionwise. The reaction mixture was stirred for 30 min at RT, cooled down to 0° C. and MeI (11 ml) was added dropwise. Stirring was continued for additional 2 h at RT. Water and ethanolamine (14 ml) were added to the reaction mixture that was stirred for 15 min. The org. phase was separated and the aq. phase was extracted with DCM three times. The combined org. phases were washed with sat. aq. NaCl, dried (Na$_2$SO$_4$) and evaporated off to afford 27.5 g of a yellow oil.

$^1$H-NMR (CDCl$_3$): 3.94 (br. s, 1H); 3.44 (m, 4H); 3.35 (s, 3H); 1.99 (m, 2H); 1.48 (s, 9H).

67.7. (S)-methoxy-pyrrolidine hydrochloride salt

Intermediate 67.6 (27.5 g) was dissolved in 1M HCl in EA (300 ml) and 3M HCl in EA (50 ml) was added. The reaction mixture was stirred overnight at RT and the solvent was evaporated off. The residue was taken up in Et$_2$O (500 ml) and the compound precipitated out. The suspension was stirred for 1 h, filtered off and the powder washed with Et$_2$O. HV drying afforded 13.9 g of the desired hydrochloride salt.

$^1$H-NMR (CDCl$_3$): 9.84 (br. s, 1H); 4.10 (br s, 1H); 3.43 (m, 4H); 3.33 (s, 3H); 2.19 (m, 1H); 2.04 (m, 1H).

67.8. 4-((S)-3-methoxy-pyrrolidin-1-yl)-6-phenyl-pyridine-2-carboxylic acid Intermediate 1.4 (sodium salt, 1.5 g) and intermediate 67.7 (963 mg) were dissolved in THF (2 ml) and DIPEA (2.2 ml) was added. The reaction mixture was heated in a microwave oven at 110° C. for 10 h and at 140° C. for further 6 h. Water was added and the mixture was extracted with EA. The aq. phase was acidified to pH 5 with 1M HCl and extracted with DCM. The combined org. phases were dried (Na$_2$SO$_4$) and evaporated off. The residue was purified by CC (EA/MeOH 4/1 to 3/2) to afford 1.06 g of the desired compound.

LC-MS (B): $t_R$=0.70 min; [M+H]$^+$: 299.08.

67.9. 4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid butyl ester This compound was prepared using a method analogous to that of Example 1, step 1.7, intermediate 67.4 replacing intermediate 1.6 and intermediate 67.8 replacing intermediate 1.4. The compound was however purified by CC (EA).

LC-MS (B): $t_R$=0.99 min; [M+H]$^+$: 652.32.

67.10. 4-((S)-4-carboxy-2-{[4-((S)-3-methoxy-pyrrolidin-1-yl)-6-phenyl-pyridine-2-carbonyl]-amino}-butyryl)-piperazine-1-carboxylic acid butyl ester This compound was prepared using a method analogous to that of Example 1, step 1.8, intermediate 67.9 replacing intermediate 1.7. The compound was however purified by CC (EA/MeOH 9/1).

LC-MS (B): $t_R$=0.86 min; [M+H]$^+$: 596.30.

Example 68

4-((S)-3-hydroxy-2-{[4-((S)-3-methoxy-pyrrolidin-1-yl)-6-phenyl-pyridine-2-carbonyl]-amino}-propionyl)-piperazine-1-carboxylic acid butyl ester

68.1. 4-((S)-2-tert-butoxycarbonylamino-3-hydroxy-propionyl)-piperazine-1-carboxylic acid butyl ester This compound was prepared using a method analogous to that of Example 1, step 1.5, intermediate 67.2 replacing 1-ethoxycarbonylpiperazine, N-(tert-butoxycarbonyl)-L-serine replacing Z-(L)Glu(OtBu)-OH and using DCM instead of DCM/THF. The compound was however purified by CC (EA/Hept 7/3).
LC-MS (B): $t_R$=0.83 min; [M+H]$^+$: 374.17.

68.2. 4-((S)-2-amino-3-hydroxy-propionyl)-piperazine-1-carboxylic acid butyl ester trifluoroacetate salt This compound was prepared using a method analogous to that of Example 1, step 1.8, intermediate 68.1 replacing intermediate 1.7. The compound was however taken up in toluene and the solvent was evaporated off to remove residual TFA.
LC-MS (B): $t_R$=0.59 min; [M+H]$^+$: 274.10.

68.3. 4-((S)-3-hydroxy-2-{[4-((S)-3-methoxy-pyrrolidin-1-yl)-6-phenyl-pyridine-2-carbonyl]-amino}-propionyl)-piperazine-1-carboxylic acid butyl ester This compound was prepared using a method analogous to that of Example 1, step 1.5, intermediate 68.2 replacing 1-ethoxycarbonylpiperazine, intermediate 67.8 replacing Z-(L)Glu(OtBu)-OH and using DCM instead of DCM/THF. The compound was however purified by CC (EA/NEt$_3$ 9.9/0.1 to EA/MeOH/NEt$_3$ 9.6/0.3/0.1).
LC-MS (B): $t_R$=0.84 min; [M+H]$^+$: 554.35.

Example 69

4-((S)-2-{[4-((S)-3-methoxy-pyrrolidin-1-yl)-6-phenyl-pyridine-2-carbonyl]-amino}-3-methyl-butyryl)-piperazine-1-carboxylic acid butyl ester

69.1. 4-(2-tert-butoxycarbonylamino-3-methyl-butyryl)-piperazine-1-carboxylic acid butyl ester This compound was prepared using a method analogous to that of Example 1, step 1.5, intermediate 67.2 replacing 1-ethoxycarbonylpiperazine and Boc-L-valine replacing Z-(L)Glu(OtBu)-OH.
LC-MS (B): $t_R$=1.01 min; [M+H]$^+$: 386.49.

69.2. 4-((S)-2-amino-3-methyl-butyryl)-piperazine-1-carboxylic acid butyl ester This compound was prepared using a method analogous to that of Example 1, step 1.8, intermediate 69.1 replacing intermediate 1.7. The compound was however worked up as follows: the pH was brought to 13 by the slow addition of 1M NaOH at 0° C. and the mixture was extracted with DCM. The org. phases were washed with sat. aq. NaCl, water, dried (Na$_2$SO$_4$) and evaporated off to afford the desired product.
LC-MS (B): $t_R$=0.72 min; [M+H]$^+$: 286.48.

69.3. 4-((S)-2-{[4-((S)-3-methoxy-pyrrolidin-1-yl)-6-phenyl-pyridine-2 carbonyl]-amino}-3-methyl-butyryl)-piperazine-1-carboxylic acid butyl ester This compound was prepared using a method analogous to that of Example 1, step 1.7, intermediate 69.2 replacing intermediate 1.6 and intermediate 67.8 replacing intermediate 1.4. The compound was however purified by CC (EA).
LC-MS (B): $t_R$=0.95 min; [M+H]$^+$: 566.43.

Example 70

4-((S)-4-carboxy-2-{[5-fluoro-4-((S)-3-methoxy-pyrrolidin-1-yl)-6-phenyl-pyridine-2-carbonyl]-amino}-butyryl)-piperazine-1-carboxylic acid butyl ester

70.1. 3-fluoro-4-(3-methoxy-pyrrolidin-1-yl)-pyridine

To a solution of 4-chloro-3-fluoropyridine (500 mg) in MeCN (1 ml) was added intermediate 67.7 (560 mg) and DIPEA (1.45 ml). The mixture was heated in a microwave oven at 130° C. for 30 min and at 100° C. for 2 days. The mixture was evaporated off and the residue was purified by CC (EA/Hept 0/1 to EA/Hept 1/0) to afford 265 mg of the desired compound.
$^1$H-NMR (CDCl$_3$): 8.14 (d, 1H); 8.05 (d, 1H); 6.45 (dd, 1H); 4.08 (m, 1H); 3.70 (m, 1H); 3.60 (m, 3H); 3.39 (s, 3H); 2.19 (m, 1H); 2.05 (m, 1H).

70.2. 3-fluoro-4-(3-methoxy-pyrrolidin-1-yl)-pyridine 1-oxide

MCPBA (280 mg) was added to a solution of intermediate 70.1 (265 mg) in chloroform (3 ml) at RT. The reaction mixture was stirred at RT overnight, then heated to 40-45° C. overnight. An aq. sodium bisulfite solution was added and the mixture was extracted with DCM and EA. The combined org. phases were dried (Na$_2$SO$_4$), evaporated off and the residue was purified by CC (DCM/MeOH 9/1 to MeOH) to afford 280 mg of the desired product.
LC-MS (B): $t_R$=0.59 min; [M+H]$^+$: 213.45.

70.3. 3-fluoro-4-(3-methoxy-pyrrolidin-1-yl)-2-phenyl-pyridine 1-oxide

A solution of bromobenzene (0.495 ml) in toluene (3 ml) was added under argon to K$_2$CO$_3$ (466 mg), palladium diacetate (62 mg), tri-tert-butylphosphonium tetrafluoroborate (52 mg) and intermediate 70.2 (250 mg). The reaction mixture was stirred at 110° C. overnight and filtered off through Celite. The resulting solution was evaporated off and the residue was purified by CC (Hept/EA 7/3) to afford 280 mg of the desired product.
LC-MS (B): $t_R$=0.77 min; [M+H]$^+$: 289.41.

70.4. 5-fluoro-4-(3-methoxy-pyrrolidin-1-yl)-6-phenyl-pyridine-2-carbonitrile This compound was prepared using a method analogous to that of Example 2, step 2.1, intermediate 70.3 replacing 4-phenylpyridine N-oxide. The reaction was however stirred at RT overnight and refluxed for 4 h.
LC-MS (B): $t_R$=1.06 min; [M+H]$^+$: 298.43.

70.5. 5-fluoro-4-(3-methoxy-pyrrolidin-1-yl)-6-phenyl-pyridine-2-carboxylic acid Intermediate 70.4 (170 mg) in conc. HCl (1 ml) was stirred at RT overnight and heated to reflux for 150 min. The reaction mixture was cooled down and quenched with an aq. $Na_2CO_3$ solution until pH 5. The mixture was extracted with EA and the combined org. layers were dried ($MgSO_4$) and evaporated off. The residue was purified by CC (Hept/EA 1/0 to 0/1) to give 20 mg of the desired compound.

LC-MS (B): $t_R$=0.70 min; $[M+H]^+$: 317.08.

70.6. 4-((S)-4-tert-butoxycarbonyl-2-{[5-fluoro-4-(3-methoxy-pyrrolidin-1-yl)-6-phenyl-pyridine-2-carbonyl]-amino}-butyryl)-piperazine-1-carboxylic acid butyl ester This compound was prepared using a method analogous to that of Example 1, step 1.7, intermediate 67.4 replacing intermediate 1.6 and intermediate 70.5 replacing intermediate 1.4. The compound was however purified by CC (EA/Hept 0/1 to EA/Hept 1/0).

LC-MS (B): $t_R$=1.16 min; $[M+H]^+$: 670.11.

70.7. 4-((S)-4-carboxy-2-{[5-fluoro-4-((S)-3-methoxy-pyrrolidin-1-yl)-6-phenyl-pyridine-2-carbonyl]-amino}-butyryl)-piperazine-1-carboxylic acid butyl ester This compound was prepared using a method analogous to that of Example 1, step 1.8, intermediate 70.6 replacing intermediate 1.7. The compound was however purified by CC (DCM/MeOH 1/0 to DCM/MeOH 9/1).

LC-MS (B): $t_R$=1.01 min; $[M+H]^+$: 613.98.

Example 71

4-{(S)-4-carboxy-2-[(4-cyclopropyl-3-methoxy-6-phenyl-pyridine-2-carbonyl)-amino]-butyryl}-piperazine-1-carboxylic acid ethyl ester

71.1. 4,6-dichloro-3-methoxy-2-methyl-pyridine

This compound was prepared using a method analogous to that of Example 1, step 1.3, 4-chloro-3-methoxy-2-methylpyridine N-oxide replacing intermediate 1.2.

LC-MS (B): $t_R$=0.89 min; $[M+H]^+$: 233.03.

71.2. 4-chloro-3-methoxy-2-methyl-6-phenyl-pyridine

This compound was prepared using a method analogous to that of Example 5, step 5.1, intermediate 71.1 replacing intermediate 1.3, no EtOH being used and no work-up being performed.

LC-MS (B): $t_R$=0.95 min; $[M+H]^+$: 234.10.

71.3. 4-chloro-3-methoxy-2-methyl-6-phenyl-pyridine 1-oxide

MCPBA (1.1 g) was added to a solution of intermediate 71.2 (1 g) in DCM (20 ml) at RT. The reaction mixture was heated at reflux for 5 h. To the resulting suspension was added EA and aq. sat. $Na_2CO_3$ and the mixture was extracted with DCM. The combined org. layers were dried ($MgSO_4$) and evaporated off. The residue was purified by CC (EA) to give 860 mg of the desired compound.

LC-MS (B): $t_R$=0.82 min; $[M+H]^+$: 250.14.

71.4. Acetic acid 4-chloro-3-methoxy-6-phenyl-pyridin-2-ylmethyl ester

A solution of intermediate 71.3 (430 mg) in $Ac_2O$ (7 ml) was heated at 120° C. for 45 min. The reaction mixture was evaporated off and the residue HV-dried to afford 465 mg of the desired compound, which was not further purified.

LC-MS (B): $t_R$=1.02 min; $[M+H]^+$: 291.98.

71.5. (4-chloro-3-methoxy-6-phenyl-pyridin-2-yl)-methanol

To a solution of intermediate 71.4 (920 mg) in MeOH (7 ml) was added a 1M NaOH solution (5 ml) and the reaction mixture was stirred at RT for 5 min. It was extracted with EA and the combined org. layers were dried ($MgSO_4$) and evaporated off to afford 780 mg of the desired compound, which was not further purified.

LC-MS (B): $t_R$=0.93 min; $[M+H]^+$: 249.98.

71.6. 4-chloro-3-methoxy-6-phenyl-pyridine-2-carboxylic acid

To a solution of intermediate 71.5 (780 mg) in dioxane (20 ml) was added a NaOH solution (125 mg in 400 ml of $H_2O$) followed by $KMnO_4$ (1.48 g) and the reaction mixture was stirred at RT for 5 h 30. A 2M HCl solution (150 ml) was added and the reaction mixture was stirred at RT for 20 min. EA (200 ml) was added and it was stirred for further 10 min. The phases were separated and the aq. phase was extracted with EA. The combined org. layers were washed with a NaCl solution, dried ($MgSO_4$) and evaporated off. The residue was taken up in toluene, the solution was evaporated off and the residue HV dried to afford 810 mg of the desired compound, which was not further purified.

LC-MS (B): $t_R$=0.90 min; $[M+H]^+$: 264.22.

71.7. 4-{(S)-4-tert-butoxycarbonyl-2-[(4-chloro-3-methoxy-6-phenyl-pyridine-2-carbonyl)-amino]-butyryl}-piperazine-1-carboxylic acid ethyl ester This compound was prepared using a method analogous to that of Example 1, step 1.7, intermediate 71.6 replacing intermediate 1.4. The compound was however purified by CC (Hept/EA 1/0 to 0/1).

LC-MS (B): $t_R$=1.07 min; $[M+H]^+$: 589.31.

71.8. 4-{(S)-4-tert-butoxycarbonyl-2-[(4-cyclopropyl-3-ethoxy-6-phenyl-pyridine-2-carbonyl)-amino]-butyryl}-piperazine-1-carboxylic acid ethyl ester This compound was prepared using a method analogous to that of Example 5, step 5.1, intermediate 71.7 replacing intermediate 1.3, cyclopropylboronic acid replacing phenylboronic acid, and using DME instead of DME/EtOH.

LC-MS (B): $t_R$=1.07 min; $[M+H]^+$: 595.54.

71.9. 4-{(S)-4-carboxy-2-[(4-cyclopropyl-3-methoxy-6-phenyl-pyridine-2 carbonyl)-amino]-butyryl}-piperazine-1-carboxylic acid ethyl ester This compound was prepared using a method analogous to that of Example 1, step 1.8, intermediate 71.8 replacing intermediate 1.7. The compound was however purified by preparative LC-MS (III) followed by CC (DCM/MeOH 9/1).
LC-MS (B): $t_R$=0.91 min; [M+H]$^+$: 539.48.

The compounds of Examples 72 to 74 were prepared using a method analogous to that of the Example indicated between brackets, except that the last step of the corresponding Example was not carried out.

Example 72

4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid butyl ester (Example 67). LC-MS (B): $t_R$=0.99 min; [M+H]$^+$: 652.32.

Example 73

4-((S)-4-tert-butoxycarbonyl-2-{[5-fluoro-4-(3-methoxy-pyrrolidin-1-yl)-6-phenyl-pyridine-2-carbonyl]-amino}-butyryl)-piperazine-1-carboxylic acid butyl ester (Example 70). LC-MS (B): $t_R$=1.16 min; [M+H]$^+$: 670.11.

Example 74

4-{(S)-4-tert-butoxycarbonyl-2-[(4-cyclopropyl-3-methoxy-6-phenyl-pyridine-2-carbonyl)-amino]-butyryl}-piperazine-1-carboxylic acid ethyl ester (Example 71). LC-MS (B): $t_R$=1.07 min; [M+H]$^+$: 595.54.

Example 75

4-{(S)-2-[(4-butylamino-5-fluoro-6-phenyl-pyridine-2-carbonyl)-amino]-4-carboxy-butyryl}-piperazine-1-carboxylic acid ethyl ester

75.1. 4-chloro-3-fluoro-pyridine 1-oxide

MCPBA (28.1 g) was added to a solution of 4-chloro-3-fluoro-pyridine (10.0 g) in DCM (150 ml) and the reaction mixture stirred for 60 h at RT. The reaction mixture was quenched with 10% aq. Na$_2$S$_2$O$_3$ and the basicity of the aq. phase adjusted with aq. sat. Na$_2$CO$_3$ to pH 9. The aq. phase was extracted with EA (6×), and the combined org. phase was dried over MgSO$_4$ and evaporated to dryness. The desired compound (8.4 g) was used in the next step without further purification.
LC-MS (B): $t_R$=0.46 min; [M+H]$^+$: 148.2.

75.2. 4-chloro-3-fluoro-2-phenyl-pyridine 1-oxide

To a solution of intermediate 75.1 (200 mg) in toluene (5 ml) was added, at RT, bromobenzene (0.57 ml), tri-tert-butylphosphonium tetrafluoroborate (59 mg), K$_2$CO$_3$ (537 mg) and Pd(OAc)$_2$ (72 mg). The reaction mixture was stirred overnight at 110° C. under argon. The reaction mixture was filtered off through Celite and evaporated to dryness. CC (DCM to DCM/MeOH 8/2) afforded the desired compound (136 mg).

75.3. 4-chloro-5-fluoro-6-phenyl-pyridine-2-carbonitrile

To a solution of intermediate 75.2 (20 mg) in DCM (5 ml) was added, at RT, TMSCN (27 mg) followed by AcCl (10 µl).

The reaction mixture was stirred overnight at RT. The reaction mixture was washed with aq. sat. Na$_2$CO$_3$ and the aq. layer extracted with EA (3×). The combined org. layers were dried over MgSO$_4$, filtered off, and evaporated to dryness to give 15 mg of the desired compound.
$^1$H-NMR (CDCl$_3$): 8.00 (m, 2H); 7.76 (d, 1H, J=4.5 Hz); 7.55 (m, 3H).
LC-MS (B): $t_R$=1.07 min.

75.4. 4-chloro-5-fluoro-6-phenyl-pyridine-2-carboxylic acid

To intermediate 75.3 (800 mg) was added at RT conc. HCl (1 ml) and the reaction mixture was stirred at 100° C. for 30 min. The reaction mixture was allowed to reach pH=4-5 with aq. sat. NaHCO$_3$ and the suspension was extracted with EA (3×). The combined org. layers were dried over MgSO$_4$, filtered off, and evaporated to dryness. The crude product (600 mg) was used without further purification.
LC-MS (B): $t_R$=0.96 min; [M+H]$^+$: 252.0.

75.5. 4-{(S)-4-tert-butoxycarbonyl-2-[(4-chloro-5-fluoro-6-phenyl-pyridine-2-carbonyl)-amino]-butyryl}-piperazine-1-carboxylic acid ethyl ester To a solution of intermediate 75.4 (270 mg) in DCM (4 ml) was added at RT PyBOP (614 mg). The reaction mixture was stirred for 15 min at RT, then DIPEA (0.22 ml) and intermediate 1.6 (400 mg) were added at RT. The reaction mixture was stirred overnight at RT. Aq. sat Na$_2$CO$_3$ was added and the aq. phase was extracted with EA (3×). The combined org. layers were dried over MgSO$_4$, filtered off and evaporated to dryness. CC (Hept to EA) provided the desired compound (230 mg).
LC-MS (B): $t_R$=1.14 min; [M+H]$^+$: 576.3.

75.6. 4-{(S)-2-[(4-butylamino-5-fluoro-6-phenyl-pyridine-2-carbonyl)-amino]-4 carboxy-butyryl}-piperazine-1-carboxylic acid ethyl ester A mixture of intermediate 75.5 (90 mg), acetato (2'-di-tert-butylphosphino-1,1'-biphenyl-2-yl)palladium (3.5 mg), tBuONa (54.3 mg) and butylamine (15 µl) in toluene (1 ml) was degassed and stirred under argon at 90° C. overnight. The reaction mixture was evaporated to dryness and directly purified by CC (DCM to DCM/MeOH 8:2) followed by preparative LC-MS (IV) to give the desired product (10 mg).
LC-MS (B): $t_R$=1.00 min; [M+H]$^+$: 557.9.

Example 76

4-{(S)-2-[(4-butylamino-5-fluoro-6-phenyl-pyridine-2-carbonyl)-amino]-4-carboxy-butyryl}-piperazine-1-carboxylic acid butyl ester

76.1. 4-{(S)-4-tert-butoxycarbonyl-2-[(4-chloro-5-fluoro-6-phenyl-pyridine-2-carbonyl)-amino]-butyryl}-piperazine-1-carboxylic acid butyl ester To a solution of intermediate 75.4 (270 mg) in DCM (4 ml) was added at RT PyBOP (614 mg). The reaction mixture was stirred for 15 min at RT, then DIPEA (0.22 ml) and intermediate 67.4 (as free base, 399 mg) were added at RT. The reaction mixture was stirred overnight at RT. Aq. sat Na$_2$CO$_3$ was added and the aq. phase was extracted with EA (3×). The combined org. layers were dried over MgSO$_4$, filtered off and evaporated to dryness. CC (Hept to EA) provided the desired compound (440 mg).

LC-MS (B): $t_R$=1.19 min; [M+H]$^+$: 604.9

76.2. 4-{(S)-2-[(4-butylamino-5-fluoro-6-phenyl-pyridine-2-carbonyl)-amino]-4 carboxy-butyryl}-piperazine-1-carboxylic acid butyl ester A mixture of intermediate 76.1 (100 mg), acetato (2'-di-tert-butylphosphino-1,1'-biphenyl-2-yl)palladium (1.5 mg), NaOtBu (44.5 mg) and butylamine (16 µl) in toluene (1 ml) was degassed and stirred under argon at 90° C. After 2 h, NaOtBu (16 mg) and 0.02 eq of the palladium catalyst (1.5 mg) were added and the reaction mixture further stirred at 90° C. overnight. The reaction mixture was evaporated to dryness and directly purified by CC (DCM to DCM/MeOH 8:2) followed by preparative LC-MS (IV).

LC-MS (B): $t_R$=1.06 min; [M+H]$^+$: 586.0.

The compounds of Examples 77 and 78 were prepared using a method analogous to that of the Example indicated between brackets, except that the last step of the corresponding Example was not carried out.

Example 77

4-{(S)-4-tert-butoxycarbonyl-2-[(4-chloro-5-fluoro-6-phenyl-pyridine-2-carbonyl)-amino]-butyryl}-piperazine-1-carboxylic acid ethyl ester (Example 75). LC-MS (B): $t_R$=1.14 min; [M+H]$^+$: 576.3.

Example 78

4-{(S)-4-tert-butoxycarbonyl-2-[(4-chloro-5-fluoro-6-phenyl-pyridine-2-carbonyl)-amino]-butyryl}-piperazine-1-carboxylic acid butyl ester (Example 76). LC-MS (B): $t_R$=1.19 min; [M+H]$^+$: 604.9

Biological Tests
P2Y$_{12}$ Receptor Binding Assay
Procedure

Chinese Hamster Ovary (CHO) cells with recombinant expression of the human P2Y$_{12}$ receptor were cultured in 24 well cell-culture plates. Cells were washed three times with binding buffer (50 mM Tris pH 7.4, 100 mM NaCl, 1 mM EDTA, 0.5% BSA). The cells were then incubated with 0.5 ml per well binding buffer containing tritium-labeled 2-methyl-thio-adenosine 5'-diphosphate (2-methyl-S-ADP) (between 100'000 and 300'000 dpm per well) and various concentrations of test compounds. After incubation at RT for 2 hours, cells were washed three times with binding buffer. Then, cells were solubilized by addition of 0.5 ml solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Results Obtained for the Compounds of Formula I

Using the procedure described above for the P2Y$_{12}$ receptor binding assay, IC$_{50}$s ranging from 8 nM to 35 µM, with an average value of about 908 nM, were measured for the compounds of the Examples 1 to 38, 66 to 71, 75 and 76.

For example, the following results could be obtained for the Example compounds using the procedure described above for the P2Y$_{12}$ receptor binding assay:

| Example No. | IC$_{50}$ at P2Y$_{12}$ receptor binding assay (nM) |
|---|---|
| 1 | 34 |
| 24 | 204 |
| 28 | 96 |
| 32 | 67 |
| 37 | 94 |
| 66 | 40 |
| 69 | 109 |
| 71 | 510 |
| 75 | 386 |

Besides, the following additional results could be obtained for the Example compounds using the procedure described above for the P2Y$_{12}$ receptor binding assay:

| Example No. | IC$_{50}$ at P2Y$_{12}$ receptor binding assay (nM) |
|---|---|
| 39 | 2148 |
| 72 | 1760 |

The invention claimed is:
1. A compound of formula I

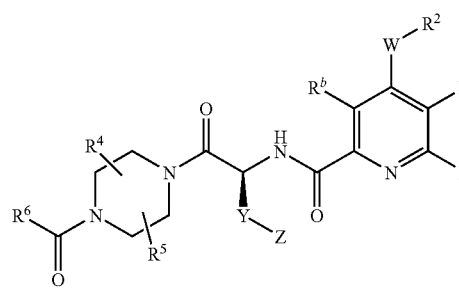

wherein
R$^1$ represents an imidazolyl, pyrazolyl, 1,2,3-triazolyl or 1,2,4-triazolyl ring, which ring may be substituted by a methyl group, or also R$^1$ represents phenyl optionally substituted 1 to 3 times by substituents each independently selected from the group consisting of halogen, methyl, methoxy, trifluoromethyl and trifluoromethoxy;
W represents a bond and R$^2$ represents hydrogen, halogen, alkyl, hydroxyalkyl, alkoxyalkyl, cycloalkyl, aryl or heteroaryl; or
W represents —O— or —S— and R$^2$ represents alkyl, cycloalkyl, aryl or heterocyclyl; or
W represents —NR$^3$—, R$^2$ represents alkyl, hydroxyalkyl or alkoxyalkyl and R$^3$ represents hydrogen or alkyl; or
W represents —C≡C— and R$^2$ represents hydroxyalkyl or alkoxyalkyl; or
W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy; or also
W represents —NR$^3$— and R$^2$ and R$^3$ form, together with the nitrogen that carries them, an imidazolyl, pyrazolyl, 1,2,3-triazolyl or 1,2,4-triazolyl ring, which ring is optionally substituted by a methyl group;

$R^a$ represents hydrogen or fluorine and $R^b$ represents hydrogen, or $R^a$ represents hydrogen and $R^b$ represents alkoxy;

each of $R^4$ and $R^5$ represents independently hydrogen or methyl;

$R^6$ represents alkoxy; and

Y represents alkylene or phenylalkylene, and Z represents —OH, —COOH, cyano, tetrazolyl or —COOR$^7$, $R^7$ representing alkyl;

it being understood that:
  when $R^a$ represents fluorine then: i) $R^1$ represents phenyl optionally substituted once by fluorine, methyl, methoxy, trifluoromethyl or trifluoromethoxy, ii) W does not represent —O— or —S—, and iii) if W is a bond, then $R^2$ does not represent hydrogen;

in free or salt form.

2. The compound according to formula I as defined in claim 1, which is also a compound of formula $I_P$

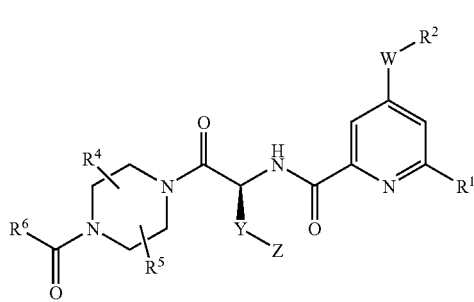

wherein
  $R^1$ represents phenyl optionally substituted once by a substituent selected from the group consisting of halogen, methyl, methoxy, trifluoromethyl and trifluoromethoxy;
  W represents a bond and $R^2$ represents hydrogen, halogen, alkyl, hydroxyalkyl, alkoxyalkyl, cycloalkyl, aryl or heteroaryl; or
  W represents —O— or —S— and $R^2$ represents alkyl, cycloalkyl, aryl or heterocyclyl; or
  W represents —NR$^3$—, $R^2$ represents alkyl, hydroxyalkyl or alkoxyalkyl and $R^3$ represents hydrogen or alkyl; or
  W represents —C≡C— and $R^2$ represents hydroxyalkyl or alkoxyalkyl; or
  W represents —NR$^3$— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, $R^x$ representing hydroxy, hydroxymethyl, alkoxymethyl or alkoxy; or also
  W represents —NR$^3$— and $R^2$ and $R^3$ form, together with the nitrogen that carries them, an imidazolyl, pyrazolyl, 1,2,3-triazolyl or 1,2,4-triazolyl ring, which ring is optionally substituted by a methyl group;

each of $R^4$ and $R^5$ represents independently hydrogen or methyl;

$R^6$ represents alkoxy; and

Y represents alkylene or phenylalkylene, and Z represents —OH, —COOH, cyano, tetrazolyl or —COOR$^7$, $R^7$ representing alkyl;

in free or salt form.

3. The compound according to claim 1, wherein W represents a bond in free or salt form.

4. The compound according to claim 1, wherein W represents —O— in free or salt form.

5. The compound according to claim 1, wherein W represents —S— in free or salt form.

6. The compound according to claim 1, wherein W represents —NR$^3$— in free or salt form.

7. The compound according to claim 1, wherein W represents —C≡C— in free or salt form.

8. The compound according to claim 1, wherein $R^1$ represents phenyl optionally substituted once by a substituent selected from the group consisting of halogen, methyl, methoxy, trifluoromethyl and trifluoromethoxy in free or salt form.

9. The compound according to claim 1, wherein Y represents alkylene or phenylalkylene and Z represents —COOH in free or salt form.

10. The compound according to claim 1, wherein $R^2$ represents fluorine and $R^b$ represents hydrogen in free or salt form.

11. The compound according to claim 1, which is selected from the group consisting of:
  4-{(S)-4-carboxy-2-[(4-chloro-6-phenyl-pyridine-2-carbonyl)-amino]-butyryl}-piperazine-1-carboxylic acid ethyl ester;
  4-{(S)-4-carboxy-2-[(4-cyclopentyloxy-6-phenyl-pyridine-2-carbonyl)-amino]-butyryl}-piperazine-1-carboxylic acid ethyl ester;
  4-((S)-4-carboxy-2-{[4-(1-hydroxy-1-methyl-ethyl)-6-phenyl-pyridine-2-carbonyl]-amino}-butyryl)-piperazine-1-carboxylic acid ethyl ester;
  4-{(S)-4-carboxy-2-[(4,6-diphenyl-pyridine-2-carbonyl)-amino]-butyryl}-piperazine-1-carboxylic acid ethyl ester;
  4-{(S)-4-carboxy-2-[(6-phenyl-4-pyrazol-1-yl-pyridine-2-carbonyl)-amino]-butyryl}-piperazine-1-carboxylic acid ethyl ester;
  4-((S)-4-carboxy-2-{[4-(4-methoxy-phenyl)-6-phenyl-pyridine-2-carbonyl]-amino}-butyryl)-piperazine-1-carboxylic acid ethyl ester;
  4-((S)-4-carboxy-2-{[4-cyclopropyl-6-phenyl-pyridine-2-carbonyl]-amino}-butyryl)-piperazine-1-carboxylic acid ethyl ester;
  4-{(S)-2-[(4-butyl-6-phenyl-pyridine-2-carbonyl)-amino]-4-carboxy-butyryl}-piperazine-1-carboxylic acid ethyl ester;
  4-((S)-4-carboxy-2-{[6-(2-fluoro-phenyl)-4-phenyl-pyridine-2-carbonyl]-amino}-butyryl)-piperazine-1-carboxylic acid ethyl ester;
  4-((S)-4-carboxy-2-{[6-(4-fluoro-phenyl)-4-phenyl-pyridine-2-carbonyl]-amino}-butyryl)-piperazine-1-carboxylic acid ethyl ester;
  4-{(S)-4-carboxy-2-[(4-phenyl-6-o-tolyl-pyridine-2-carbonyl)-amino]-butyryl}-piperazine-1-carboxylic acid ethyl ester;
  4-{(S)-4-carboxy-2-[(4-phenyl-6-p-tolyl-pyridine-2-carbonyl)-amino]-butyryl}-piperazine-1-carboxylic acid ethyl ester;
  4-((S)-4-carboxy-2-{[4-((R)-3-hydroxy-pyrrolidin-1-yl)-6-phenyl-pyridine-2-carbonyl]-amino}-butyryl)-piperazine-1-carboxylic acid ethyl ester;
  4-{(S)-4-carboxy-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester;
  4-{(S)-4-carboxy-2-[(6-phenyl-4-pyrrolidin-1-yl-pyridine-2-carbonyl)-amino]-butyryl}-piperazine-1-carboxylic acid ethyl ester;

4-((S)-4-carboxy-2-{[4-(2-hydroxy-ethylamino)-6-phenyl-pyridine-2-carbonyl]-amino}-butyryl)-piperazine-1-carboxylic acid ethyl ester;

4-((S)-4-carboxy-2-{[4-((S)-3-methoxy-pyrrolidin-1-yl)-6-phenyl-pyridine-2-carbonyl]-amino}-butyryl)-piperazine-1-carboxylic acid ethyl ester;

4-{(S)-4-carboxy-2-[(4-isopropylamino-6-phenyl-pyridine-2-carbonyl)-amino]-butyryl}-piperazine-1-carboxylic acid ethyl ester;

4-((S)-4-carboxy-2-{[4-(2-methoxymethyl-cyclopropyl)-6-phenyl-pyridine-2-carbonyl]-amino}-butyryl)-piperazine-1-carboxylic acid ethyl ester;

4-((S)-4-carboxy-2-{[4-(2-hydroxymethyl-cyclopropyl)-6-phenyl-pyridine-2-carbonyl]-amino}-butyryl)-piperazine-1-carboxylic acid ethyl ester;

4-{(S)-3-cyano-2-[(4,6-diphenyl-pyridine-2-carbonyl)-amino]-propionyl}-piperazine-1-carboxylic acid ethyl ester;

4-{(S)-4-carboxy-2-[(4,6-diphenyl-pyridine-2-carbonyl)-amino]-butyryl}-3-methyl-piperazine-1-carboxylic acid ethyl ester;

4-{(S)-2-[(4,6-diphenyl-pyridine-2-carbonyl)-amino]-3-hydroxy-propionyl}-piperazine-1-carboxylic acid ethyl ester;

4-{(S)-4-carboxy-2-[(4-phenyl-6-pyrazol-1-yl-pyridine-2-carbonyl)-amino]-butyryl}-piperazine-1-carboxylic acid ethyl ester;

4-((S)-4-carboxy-2-{[4-(3-hydroxy-propyl)-6-phenyl-pyridine-2-carbonyl]-amino}-butyryl)-piperazine-1-carboxylic acid ethyl ester;

4-((S)-4-carboxy-2-{[4-(3-hydroxy-3-methyl-but-1-ynyl)-6-phenyl-pyridine-2-carbonyl]-amino}-butyryl)-piperazine-1-carboxylic acid ethyl ester;

4-((S)-4-carboxy-2-{[4-(3-hydroxy-3-methyl-butyl)-6-phenyl-pyridine-2-carbonyl]-amino}-butyryl)-piperazine-1-carboxylic acid ethyl ester;

4-((S)-4-carboxy-2-{[4-(4-hydroxy-cyclohexyl)-6-phenyl-pyridine-2-carbonyl]-amino}-butyryl)-piperazine-1-carboxylic acid ethyl ester;

4-{(S)-4-carboxy-2-[(6-phenyl-4-phenylsulfanyl-pyridine-2-carbonyl)-amino]-butyryl}-piperazine-1-carboxylic acid ethyl ester;

4-((S)-4-carboxy-2-{[4-(2-hydroxy-cyclohexyl)-6-phenyl-pyridine-2-carbonyl]-amino}-butyryl)-piperazine-1-carboxylic acid ethyl ester;

4-{(S)-4-carboxy-2-[(6-phenyl-4-thiophen-3-yl-pyridine-2-carbonyl)-amino]-butyryl}-piperazine-1-carboxylic acid ethyl ester;

4-{(S)-4-carboxy-2-[(4-furan-3-yl-6-phenyl-pyridine-2-carbonyl)-amino]-butyryl}-piperazine-1-carboxylic acid ethyl ester;

4-{(S)-4-carboxy-2-[(4-isopropylsulfanyl-6-phenyl-pyridine-2-carbonyl)-amino]-butyryl}-piperazine-1-carboxylic acid ethyl ester;

4-((S)-3-(4-carboxy-phenyl)-2-{[4-(2-methoxymethyl-cyclopropyl)-6-phenyl-pyridine-2-carbonyl]-amino}-propionyl)-piperazine-1-carboxylic acid ethyl ester;

4-{(S)-4-carboxy-2-[(4-methyl-6-phenyl-pyridine-2-carbonyl)-amino]-butyryl}-piperazine-1-carboxylic acid ethyl ester;

4-((S)-4-carboxy-2-{[6-phenyl-4-(tetrahydro-furan-3-yloxy)-pyridine-2-carbonyl]-amino}-butyryl)-piperazine-1-carboxylic acid ethyl ester;

4-{(S)-4-carboxy-2-[(6-phenyl-pyridine-2-carbonyl)-amino]-butyryl}-piperazine-1-carboxylic acid ethyl ester;

4-{(S)-4-O-tert-butoxycarbonyl-2-[(4-chloro-6-phenyl-pyridine-2-carbonyl)-amino]-butyryl}-piperazine-1-carboxylic acid ethyl ester;

4-{(S)-4-tert-butoxycarbonyl-2-[(4-cyclopentyloxy-6-phenyl-pyridine-2 carbonyl)-amino]-butyryl}-piperazine-1-carboxylic acid ethyl ester;

4-((S)-4-tert-butoxycarbonyl-2-{[4-(1-hydroxy-1-methyl-ethyl)-6-phenyl-pyridine-2-carbonyl]-amino}-butyryl)-piperazine-1-carboxylic acid ethyl ester;

4-{(S)-4-tert-butoxycarbonyl-2-[(4,6-diphenyl-pyridine-2-carbonyl)-amino]-butyryl}-piperazine-1-carboxylic acid ethyl ester;

4-{(S)-4-tert-butoxycarbonyl-2-[(6-phenyl-4-pyrazol-1-yl-pyridine-2-carbonyl)-amino]-butyryl}-piperazine-1-carboxylic acid ethyl ester;

4-((S)-4-tert-butoxycarbonyl-2-{[4-(4-methoxy-phenyl)-6-phenyl-pyridine-2-carbonyl]-amino}-butyryl)-piperazine-1-carboxylic acid ethyl ester;

4-((S)-4-tert-butoxycarbonyl-2-{[4-cyclopropyl-6-phenyl-pyridine-2-carbonyl]-amino}-butyryl)-piperazine-1-carboxylic acid ethyl ester;

4-{(S)-4-tert-butoxycarbonyl-2-[(4-butyl-6-phenyl-pyridine-2-carbonyl)-amino]-butyryl}-piperazine-1-carboxylic acid ethyl ester;

4-{(S)-4-O-tert-butoxycarbonyl-2-[(4-[(R)-3-hydroxy-pyrrolidin-1-yl]-6-phenyl-pyridine-2-carbonyl)-amino]-butyryl}-piperazine-1-carboxylic acid ethyl ester;

4-{(S)-4-tert-butoxycarbonyl-2-[(4-hydroxy-6'-phenyl-3,4,5,6-tetrahydro-2H-[1,4']bipyridinyl-2'-carbonyl)-amino]-butyryl}-piperazine-1-carboxylic acid ethyl ester;

4-{(S)-4-tert-butoxycarbonyl-2-[(6-phenyl-4-pyrrolidin-1-yl-pyridine-2-carbonyl)-amino]-butyryl}-piperazine-1-carboxylic acid ethyl ester;

4-((S)-4-tert-butoxycarbonyl-2-{[4-(2-hydroxy-ethylamino)-6-phenyl-pyridine-2-carbonyl]-amino}-butyryl)-piperazine-1-carboxylic acid ethyl ester;

4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid ethyl ester;

4-{(S)-4-tert-butoxycarbonyl-2-[(4-isopropylamino-6-phenyl-pyridine-2-carbonyl)-amino]-butyryl}-piperazine-1-carboxylic acid ethyl ester;

4-((S)-4-tert-butoxycarbonyl-2-{[4-(2-methoxymethyl-cyclopropyl)-6-phenyl-pyridine-2-carbonyl]-amino}-butyryl)-piperazine-1-carboxylic acid ethyl ester;

4-((S)-4-tert-butoxycarbonyl-2-{[4-(2-hydroxymethyl-cyclopropyl)-6-phenyl-pyridine-2-carbonyl]-amino}-butyryl)-piperazine-1-carboxylic acid ethyl ester;

4-{(S)-4-tert-butoxycarbonyl-2-[(4,6-diphenyl-pyridine-2-carbonyl)-amino]-butyryl}-3-methyl-piperazine-1-carboxylic acid ethyl ester;

4-{(S)-4-tert-butoxycarbonyl-2-[(4-phenyl-6-pyrazol-1-yl-pyridine-2-carbonyl)-amino]-butyryl}-piperazine-1-carboxylic acid ethyl ester;

4-((S)-4-tert-butoxycarbonyl-2-{[4-(3-hydroxy-propyl)-6-phenyl-pyridine-2-carbonyl]-amino}-butyryl)-piperazine-1-carboxylic acid ethyl ester;

4-((S)-4-tert-butoxycarbonyl-2-{[4-(3-hydroxy-3-methyl-but-1-ynyl)-6-phenyl-pyridine-2-carbonyl]-amino}-butyryl)-piperazine-1-carboxylic acid ethyl ester;

4-((S)-4-tert-butoxycarbonyl-2-{[4-(3-hydroxy-3-methyl-butyl)-6-phenyl-pyridine-2-carbonyl]-amino}-butyryl)-piperazine-1-carboxylic acid ethyl ester;

4-{(S)-4-tert-butoxycarbonyl-2-[(6-phenyl-4-phenylsulfanyl-pyridine-2-carbonyl)-amino]-butyryl}-piperazine-1-carboxylic acid ethyl ester;
4-{(S)-4-tert-butoxycarbonyl-2-[(6-phenyl-4-thiophen-3-yl-pyridine-2-carbonyl)-amino]-butyryl}-piperazine-1-carboxylic acid ethyl ester;
4-{(S)-4-tert-butoxycarbonyl-2-[(4-furan-3-yl-6-phenyl-pyridine-2-carbonyl)-amino]-butyryl}-piperazine-1-carboxylic acid ethyl ester;
4-{(S)-4-tert-butoxycarbonyl-2-[(4-isopropylsulfanyl-6-phenyl-pyridine-2-carbonyl)-amino]-butyryl}-piperazine-1-carboxylic acid ethyl ester;
4-((S)-3-(4-tert-butoxycarbonyl-phenyl)-2-{[4-(2-methoxymethyl-cyclopropyl)-6-phenyl-pyridine-2-carbonyl]-amino}-propionyl)-piperazine-1-carboxylic acid ethyl ester;
4-{(S)-4-tert-butoxycarbonyl-2-[(6-phenyl-pyridine-2-carbonyl)-amino]-butyryl}-piperazine-1-carboxylic acid ethyl ester;
4-[(S)-2-[(4,6-diphenyl-pyridine-2-carbonyl)-amino]-3-(2H-tetrazol-5-yl)-propionyl]-piperazine-1-carboxylic acid ethyl ester;
4-((S)-4-carboxy-2-{[4-((S)-3-methoxy-pyrrolidin-1-yl)-6-phenyl-pyridine-2-carbonyl]-amino}-butyryl)-piperazine-1-carboxylic acid butyl ester;
4-((S)-3-hydroxy-2-{[4-((S)-3-methoxy-pyrrolidin-1-yl)-6-phenyl-pyridine-2-carbonyl]-amino}-propionyl)-piperazine-1-carboxylic acid butyl ester;
4-((S)-2-{[4-((S)-3-methoxy-pyrrolidin-1-yl)-6-phenyl-pyridine-2-carbonyl]-amino}-3-methyl-butyryl)-piperazine-1-carboxylic acid butyl ester;
4-((S)-4-carboxy-2-{[5-fluoro-4-((S)-3-methoxy-pyrrolidin-1-yl)-6-phenyl-pyridine-2-carbonyl]-amino}-butyryl)-piperazine-1-carboxylic acid butyl ester;
4-{(S)-4-carboxy-2-[(4-cyclopropyl-3-methoxy-6-phenyl-pyridine-2-carbonyl)-amino]-butyryl}-piperazine-1-carboxylic acid ethyl ester;
4-((S)-4-tert-butoxycarbonyl-2-{[4-((S)-3-methoxy-pyrrolidin-1-yl)-6-phenyl-pyridine-2-carbonyl]-amino}-butyryl)-piperazine-1-carboxylic acid butyl ester;
4-((S)-4-tert-butoxycarbonyl-2-{[5-fluoro-4-(3-methoxy-pyrrolidin-1-yl)-6-phenyl-pyridine-2-carbonyl]-amino}-butyryl)-piperazine-1-carboxylic acid butyl ester;
4-{(S)-4-tert-butoxycarbonyl-2-[(4-cyclopropyl-3-methoxy-6-phenyl-pyridine-2-carbonyl)-amino]-butyryl}-piperazine-1-carboxylic acid ethyl ester;
4-{(5)-2-[(4-butylamino-5-fluoro-6-phenyl-pyridine-2-carbonyl)-amino]-4-carboxy-butyryl}-piperazine-1-carboxylic acid ethyl ester;
4-{(5)-2-[(4-butylamino-5-fluoro-6-phenyl-pyridine-2-carbonyl)-amino]-4-carboxy-butyryl}-piperazine-1-carboxylic acid butyl ester;
4-{(S)-4-tert-butoxycarbonyl-2-[(4-chloro-5-fluoro-6-phenyl-pyridine-2-carbonyl)-amino]-butyryl}-piperazine-1-carboxylic acid ethyl ester; and
4-{(S)-4-tert-butoxycarbonyl-2-[(4-chloro-5-fluoro-6-phenyl-pyridine-2-carbonyl)-amino]-butyryl}-piperazine-1-carboxylic acid butyl ester;
in free or a pharmaceutically acceptable salt form.

12. A pharmaceutical composition containing at least one compound of formula I as defined in claim 1, in free or pharmaceutically acceptable salt form, and a pharmaceutically acceptable carrier, diluent or excipient.

13. A method for treating myocardial infarction, arterial thrombosis, transient ischaemic attacks, peripheral vascular disease and stable or unstable angina, comprising administering to a patient in need thereof an effective amount of a compound of formula I as defined in claim 1, in free or pharmaceutically acceptable salt form.

14. A method for treating thrombosis, comprising administering to patient in need thereof an effective amount of a compound of formula I as defined in claim 1, in free or pharmaceutically acceptable salt form.

15. The compound according to claim 2, wherein
$R^1$ represents phenyl optionally substituted once by halogen or methyl;
W represents a bond and $R^2$ represents hydroxyalkyl, alkoxyalkyl or cycloalkyl optionally substituted once by a member of the group consisting of hydroxy, hydroxymethyl, methoxymethyl, methoxy and ethoxy; or
W represents —O— or —S— and $R^2$ represents heterocyclyl; or
W represents —NR$^3$—, $R^2$ represents hydroxyalkyl or alkoxyalkyl and $R^3$ represents hydrogen; or
W represents —C≡C— and $R^2$ represents hydroxyalkyl or alkoxyalkyl; or
W represents —NR$^3$— and $R^2$ and $R^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl, methoxy or ethoxy; or also
W represents —NR$^3$— and $R^2$ and $R^3$ form, together with the nitrogen that carries them, an imidazolyl, pyrazolyl, 1,2,3-triazolyl or 1,2,4-triazolyl ring;
one of $R^4$ and $R^5$ represents hydrogen or methyl and the other represents hydrogen;
Y represents alkylene or phenylalkylene and Z represents —COON;
in free or salt form.

16. A method for treating myocardial infarction, arterial thrombosis, transient ischaemic attacks, peripheral vascular disease and stable or unstable angina, comprising administering to a patient in need thereof an effective amount of a compound of formula $I_P$ as defined in claim 15, in free or pharmaceutically acceptable salt form.

17. A method for treating thrombosis, comprising administering to patient in need thereof an effective amount of a compound of formula $I_P$ as defined in claim 15, in free or pharmaceutically acceptable salt form.

* * * * *

UNITED STATES PATENT AND TRADEMARK OFFICE
CERTIFICATE OF CORRECTION

PATENT NO. : 8,093,250 B2
APPLICATION NO. : 12/445352
DATED : January 10, 2012
INVENTOR(S) : Caroff et al.

Page 1 of 1

It is certified that error appears in the above-identified patent and that said Letters Patent is hereby corrected as shown below:

Title Page
(75) Inventor "Emmanuel Meyers" should be "Emmanuel Meyer".

Col. 93, Lines 48-50,
"4-{(5)-2-[(4-butylamino-5-fluoro-6-phenyl-pyridine-2-carbonyl)-amino]-4-carboxy-butyryl}-piperazine-1-carboxylic acid ethyl ester" should be
"4-{(S)-2-[(4-butylamino-5-fluoro-6-phenyl-pyridine-2-carbonyl)-amino]-4-carboxy-butyryl}-piperazine-1-carboxylic acid ethyl ester".

Col. 94, line 46, "-COON;" should be "-COOH;".

Signed and Sealed this
First Day of May, 2012

David J. Kappos
*Director of the United States Patent and Trademark Office*